US012717168B2

(12) United States Patent
Back et al.

(10) Patent No.: US 12,717,168 B2
(45) **Date of Patent: *Aug. 25, 2026**

(54) OPHTHALMIC LENSES FOR REDUCING, MINIMIZING, AND/OR ELIMINATING INTERFERENCE ON IN-FOCUS IMAGES BY OUT-OF-FOCUS LIGHT

(71) Applicant: Brien Holden Vision Institute Limited, Sydney (AU)

(72) Inventors: Arthur Back, Danville, CA (US); Hassan Esfandiarijahromi, Campsie (AU)

(73) Assignee: Brien Holden Vision Institute Limited, Sydney (AU)

( * ) Notice: Subject to any disclaimer, the term of this patent is extended or adjusted under 35 U.S.C. 154(b) by 1029 days.

This patent is subject to a terminal disclaimer.

(21) Appl. No.: 17/637,359

(22) PCT Filed: Aug. 21, 2020

(86) PCT No.: PCT/IB2020/057863

§ 371 (c)(1),
(2) Date: Feb. 22, 2022

(87) PCT Pub. No.: WO2021/038405

PCT Pub. Date: Mar. 4, 2021

(65) Prior Publication Data

US 2022/0296361 A1 Sep. 22, 2022

Related U.S. Application Data

(60) Provisional application No. 62/890,809, filed on Aug. 23, 2019.

(51) Int. Cl.

| | |
|---|---|
| ***G02C 7/04*** | (2006.01) |
| ***A61F 2/16*** | (2006.01) |
| ***G02C 7/06*** | (2006.01) |

(52) U.S. Cl.
CPC .............. *G02C 7/06* (2013.01); *A61F 2/1618* (2013.01); *G02C 7/041* (2013.01); *G02C 7/042* (2013.01); *G02C 7/045* (2013.01); *G02C 2202/20* (2013.01)

(58) Field of Classification Search
None
See application file for complete search history.

(56) References Cited

U.S. PATENT DOCUMENTS 8,573,775 B2 11/2013 Weeber
9,329,407 B2 * 5/2016 Cathey, Jr ................. A61F 2/14
(Continued)

FOREIGN PATENT DOCUMENTS

AU 2006301940 4/2007
AU 2016203870 1/2017
(Continued)

OTHER PUBLICATIONS

Korean examination report dated Feb. 27, 2025 for KR 10-2022-7009575, with English Translation.
(Continued)

*Primary Examiner* — Darryl J Collins
(74) *Attorney, Agent, or Firm* — Jones Day

(57) ABSTRACT

An ophthalmic lens comprising: at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points positioned off-axis relative to the first focal point and on at least one focal plane different than a focal plane corresponding to the first focal point; wherein the at least one second (Continued)

optical zone is configured such that the light extending beyond the one or more focal points provides extended depth of focus.

23 Claims, 46 Drawing Sheets

(56) References Cited

U.S. PATENT DOCUMENTS

| | | | | |
|---|---|---|---|---|
| 9,931,200 | B2 * | 4/2018 | Van Der Mooren | A61F 2/1618 |
| 11,061,253 | B2 * | 7/2021 | Back | A61F 2/1618 |
| 2012/0206691 | A1 | 8/2012 | Iwai | |
| 2017/0184875 | A1 | 6/2017 | Newman | |
| 2019/0171036 | A1 | 6/2019 | Weeber | |
| 2019/0212579 | A1 | 7/2019 | Holden et al. | |
| 2019/0227342 | A1 * | 7/2019 | Brennan | G02C 7/02 |
| 2019/0235278 | A1 | 8/2019 | Bakaraju et al. | |

FOREIGN PATENT DOCUMENTS

| | | |
|---|---|---|
| CN | 103389586 | 11/2013 |
| CN | 109031696 | 12/2018 |
| EP | 0605841 | 7/1994 |
| JP | A-2009-540373 | 11/2009 |
| JP | A-2017-010031 | 1/2017 |
| WO | WO2019166653 A1 | 9/2019 |
| WO | WO2019166654 A1 | 9/2019 |
| WO | WO2019166655 A1 | 9/2019 |
| WO | WO2019166657 A1 | 9/2019 |
| WO | WO2019166659 A1 | 9/2019 |
| WO | WO2019166659 A9 | 9/2019 |

OTHER PUBLICATIONS

Indian Examination Report dated Aug. 30, 2024 for Application No. 202247014257.

International Search Report dated Oct. 19, 2020 for PCT/IB2020/057863.

Taiwanese Search Report dated Jul. 8, 2025 for 113146590, with English Translation.

Australian Examination Report dated Jul. 1, 2025 for AU 2020335361.

Taiwanese Office Action and Search Report dated Mar. 11, 2026 for 114138752, with English Translation.

* cited by examiner

LSR Value: 0.0 mm
Pupillary zone: 6 mm
101
102

OP2
OP 1
OP3
Distance Focus
DF2
DF1
DF3

LSR Value: 0.0 mm
Pupillary zone: 6 mm
101
102
102

OP2
OP1
OP3
Distance Focus
DF2
DF1
DF3

FIG. 3A

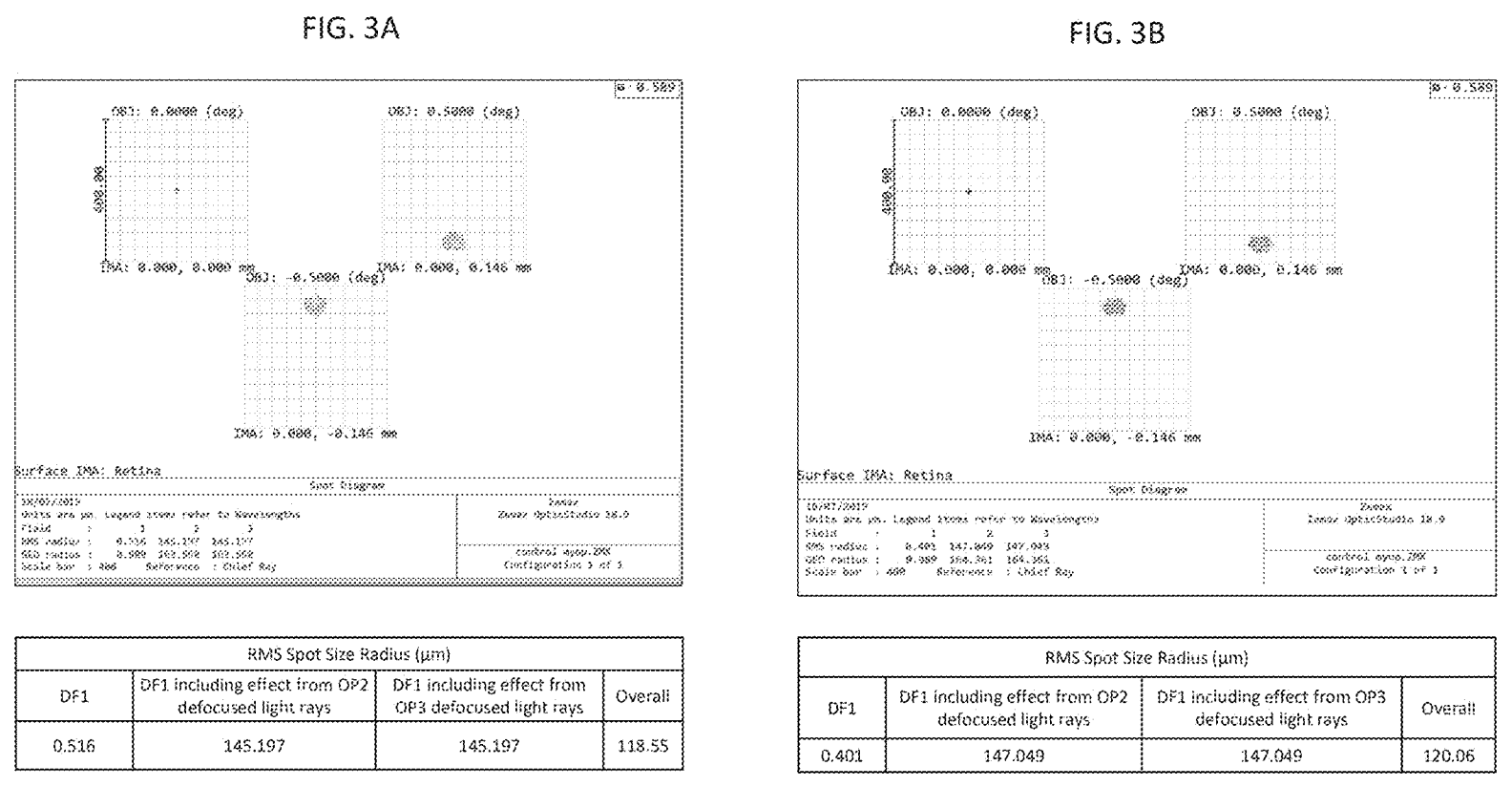

| RMS Spot Size Radius (µm) | | | |
|---|---|---|---|
| DF1 | DF1 including effect from OP2 defocused light rays | DF1 including effect from OP3 defocused light rays | Overall |
| 0.516 | 145.197 | 145.197 | 118.55 |

FIG. 3B

| RMS Spot Size Radius (µm) | | | |
|---|---|---|---|
| DF1 | DF1 including effect from OP2 defocused light rays | DF1 including effect from OP3 defocused light rays | Overall |
| 0.401 | 147.049 | 147.049 | 120.06 |

LSR Value: 0.5 mm Pupillary zone: 6 mm

LSR Value: 0.6 mm Pupillary zone 6 mm

FIG. 6A

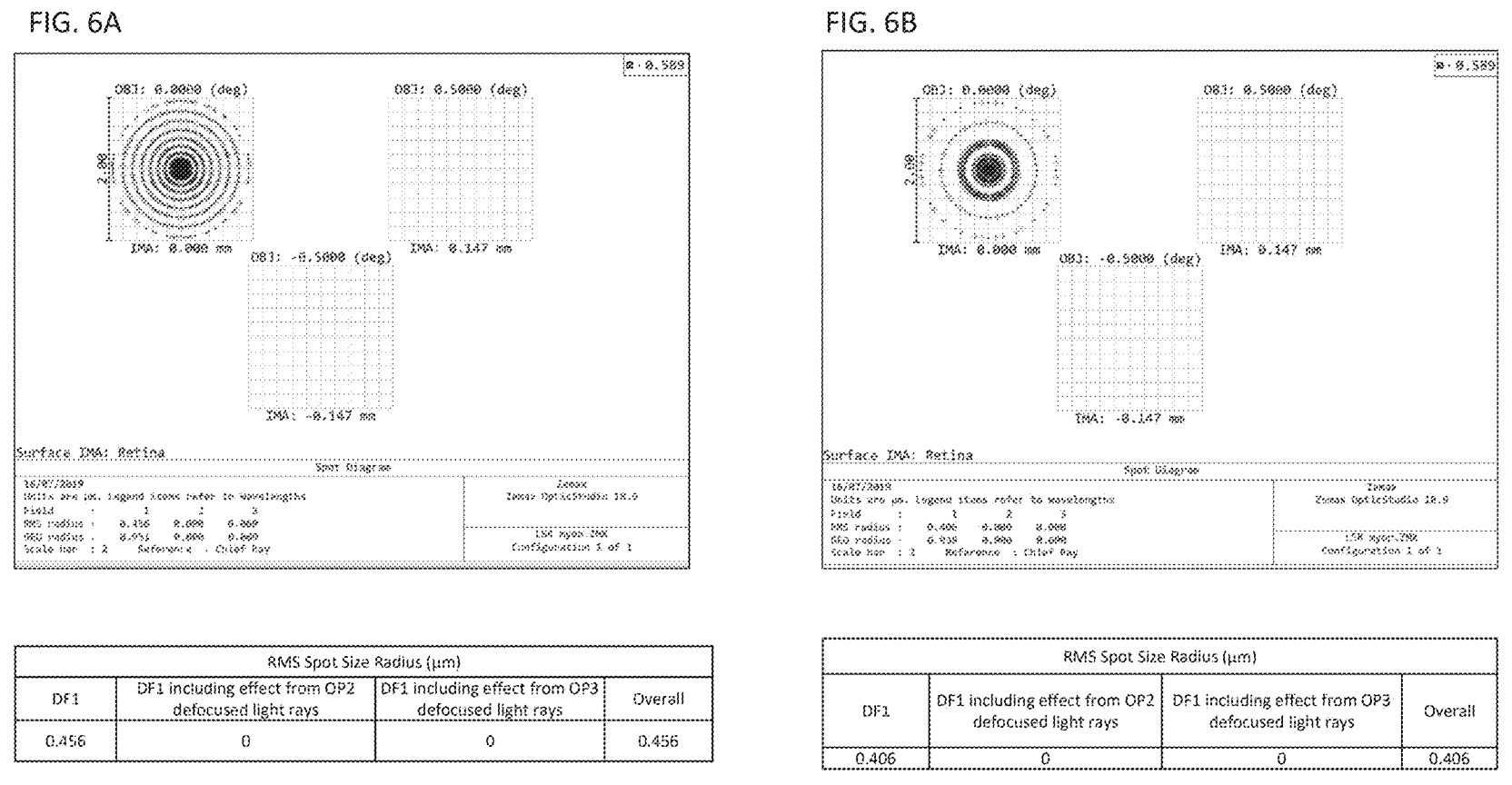

| RMS Spot Size Radius (µm) | | | |
|---|---|---|---|
| DF1 | DF1 including effect from OP2 defocused light rays | DF1 including effect from OP3 defocused light rays | Overall |
| 0.456 | 0 | 0 | 0.456 |

FIG. 6B

| RMS Spot Size Radius (µm) | | | |
|---|---|---|---|
| DF1 | DF1 including effect from OP2 defocused light rays | DF1 including effect from OP3 defocused light rays | Overall |
| 0.406 | 0 | 0 | 0.406 |

LSR Value: 0.45 mm Pupillary zone: 6 mm

LSR Value: 0.0 mm Pupillary zone: 6 mm

FIG. 9A

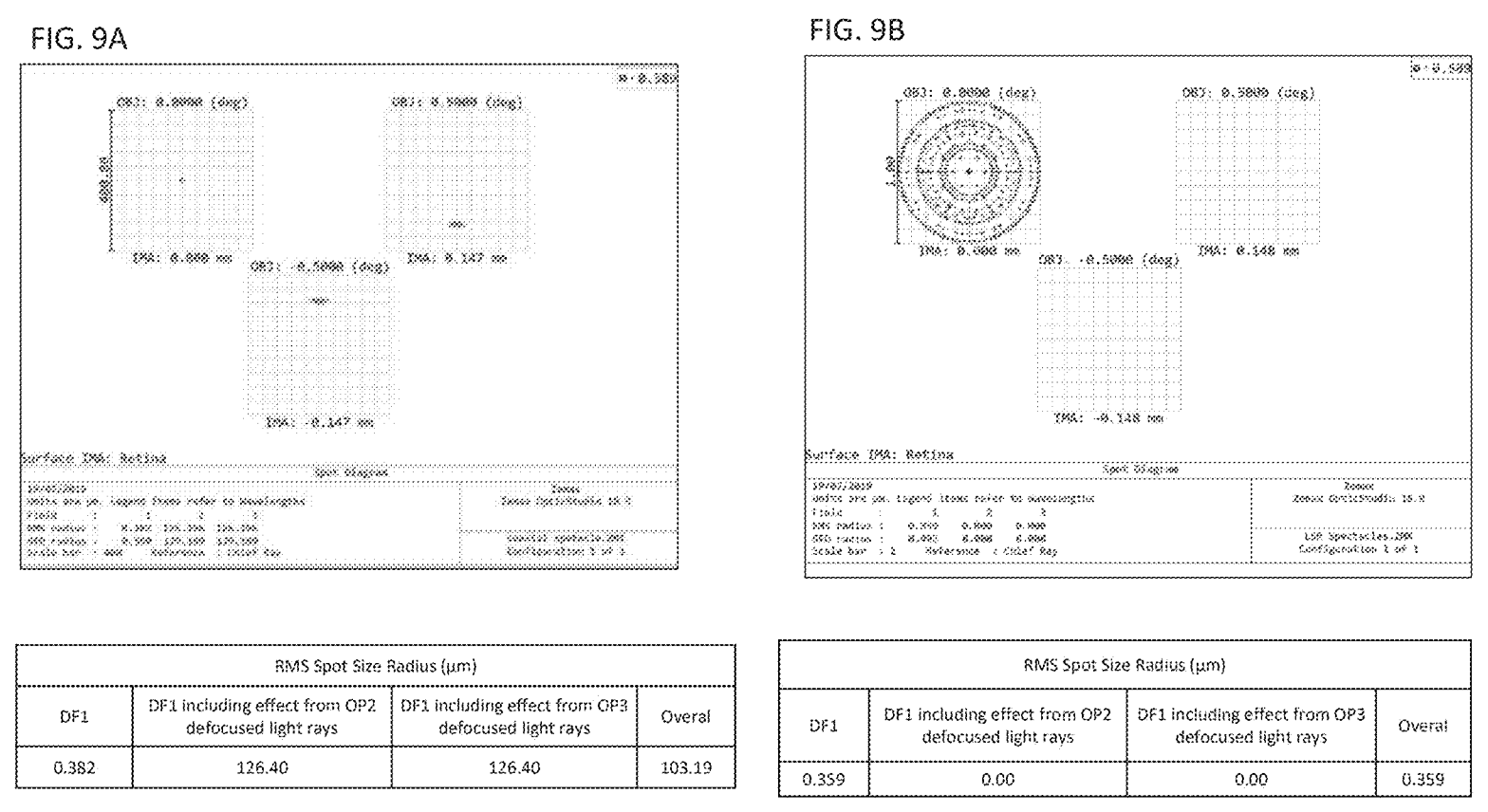

| RMS Spot Size Radius (μm) | | | |
|---|---|---|---|
| DF1 | DF1 including effect from OP2 defocused light rays | DF1 including effect from OP3 defocused light rays | Overal |
| 0.382 | 126.40 | 126.40 | 103.19 |

FIG. 9B

| RMS Spot Size Radius (μm) | | | |
|---|---|---|---|
| DF1 | DF1 including effect from OP2 defocused light rays | DF1 including effect from OP3 defocused light rays | Overal |
| 0.359 | 0.00 | 0.00 | 0.359 |

LSR Value: 0.0 mm
Pupillary zone: 5 mm
1001
1002

OP2
OP1
OP3
Near Focus
NF2
NF1
NF3
Distance Focus
DF2
DF1
DF3

| RMS Spot Size Radius (µm) | | | |
|---|---|---|---|
| DF1 | DF1 including effect from OP2 defocused light rays | DF1 including effect from OP3 defocused light rays | Overall |
| 0.711 | 110.99 | 110.99 | 90.62 |

| RMS Spot Size Radius (µm) | | | |
|---|---|---|---|
| NF1 | NF1 including effect from OP2 defocused light rays | NF1 including effect from OP3 defocused light rays | Overall |
| 0.202 | 44.150 | 44.150 | 36.048 |

The field sampling at distance focus is ±0.50° and near focus is ±0.15°

| RMS Spot Size Radius (µm) | | | |
|---|---|---|---|
| DF1 | DF1 including effect from OP2 defocused light rays | DF1 including effect from OP3 defocused light rays | Overall |
| 0.704 | 0 | 0 | 0.704 |

| RMS Spot Size Radius (µm) | | | |
|---|---|---|---|
| NF1 | NF1 including effect from OP2 defocused light rays | NF1 including effect from OP3 defocused light rays | Overall |
| 0.050 | 0 | 0 | 0.050 |

The field sampling at distance focus is ±0.50° and near focus is ±0.15°

FIG. 15A

| RMS Spot Size Radius (µm) | | | |
|---|---|---|---|
| DF1 | DF1 including effect from OP2 defocused light rays | DF1 including effect from OP3 defocused light rays | Overall |
| 2.157 | 0 | 0 | 2.157 |

The field sampling at distance focus is +/-0.50 degrees

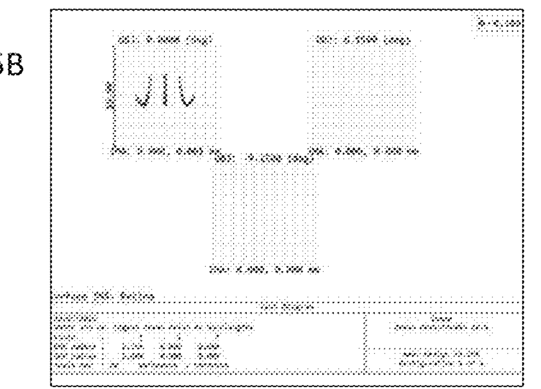

FIG. 15B

| RMS Spot Size Radius (µm) | | | |
|---|---|---|---|
| NF1 | NF1 including effect from OP2 defocused light rays | NF1 including effect from OP3 defocused light rays | Overall |
| 1.796 | 0 | 0 | 1.796 |

The field sampling at distance focus is +/-0.15 degrees

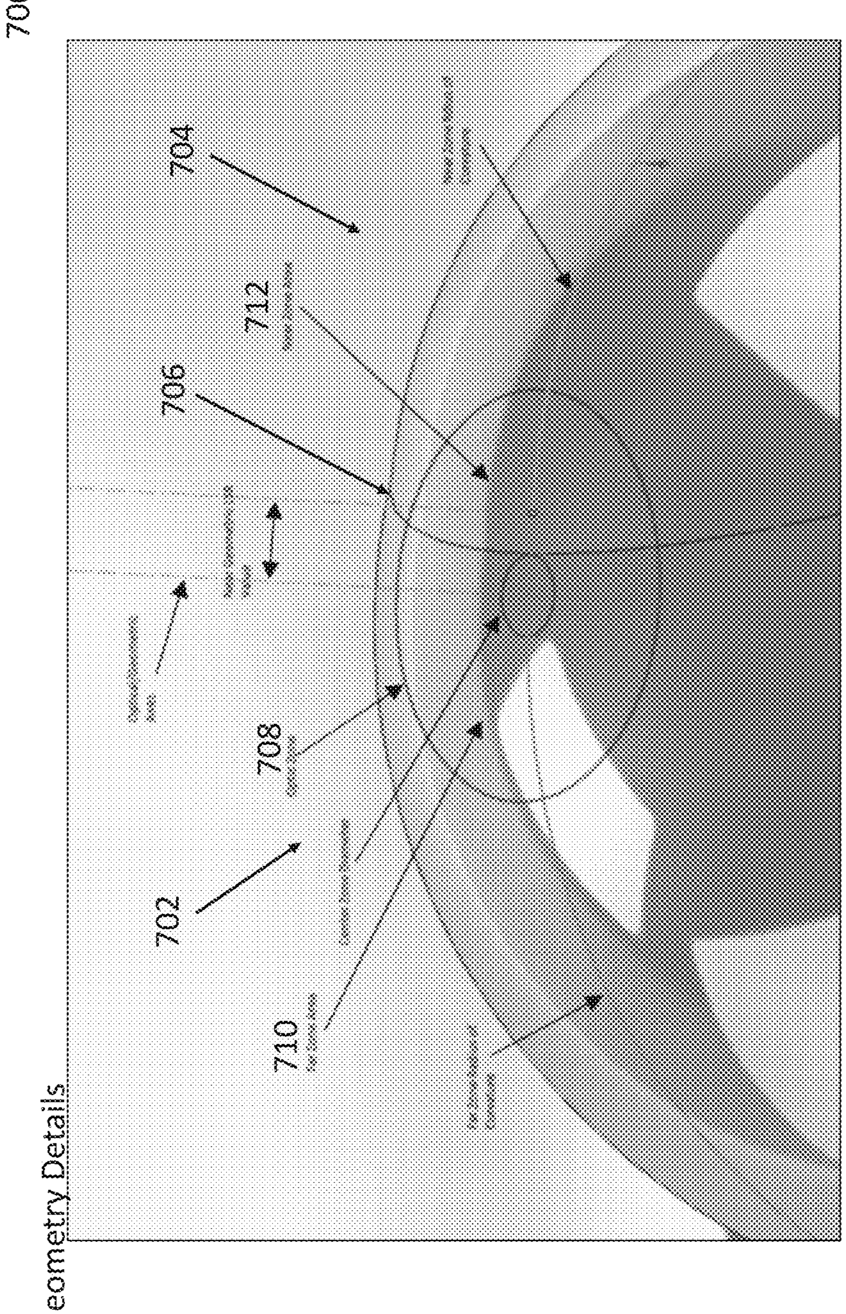
FIG. 16
New Geometry Details

FIG. 17

LSR Value: 0.5 mm

Pupillary zone 5.00 mm

Near Focus

NF3

NF1

NF2

Distance Focus

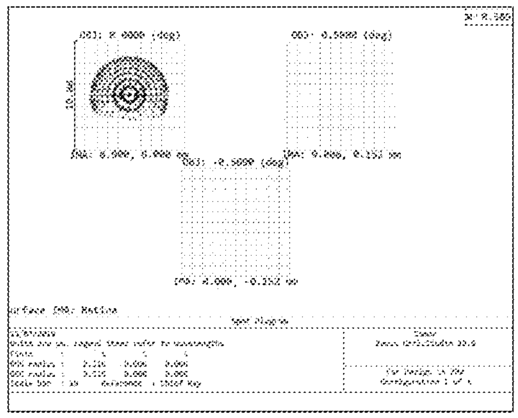

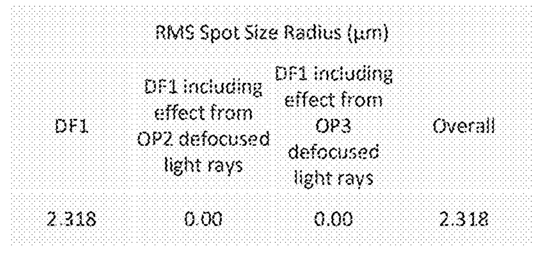

| RMS Spot Size Radius (µm) | | | |
|---|---|---|---|
| DF1 | DF1 including effect from OP2 defocused light rays | DF1 including effect from OP3 defocused light rays | Overall |
| 2.318 | 0.00 | 0.00 | 2.318 |

The field sampling at distance focus is +/-0.50 degrees

FIG. 19B

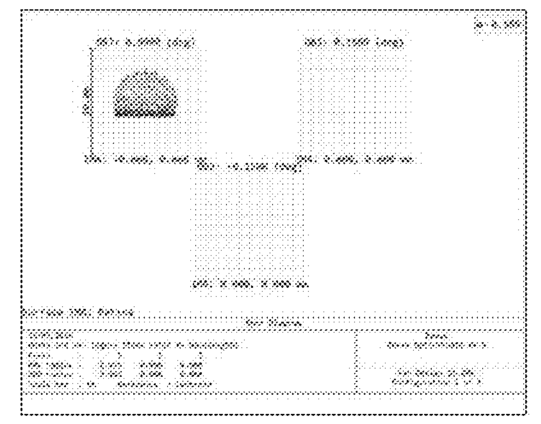

| RMS Spot Size Radius (µm) | | | |
|---|---|---|---|
| NF1 | NF1 including effect from OP2 defocused light rays | NF1 including effect from OP3 defocused light rays | Overall |
| 1.979 | 0.00 | 0.00 | 1.979 |

The field sampling at distance focus is +/-0.15 degrees

LSR Value: 0.25 mm
Pupillary zone : 5.00 mm
2001
2002
5mm
14mm

OP2
OP1
OP3
Distance Focus
Near Focus
DF3
DF1
DF2
NF3
NF1
NF2
LSR 0.25mm

FIG. 22A

| RMS Spot Size Radius (μm) | | | |
|---|---|---|---|
| DF1 | DF1 including effect from OP2 defocused light rays | DF1 including effect from OP3 defocused light rays | Overall |
| 1.926 | 0.00 | 162.60 | 93.88 |

The field sampling at distance focus is +/-0.50 degrees

FIG. 22B

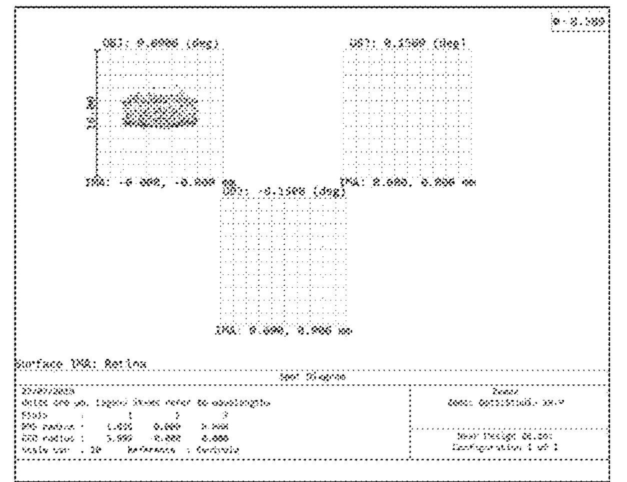

| RMS Spot Size Radius (μm) | | | |
|---|---|---|---|
| NF1 | NF1 including effect from OP2 defocused light rays | NF1 including effect from OP3 defocused light rays | Overall |
| 1.838 | 0.00 | 0.00 | 1.838 |

The field sampling at distance focus is +/-0.15 degrees

Near LSR Value: 0.50 mm
Far LSR Value: 0.250 mm
Pupillary zone : 5.00 mm
2301
2302
Near zone
5mm
14mm OP2
OP1
OP3
Distance Focus
Near Focus
DF3
DF1
DF2
NF3
NF1
NF2

FIG. 25A

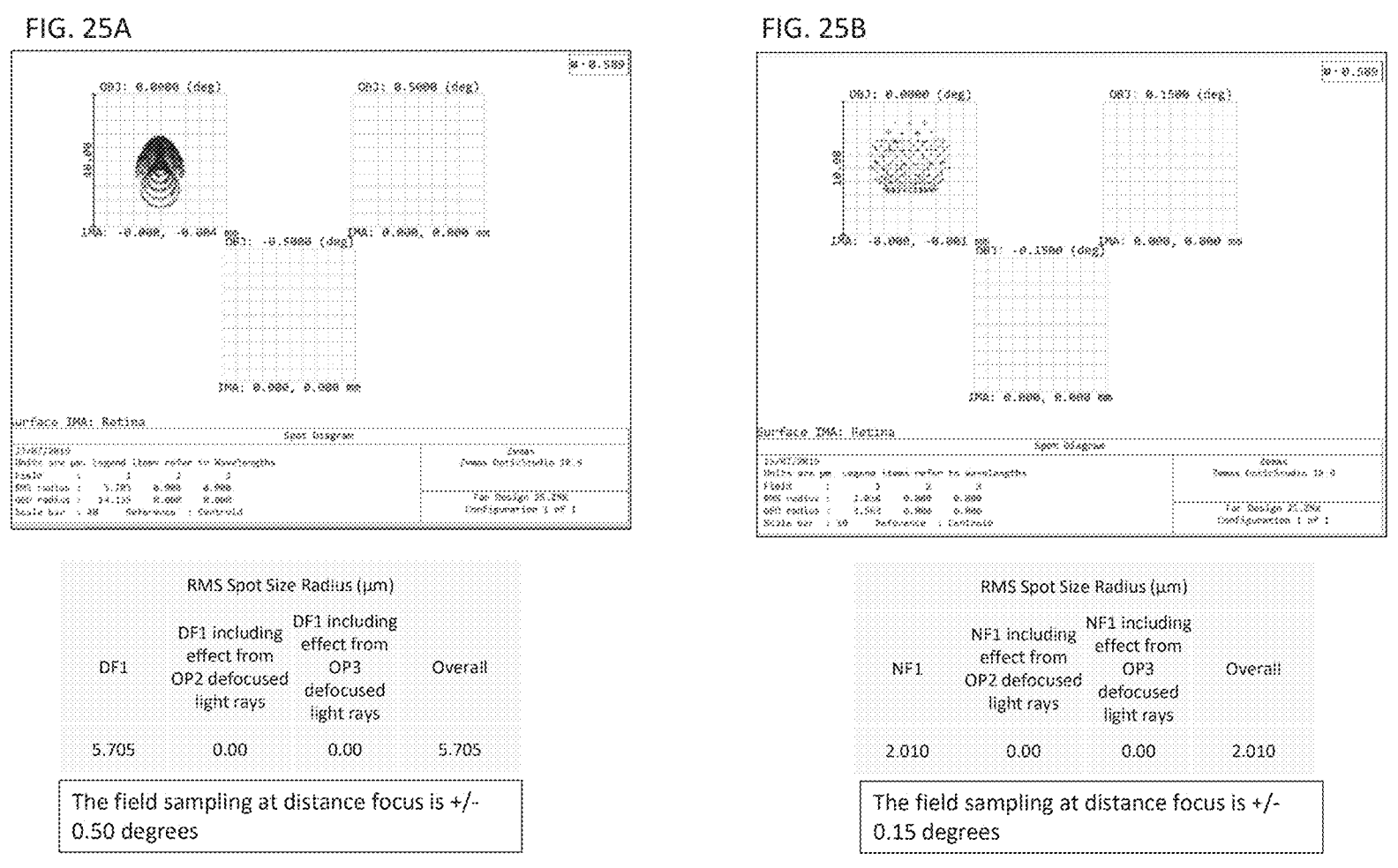

Surface IMA: Retina

Spot Diagram

| RMS Spot Size Radius (µm) | | | |
|---|---|---|---|
| DF1 | DF1 including effect from OP2 defocused light rays | DF1 including effect from OP3 defocused light rays | Overall |
| 5.705 | 0.00 | 0.00 | 5.705 |

The field sampling at distance focus is +/- 0.50 degrees

FIG. 25B

Surface IMA: Retina

Spot Diagram

| RMS Spot Size Radius (µm) | | | |
|---|---|---|---|
| NF1 | NF1 including effect from OP2 defocused light rays | NF1 including effect from OP3 defocused light rays | Overall |
| 2.010 | 0.00 | 0.00 | 2.010 |

The field sampling at distance focus is +/- 0.15 degrees

FIG. 28A

| RMS Spot Size Radius (µm) | | | |
|---|---|---|---|
| DF1 | DF1 including effect from OP2 defocused light rays | DF1 including effect from OP3 defocused light rays | Overall |
| 0.490 | 0.00 | 0.00 | 0.490 |

The field sampling at distance focus is +/-0.50 degrees

FIG. 28B

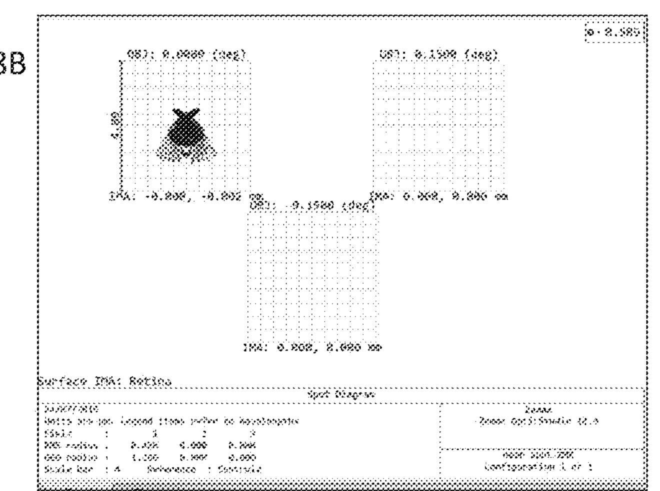

| RMS Spot Size Radius (µm) | | | |
|---|---|---|---|
| NF1 | NF1 including effect from OP2 defocused light rays | NF1 including effect from OP3 defocused light rays | Overall |
| 0.420 | 0.00 | 0.00 | 0.420 |

The field sampling at distance focus is +/-0.15 degrees

Executive Bifocal Spectacle Lens

FIG. 31A

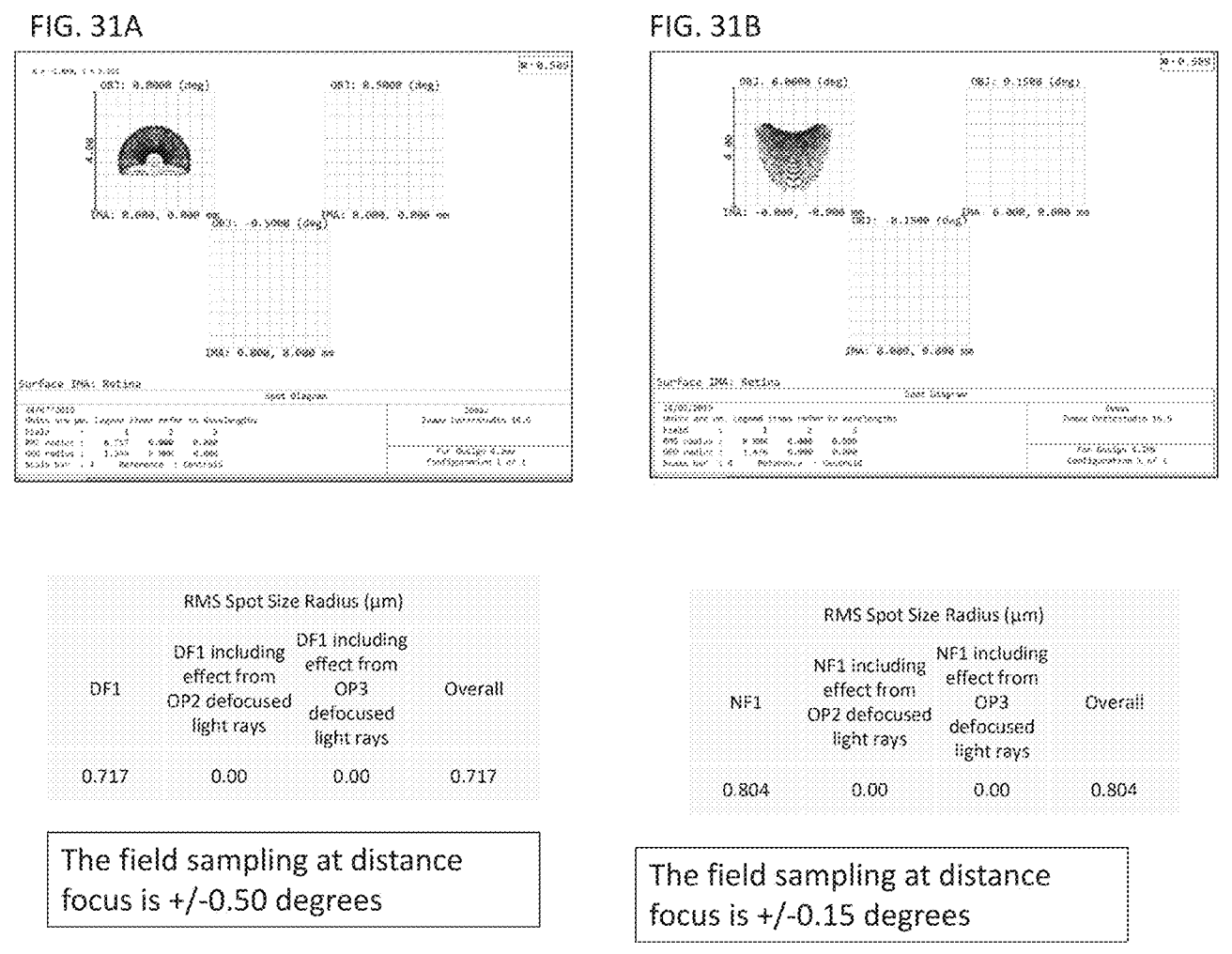

| RMS Spot Size Radius (μm) | | | |
|---|---|---|---|
| DF1 | DF1 including effect from OP2 defocused light rays | DF1 including effect from OP3 defocused light rays | Overall |
| 0.717 | 0.00 | 0.00 | 0.717 |

The field sampling at distance focus is +/-0.50 degrees

FIG. 31B

| RMS Spot Size Radius (μm) | | | |
|---|---|---|---|
| NF1 | NF1 including effect from OP2 defocused light rays | NF1 including effect from OP3 defocused light rays | Overall |
| 0.804 | 0.00 | 0.00 | 0.804 |

The field sampling at distance focus is +/-0.15 degrees

Near LSR Value: 0.25 mm
Distance LSR Value: 0.25
Pupillary zone : 5.00 mm

FIG. 34A

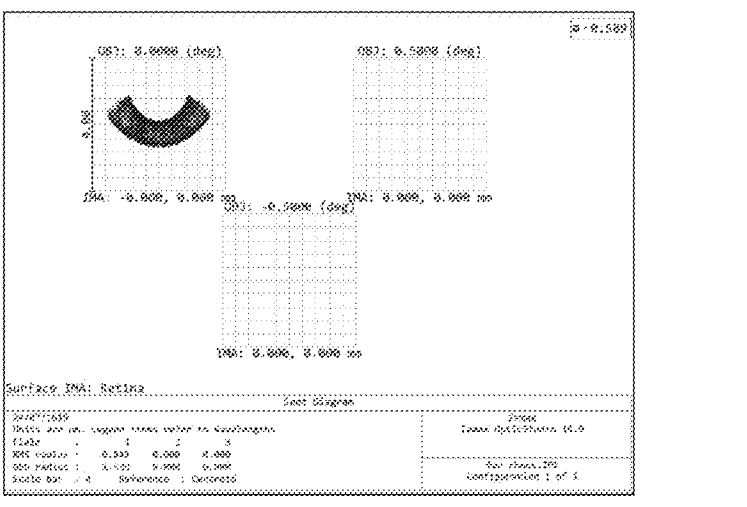

| RMS Spot Size Radius (μm) | | | |
|---|---|---|---|
| DF1 | DF1 including effect from OP2 defocused light rays | DF1 including effect from OP3 defocused light rays | Overall |
| 0.804 | 0.00 | 0.00 | 0.804 |

The field sampling at distance focus is +/-0.50 degrees

FIG. 34B

| RMS Spot Size Radius (μm) | | | |
|---|---|---|---|
| NF1 | NF1 including effect from OP2 defocused light rays | NF1 including effect from OP3 defocused light rays | Overall |
| 1.494 | 0.00 | 0.00 | 1.494 |

The field sampling at distance focus is +/-0.15 degrees

| | [illegible] | [illegible] | [illegible] |
| --- | --- | --- | --- |
| LSR Value before compensation | 0.25 | 0.25 | -0.25 |
| LSR Value after compensation | 0.00 | 0.00 | 0.00 |

FIG. 37A

| RMS Spot Size Radius (µm) | | | |
|---|---|---|---|
| DF1 | DF1 including effect from OP2 defocused light rays | DF1 including effect from OP3 defocused light rays | Overall |
| 5.792 | 0.00 | 0.00 | 5.792 |

The field sampling at distance focus is +/-0.50 degrees

FIG. 37B

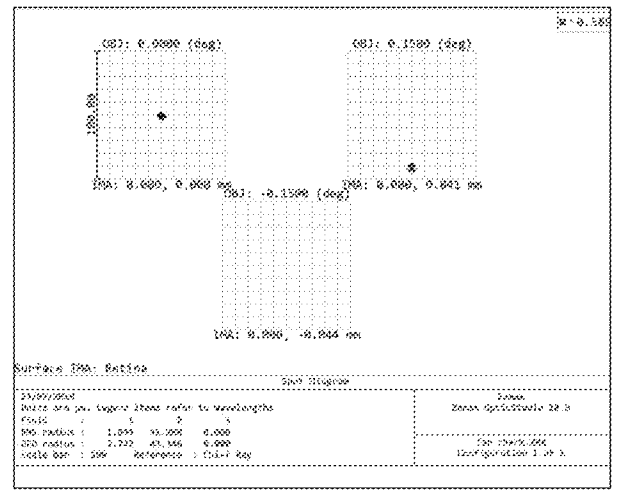

| RMS Spot Size Radius (µm) | | | |
|---|---|---|---|
| NF1 | NF1 including effect from OP2 defocused light rays | NF1 including effect from OP3 defocused light rays | Overall |
| 1.844 | 41.288 | 0.00 | 23.86 |

The field sampling at distance focus is +/-0.15 degrees

FIG. 38: Cylinder free PAL Spectacle lens design
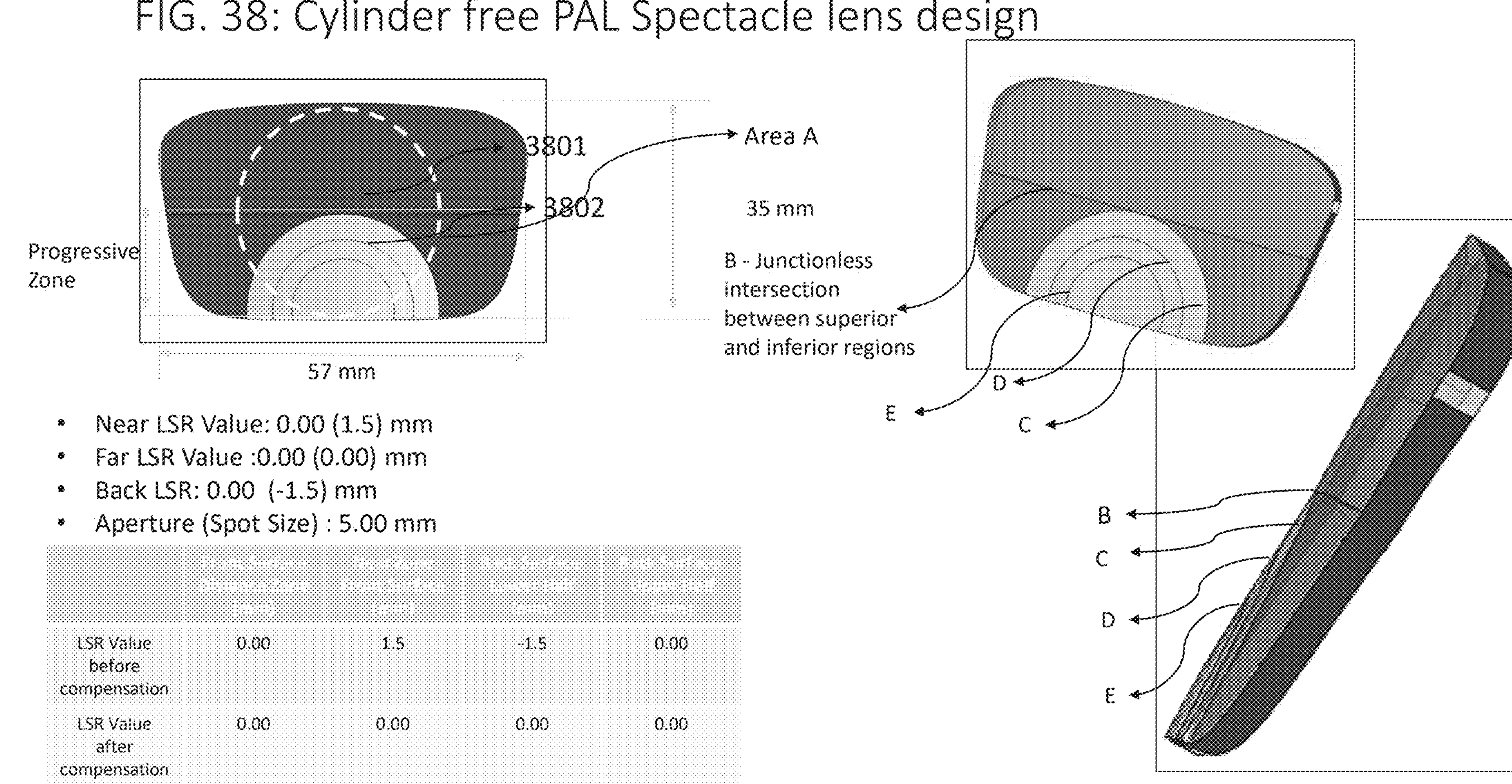
- Near LSR Value: 0.00 (1.5) mm
- Far LSR Value :0.00 (0.00) mm
- Back LSR: 0.00 (-1.5) mm
- Aperture (Spot Size) : 5.00 mm
| | [illegible] | [illegible] | [illegible] | [illegible] |
|---|---|---|---|---|
| LSR Value before compensation | 0.00 | 1.5 | -1.5 | 0.00 |
| LSR Value after compensation | 0.00 | 0.00 | 0.00 | 0.00 |

FIG. 39: Cylinder free PAL Spectacle lens design- More Details

FIG. 40: Cylinder free PAL Spectacle lens design- More Details
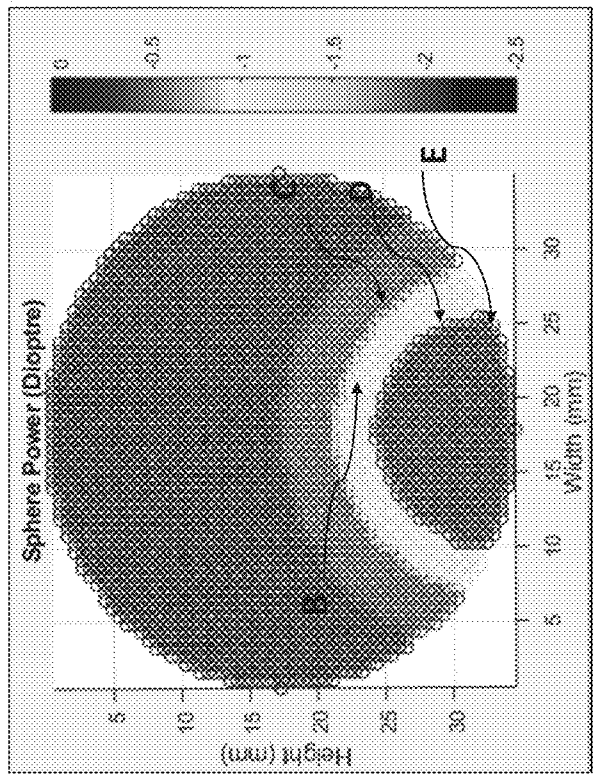
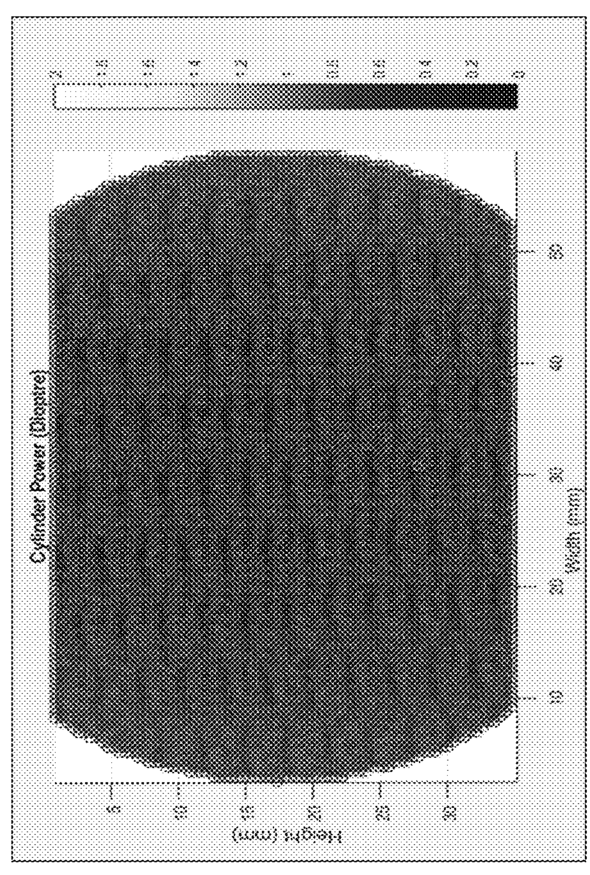

4303
4301e
4302
4301c
4306
4302a
4302
4301d
4301
4300a

More positive power
On-axis power
p, 4302a
4301
4202d
4302c
4302
4302e
m, 4202b
4303
Radial Distance from the center of the lens (mm)
4301
4302
4303

FIG. 44A

Chief Ray Angle; $\theta$ 5
16
12B
10B
6
7
9
8
15
$f_i$
$f_e$
4403
41
4404
4401
4402

Figure 49B:
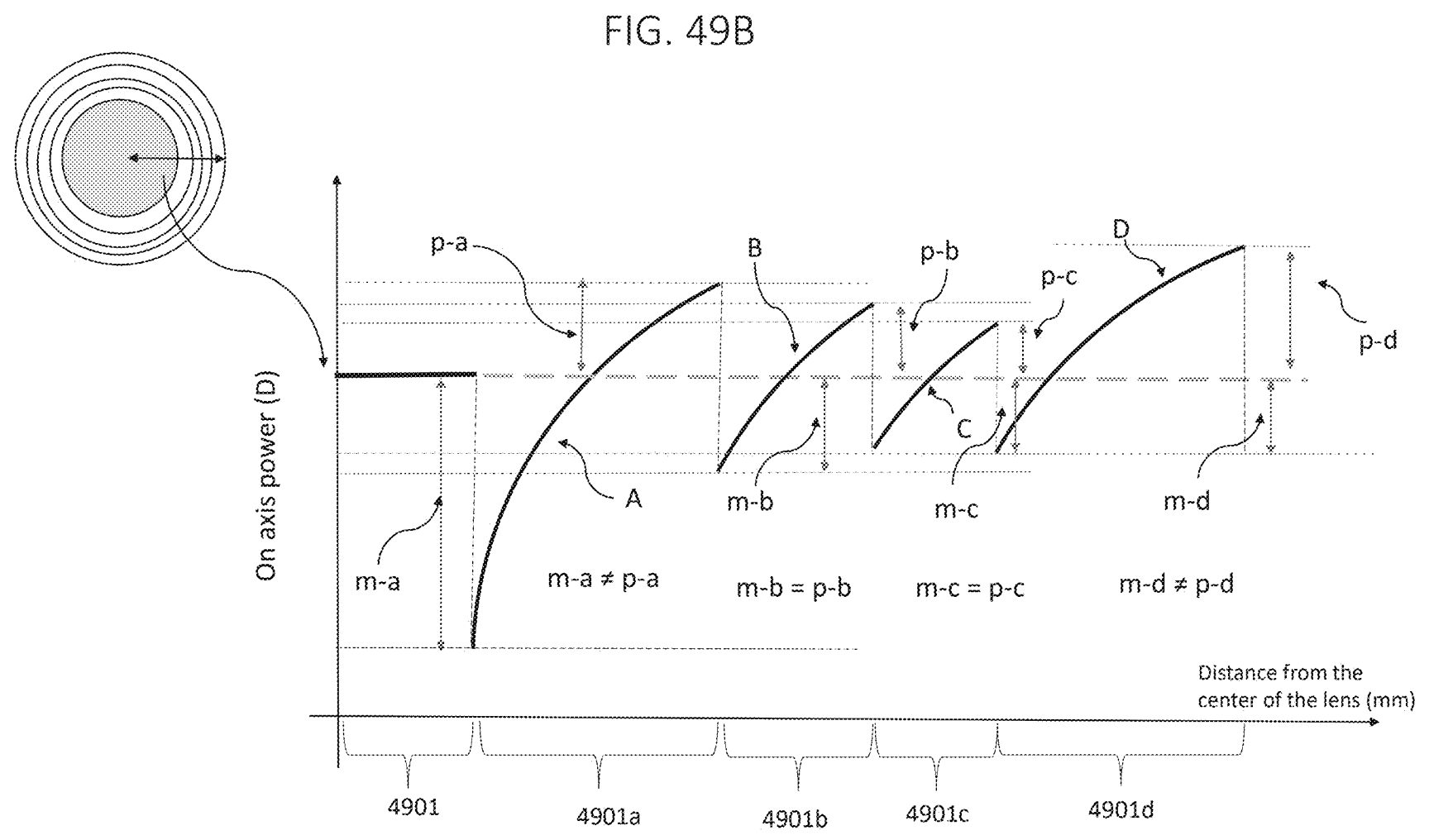

On axis power (D)

Distance from the center of the lens (mm)

p-a p-b p-c p-d m-a m-b m-c m-d

A B C D m-a ≠ p-a m-b = p-b m-c = p-c m-d ≠ p-d 4901 4901a 4901b 4901c 4901d 5000
5001
5001a
5001b
5001c
5002
5002a
5002b
5002c
5003
5004
5006

5121
5122
5123a
5123b
5123c
5124a
5124b
5124c
5 mm
Front Surface
Back Surface
5129
2.3
5 mm
Sagittal Power (Diopters)
X-Pupil
-0.81
-0.404
0
0.404
0.81

| Design | Center Zone | Annular Zone Width | Number of Annular Zones over 5mm |
|---|---|---|---|
| FIG. 44-CL | 3 mm | 1 mm | 2 |
| FIG. 51B-CL | 2 mm | 1 mm | 2.5 |
| CLD | 3 mm | 1 mm | 2 |

OPHTHALMIC LENSES FOR REDUCING, MINIMIZING, AND/OR ELIMINATING INTERFERENCE ON IN-FOCUS IMAGES BY OUT-OF-FOCUS LIGHT

CROSS REFERENCE TO RELATED APPLICATION

This application is the National Phase application of International Application No. PCT/IB2020/057863, filed Aug. 21, 2020, which designates the United States and was published in English, which, claims priority to U.S. Provisional Application No. 62/890,809 filed on Aug. 23, 2019. These applications are herein incorporated by reference in their entirety. This disclosure is also related to International Application No. PCT/AU2017/051173, filed on Oct. 25, 2017, and International Application No. PCT/IB2020/056079, filed on Jun. 26, 2020. Each of these related applications are herein incorporated by reference in their entirety.

TECHNICAL FIELD

This disclosure relates to ophthalmic lenses and more particularly, to ophthalmic lenses for controlling, reducing, minimizing, and/or eliminating interference on in-focus images by out-of-focus images to alter (e.g., improve) the quality of retinal images.

BACKGROUND

The optics of an eye determines whether an image is focused on the retina of an eye. Images that are focused on or near the retina of an eye are typically perceived as good or acceptable image quality. Images that are not focused substantially away from the retina of an eye (may be focused either in front or behind the retina) are typically perceived as being blurred with reduced image quality. Myopia, commonly referred to as shortsightedness, is an optical disorder of the eye and results in on-axis images being focused in front of the retina. On-axis images are those that are substantially in line with the fovea or foveal region of the retina; the region that is capable of the highest visual acuity. Presbyopia, is an optical disorder of the eye wherein the ability of the crystalline lens to accommodate is reduced resulting in blurred vision for distances close to the eye.

Ophthalmic lenses may be designed to correct distance, intermediate and/or near vision by providing one or more foci from one or more optical zones. Ophthalmic lenses with multiple zones (e.g., simultaneous vision lenses) may result in visual compromise because light passing through such lenses result in overlapping images due to focal points from one optical zone interfering with focal points from other optical zones and therefore, resulting in a reduction in the quality and/or contrast of the retinal image.

Accordingly, there is a need for ophthalmic lenses for controlling, reducing, minimizing, and/or eliminating interference, of in-focus light (e.g., an in-focus image) with out-of-focus images to improve image quality. Exemplary embodiments may reduce, substantially reduced, and/or eliminate the effects of optical disorders including one or more of the following: myopia, presbyopia, and/or have other advantages and/or improvements as discussed herein. The present disclosure is directed to solving these and other problems disclosed herein. The present disclosure is also directed to pointing out one or more advantages to using exemplary ophthalmic lenses described herein.

SUMMARY

The present disclosure is directed, at least in part, to overcoming and/or ameliorating one or more of the problems described herein.

The present disclosure is directed, at least in part, to ophthalmic lenses for controlling, the interference of an out-of-focus light with an in-focus image to improve the image quality.

The present disclosure is directed, at least in part, to ophthalmic lenses for controlling the overlap of an out-of-focus image with an in-focus image to extend the depth of focus.

The present disclosure is directed, at least in part, to ophthalmic lenses for controlling the overlap of one or more focal points at a given image plane with focal points of one or more out-of-focus images or rays by separating or displacing the focal points associated with the image at a given image plane with the focal points associated with the one or more out-of-focus images or rays.

The present disclosure is directed, at least in part, to ophthalmic lenses for controlling the overlap of one or more on axis focal points with one or more off-axis light rays to improve the image quality and/or extend the depth of focus.

The present disclosure is directed, at least in part, to ophthalmic lenses for controlling, the overlap of one or more focal points of an in-focus image at a given image plane with one or more focal points of out-of-focus images by separating and/or displacing the one or more focal points associated with the in-focus image at the image plane with the one or more focal points associated with the out-of-focus images using one or more of an optical separation means.

The present disclosure is directed, at least in part, to ophthalmic lenses for controlling, the overlap of one or more focal points of an in-focus image at a given image plane with one or more focal points associated with out-of-focus images by separating and/or displacing the one or more focal points associated with the in-focus image with the focal points associated with the one or more out-of-focus images using one or more laterally separated optics.

The present disclosure is directed, at least in part, to an optical separation means for separating and/or displacing the focal points associated with the in-focus image at a given image plane with the focal points associated with the one or more out-of-focus images or rays utilizing one or more optical surfaces with the optical surface comprising two or more optical elements (for example, sphere, ellipse, conic, asphere or other suitable element including non-spheroidal torus elements such as line, conicroids) wherein the two or more optical elements are placed, shifted, rotated, tilted or displaced relative to one another so that all or some of the two or more optical elements do not share a common optical axis.

The present disclosure is directed, at least in part, to laterally separated optics for separating and/or displacing the focal points associated with the in-focus image at a given image plane with the focal points associated with the one or more out-of-focus images or rays utilizing one or more optical surfaces with the optical surface comprising two or more optical elements (for example, sphere, ellipse, conic, asphere or other suitable element including non-spheroidal torus elements such as line, conicroids) wherein the two or more optical elements are placed, shifted, rotated, tilted or displaced relative to one another so that all or some of the two or more optical elements do not share a common optical axis.

The present disclosure is directed, at least in part, to exemplary devices that are configured, when in use, to separate and/or displace at least one focal point associated with the in-focus image at a given image plane with the focal points associated with the one or more out-of-focus images or rays utilizing one or more optical surfaces with the optical surface comprising two or more optical elements (for example, sphere, ellipse, conic, asphere or other suitable element including non-spheroidal torus elements such as line, conicroids) wherein the two or more optical elements are placed, shifted, rotated, tilted or displaced relative to one another so that all or some of the two or more optical elements do not share a common optical axis.

The present disclosure is directed, at least in part, to ophthalmic lenses for improving the image quality.

The present disclosure is directed, at least in part, to ophthalmic lenses for improving the image contrast.

The present disclosure is directed, at least in part, to ophthalmic lenses for improving the quality of an in-focus image at a given image plane by controlling the overlap of the focal points associated with an in-focus image at the given image plane with the focal points associated with one of more out-of-focus images.

The present disclosure is directed, at least in part, to ophthalmic lenses for improving the quality of an in-focus image at a given image plane by controlling the overlap of the focal points associated with an in-focus image at a given image plane with the focal points associated with one of more out-of-focus images wherein the improvement may be a reduction in RMS spot size of about 1 μm or more (e.g., about 0.8 μm, about 0.9 μm, about 1 μm, about 1.1 μm, about 1.2 μm, about 1.3 μm, about 1.4 μm, about 1.5 μm, about 1.6 μm, about 1.7 μm, about 1.8 μm, or about 1.9 μm).

The present disclosure is directed, at least in part, to ophthalmic lenses comprising one or more optical zones that do not share a common optical axis.

The present disclosure is directed, at least in part, to ophthalmic lenses comprising a plurality of optical zones or segments wherein the optical axis for the plurality of optical zones or segments are independent of one another and do not share a common axis.

The present disclosure is directed, at least in part, to ophthalmic lenses comprising a plurality of optical zones or segments wherein the displacement of the optical axis of the plurality of optical zones or segments may create a prism power.

The present disclosure is directed, at least in part, to ophthalmic lenses comprising a plurality of optical zones or segments wherein the displacement of one optical axis of the plurality of optical zones or segments from one of the other optical axis of the plurality of optical zones or segments creates a prism power about 0.05Δ diopter to about 15 prism diopters (Δ) (e.g., about 0.025Δ, about 0.05Δ, about 0.075Δ, about 0.1Δ, about 0.125Δ, about 0.15Δ, about 0.175Δ, about 0.2Δ, about 0.25Δ, about 0.3Δ, about 0.35Δ, about 0.4Δ, about 0.45Δ, about 0.5Δ, about 0.6Δ, about 0.7Δ, about 0.8×, about 0.9Δ, about 1Δ, about 2Δ, about 3Δ, about 4Δ, about 5Δ, about 6Δ, about 7Δ, about 8Δ, about 9Δ, about 10Δ, about 11Δ, about 12Δ, about 13Δ, about 14Δ, about 15Δ, about 16Δ, about 17Δ, or about 18Δ).

The present disclosure is directed, at least in part, to ophthalmic lenses comprising: a first optical zone defined, at least in part, by a sphere having a first radius and having a first axis, the first optical zone being configured such that, in use with an eye, light passing through the first optical zone is refracted to a first focal point on the first axis; and a second optical zone defined, at least in part, by a sphere having a second radius, different than the first radius and configured such that, in use with the eye, light passing through the second optical zone is refracted to a second focal point (e.g., on a second axis); wherein the second focal point is displaced from the first axis by an amount substantially equal to a center zone diameter of the ophthalmic lens.

The present disclosure is directed, at least in part, to ophthalmic lenses comprising: a plurality of optical zones (e.g., 2, 3, 4, or 5 optical zones) configured such that, in use with an eye, light passing through the plurality of optical zones is refracted to a corresponding plurality of one or more focal points on a corresponding plurality of axes; wherein at least two of the plurality of optical zones do not share a common axis.

The present disclosure is directed, at least in part, to ophthalmic lenses comprising: at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points; wherein the one or more focal points from the at least one second optical zone are not on the first axis.

In some embodiments, the first power may be uniform or may vary in different portions of the first optical zone. In some embodiments, the ophthalmic lens may comprise a third optical zone with a third power. In some embodiments, the third optical zone may be one or more concentric zones proximate to (e.g., surrounding) the central optical zone. In some embodiments, the third optical zone may be a section, meridian or a portion of the lens other than the section, meridian or portion of the lens occupied by the first optical zone and the second optical zone.

In some embodiments, the at least one first optical zone and the at least one second optical zone may define an optic zone of the ophthalmic lens.

In some embodiments, the at least one first optical zone and the at least one second optical zone may occupy a substantial portion (e.g., substantially all) of an optic zone of the ophthalmic lens.

In some embodiments, the at least one first optical zone and the at least one second optical zone may occupy at least 90%, 95%, 98% or 99% of the surface area of an optic zone of the ophthalmic lens.

In some embodiments, the ophthalmic lens may be configured such that, in use with the eye, out-of-focus light associated with the at least one second optical zone does not substantially interfere with focal points associated with the at least one first optical zone.

In some embodiments, the ophthalmic lens may be configured such that, in use with the eye, out-of-focus light associated with the at least one first optical zone does not substantially interfere with focal points associated with the at least one second optical zone.

In some embodiments, the ophthalmic lens may be configured such that, in use with the eye, interference at an in-focus focal point by the out-of-focus light is controlled.

In some embodiments, the at least one first optical zone may comprise a first optical power and the at least one second optical zone comprises one or more second optical powers different from the first optical power.

In some embodiments, the at least one first optical zone may comprise a first optical power and the at least one second optical zone comprises a second optical power relatively more positive than the first optical power.

In some embodiments, the at least one first optical zone may comprise a first optical power and the at least one second optical zone comprises a second optical power relatively less positive than the first optical power.

In some embodiments, the at least one first optical zone may be configured to correct one or more of the following: distance, intermediate and near vision; and/or the at least one second optical zone is configured to correct a different one of distance, intermediate, or near vision.

In some embodiments, the at least one first optical zone may be configured to correct distance vision and the at least one second optical zone is configured to correct near vision.

In some embodiments, the at least one first optical zone in conjunction with the one the one second optical zone is configured to correct one or more of the following: distance, intermediate and near vision.

In some embodiments, the at least one first optical zone may be configured to correct near vision and the at least one second optical zone is configured to correct distance vision.

In some embodiments, the at least one first optical zone may occupy a superior portion of the optic zone and the second optical zone may occupy an inferior portion of the optic zone.

In some embodiments, the first axis may be an axis of symmetry about which the optic zone of the ophthalmic lens is rotationally symmetrical.

In some embodiments, the first axis may be an optical axis of the at least one first optical zone.

In some embodiments, the first focal point may be on the first axis at a first distance from the ophthalmic lens and the second focal point may be at a second distance from the ophthalmic lens, the second distance being different than the first distance and displaced from the first axis.

In some embodiments, the second optical zone may have a second axis associated with the second optical zone, the second axis being displaced from the first axis.

In some embodiments, the lateral separation of the first axis and the second axis on the surface of the ophthalmic lens may be about 0.5 mm (e.g., about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm or about 1 mm). In some embodiments, the lateral separation of the first axis and the second axis on the surface of the ophthalmic lens may be about 0.25 mm, about 0.5 mm, or about 0.75 mm. In some embodiments, the lateral separation of the first axis and the second axis on the surface of the ophthalmic lens may be about 1 mm, about 2 mm, or about 3 mm, about 4 mm, about 5 mm, about 6 mm, about 7 mm, or about 8 mm.

In some embodiments, the lateral separation of the first axis and the second axis on the surface of the ophthalmic lens may be less than about 0.5 mm (e.g., less than about 50 um, about 60 um, about 70 um, about 80 um, about 90 um, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, or about 0.6 mm). In some embodiments, the lateral separation of the first axis and the second axis on the surface of the ophthalmic lens may be less than about 0.1 mm about 0.25 mm, or about 0.5 mm.

In some embodiments, the lateral separation of the first axis and the second axis on the surface of the ophthalmic lens may be more than about 50 um (e.g., more than about 50 um, about 60 um, about 70 um, about 80 um, about 90 um, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, or about 0.6 mm). In some embodiments, the lateral separation of the first axis and the second axis on the surface of the ophthalmic lens may be more than about 0.1 mm about 0.25 mm, or about 0.5 mm.

In some embodiments, the at least one first optical zone may have a substantially circular shape.

In some embodiments, the at least one first optical zone is centrally located on the ophthalmic lens.

In some embodiments, the at least one first optical zone may have a substantially circular shape centrally located on the ophthalmic lens and the at least one second optical zone has a substantially annular shape surrounding the at least one first optical zone.

In some embodiments, at least a portion of the at least one first optical zone may have a substantially circular shape centrally located on the ophthalmic lens and at least a portion of the at least one second optical zone has a substantially annular shape surrounding the at least one first optical zone.

In some embodiments, the at least one first optical zone may comprise a first portion that has a substantially circular shape centrally located on the ophthalmic lens and a second portion that has a substantially annular shape surrounding the first portion.

In some embodiments, the at least one second optical zone may comprise a first portion that has a substantially annular shape surrounding the at least one first optical zone and a second portion that has a substantially annular shape surrounding the first portion.

In some embodiments, the at least one first optical zone and the at least one second optical zone may be concentric (e.g., substantially concentric, and/or partially concentric).

In some embodiments, the at least one first optical zone and the at least one second optical zone may be substantially concentric but do not share a common axis.

In some embodiments, the at least one first optical zone and/or the at least one second optical zone may be rotationally symmetric about the first axis.

In some embodiments, the at least one first optical zone may directly contact the at least one second optical zone.

In some embodiments, a blending zone may be located between the at least one first optical zone and the at least one second optical zone.

In some embodiments, the at least one first optical zone may occupy more than 50% (e.g., about 55%, 60%, 65%, 70%, or 75%) of the surface area of the optic zone of the ophthalmic lens.

In some embodiments, the at least one first optical zone may occupy less than 50% (e.g., about 45%, 40%, 35%, 30%, or 25%) of the surface area of the optic zone of the ophthalmic lens.

In some embodiments, the at least one first optical zone may occupy about 60% (e.g., about 55%, 56%, 57%, 58%, 59%, 60%, 61%, 62%, 63%, 64%, or 65%) of the surface area of the optic zone of the ophthalmic lens.

In some embodiments, the at least one first optical zone may occupy about 40% (e.g., about 35%, 36%, 37%, 38%, 39%, 40%, 41%, 42%, 43%, 44%, or 45%) of the surface area of the optic zone of the ophthalmic lens.

In some embodiments, the at least one first optical zone may occupy less than about 75% (e.g., about 55%, 60%, 65%, 70%, or 75%) of the surface area of the optic zone of the ophthalmic lens.

In some embodiments, the at least one first optical zone may occupy more than about 25% (e.g., about 25%, 30%, 35%, 40%, or 45%) of the surface area of the optic zone of the ophthalmic lens.

In some embodiments, the at least one first optical zone may be defined, at least in part, by a sphere having a first radius and/or the at least one second optical zone is defined, at least in part, by a sphere having a second radius, different than the first radius.

In some embodiments, the at least one first optical zone may be defined, at least in part, by a sphere having a first radius and/or the at least one second optical zone is defined, at least in part, by a sphere having a second radius, smaller than the first radius.

In some embodiments, the at least one first optical zone may be defined, at least in part, by a sphere having a first radius and/or the at least one second optical zone is defined, at least in part, by a sphere having a second radius, larger than the first radius.

In some embodiments, the at least one first optical zone may be substantially circular in shape and has a diameter of about 3 mm (e.g., in some embodiments, the diameter may be about 2 mm, 2.5 mm, 3 mm, 3.5 mm, 4 mm, 2-4 mm, 2-3 mm, 3-4 mm, less than 4 mmm, less than 3.5 mm, and/or less the 3 mm).

In some embodiments, the at least one second optical zone may be substantially annular in shape and has an inner diameter of about 2 mm (e.g., in some embodiments, the inner diameter may be about 2 mm, 2.5 mm, 3 mm, 3.5 mm, 4 mm, 2-4 mm, 2-3 mm, 3-4 mm, less than 4 mm, less than 3.5 mm, and/or less than 3 mm) and an outer diameter of about 7 mm (e.g., in some embodiments, the outer diameter may be about 3 mm, 4 mm, 5 mm, 5.5 mm, 6 mm, 6.5 mm, 7 mm, 7.5 mm, 8 mm, 5-8 mm, 6-7 mm, 6-8 mm, less than 8 mmm, less than 7.5 mm, and/or less than 7 mm).

In some embodiments, the at least one first optical zone may be substantially circular in shape and the at least one second optical zone is substantially annular in shape and an inner diameter of the at least one second optical zone is substantially equal to the diameter of the at least one first optical zone.

In some embodiments, the position of the second focal point may be determined, at least in part, by reducing and/or eliminating the tilt of the front surface of the second optical zone relative to the radius of curvature of the first optical zone.

In some embodiments, the second optical zone may be configured such that, in use with the eye, the light passing through the at least one second optical zone is refracted to multiple (e.g., 1, 2, 3, 4, 5, 6, 7, 8, 9, 10, 11, 12, 13, 14, 15, or 16) focal points, not on the first axis.

The present disclosure is directed, at least in part, to ophthalmic lenses having an extended depth of focus.

The present disclosure is directed, at least in part, to ophthalmic lenses comprising at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points positioned off-axis relative to the first focal point and on at least one focal plane different than a focal plane corresponding to the first focal point; wherein the at least one second optical zone is configured such that the light extending beyond the one or more focal points provides extended depth of focus.

The present disclosure is directed, at least in part, to ophthalmic lenses comprising at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points positioned off-axis relative to the first focal point and on at least one focal plane different than a focal plane corresponding to the first focal point; wherein the at least one first optical zone is configured such that first focal point is positioned in front of a retinal plane; and wherein the at least one second optical zone is configured such that the light extending beyond the one or more focal points in conjunction with the light refracted to the first focal point provides extended depth of focus.

The present disclosure is directed, at least in part, to ophthalmic lenses comprising at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points positioned off-axis relative to the first focal point and on at least one focal plane different than a focal plane corresponding to the first focal point; wherein the at least one first optical zone is configured such that first focal point is positioned in front of a retinal plane; and wherein the at least one second optical zone is configured such that the light extending beyond the one or more focal points in conjunction with the light refracted to the first focal point provides extended depth of focus extending from the retinal image plane to an anterior plane positioned in front of the first focal point at a location that results in the first focal point being substantially equidistant from the anterior plane and the retinal plane.

The present disclosure is directed, at least in part, to ophthalmic lenses comprising at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points positioned off-axis relative to the first focal point and on at least one focal plane different than a focal plane corresponding to the first focal point; wherein the at least one first optical zone is configured such that first focal point is positioned in front of a retinal plane; and wherein the at least one second optical zone is configured such that the light extending beyond the one or more focal points in conjunction with the light refracted to the first focal point provides extended depth of focus located entirely within an eye.

In some embodiments, the at least one first optical zone has a substantially circular shape and centrally located on the ophthalmic lens and the at least one second optical zone may have a substantially annular shape surrounding the at least one first optical zone.

In some embodiments, the at least one first optical zone and the at least one second optical zone may be concentric.

In some embodiments, the one or more focal points positioned off-axis relative to the first focal point may comprise a finite number of focal points (e.g., 2, 3, 4, 5, 6, 7, 8, 9, 10, 11, 12, 13, 14, 15, 16, 180, 360, or 720 focal points).

In some embodiments, the one or more focal points positioned off-axis relative to the first focal point comprise an infinite number of focal points.

In some embodiments, the one or more focal points positioned off-axis relative to the first focal point may be positioned on at least 2 focal planes (e.g., at least 2, 3, 4, or 5 focal planes).

In some embodiments, the quantity and position of the one or more focal points may be determined based at least in part on any combination of one or more of a width of the at least one second optical zone, a curvature of the at least one second optical zone, a location of the at least one second optical zone, a base power of the at least one second optical zone, and/or a lateral separation value of the at least one second optical zone.

In some embodiments, the depth of focus provided by the ophthalmic lens may be determined based at least in part on any combination of one or more of a width of the at least one second optical zone, a curvature of the at least one second optical zone, a location of the at least one second optical zone, a base power of the at least one second optical zone, a lateral separation value of the at least one second optical zone, and/or the m and p components.

In some embodiments, the at least one second optical zone may have a substantially annular shape with a lateral separation value of between 0.2 to 1 mm on the surface of the lens (e.g., the lateral separation on the surface of the lens may be about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm or about 1 mm).

In some embodiments, the at least one second optical zone may have a substantially annular shape with a lateral separation value of between 0.2 to 1 mm on the surface of the lens (e.g., the lateral separation on the surface of the lens may be less than about 50 um, 60 um, 70 um, 80 um, 90 um, 0.1 mm, 0.15 mm, 0.2 mm, 0.25 mm, 0.3 mm, 0.35 mm, 0.4 mm, 0.45 mm, 0.5 mm, 0.55 mm, and/or 0.6 mm).

In some embodiments, the at least one second optical zone may have a substantially annular shape with a lateral separation value of between 0.2 to 1 mm on the surface of the lens (e.g., the lateral separation on the surface of the lens may be more than about 50 um, 60 um, 70 um, 80 um, 90 um, 0.1 mm, 0.15 mm, 0.2 mm, 0.25 mm, 0.3 mm, 0.35 mm, 0.4 mm, 0.45 mm, 0.5 mm, 0.55 mm, and/or 0.6 mm).

In some embodiments, the at least one focal plane may be in front of, behind or in substantially the same plane as the first focal point.

In some embodiments, the rays that extend beyond the at least one focal planes may also form a depth of focus behind and in front of the first focal point.

In some embodiments, the ratio of the amount of depth of focus in front of the first focal point to the amount of the depth of focus behind the first focal point may be about 100:0 (entirely in front of the first focal point), 90:10, 80:20, 75:25, 70:30, 60:40, 50:50 (equally in front of and behind the first focal point), 40:60, 30:70, 25:75, 20:80, 10:90, and/or 0:100 (entirely behind the first focal point).

In some embodiments, the at least one second zone cross-section, in two dimensions, may have a focal length that is independent of the remaining portions of the ophthalmic lens.

In some embodiments, the at least one second zone may be created by adjusting the curvature of the base lens on at least one of a front surface of the ophthalmic lens and/or a back surface of the ophthalmic lens.

In some embodiments, the at least one second zone may be created by adjusting the curvature of the base lens on the front surface of the ophthalmic lens to create one of a plus optical zone or a minus optical zone.

In some embodiments, the at least one second zone may be created by adjusting the curvature of the base lens on the back surface of the ophthalmic lens to create one of a plus optical zone or a minus optical zone.

In some embodiments, the at least one second optical zone may have a substantially annular shape that includes a tilted curvature to influence (e.g., shift) the depth of focus.

In some embodiments, the at least one second optical zone may have a substantially annular shape comprising multiple curve infusions (e.g., 2, 3, 4, 5, 6, 7, 8, 9, and/or 10 curve infusions) that have the same optical properties or different optical properties.

In some embodiments, the at least one second optical zone may have a substantially annular shape comprising multiple conjoined curvatures (e.g., 2, 3, 4, 5, 6, 7, 8, 9, and/or 10 conjoined curvatures).

In some embodiments, the at least one second optical zone may have a substantially annular shape created by replacing at least one (or both) surface curvatures of the lens with a line (e.g., a surface with no, or substantially no, curvature).

In some embodiments, the depth of focus provided by the ophthalmic lens and/or the annular zone may range from about 0.25 D to 5 D (e.g., about 0.25 D, 0.5 D, 0.75 D, 1 D, 1.25 D, 1.5 D, 1.75 D, 2 D, 2.25 D, 2.5 D, 2.75 D, 3 D, 3.25 D, 3.5 D, 3.75 D, 4 D, 4.25 D, 4.5 D, 4.75 D, and/or 5 D).

In some embodiments, the ophthalmic lens may be configured to be used to slow, reduce or arrest the progression of myopia of an eye.

In some embodiments, the ophthalmic lens may be configured to be used for the correction of myopia.

In some embodiments, the ophthalmic lens may be configured to be used to correct presbyopia.

In some embodiments, the ophthalmic lens may be a simultaneous vision lens.

In some embodiments, the ophthalmic lens may be a segmented vision lens and/or a progressive additional multifocal (PAL) lens.

In some embodiments, the ophthalmic lens may be one or more of the following: a spectacle lens, a contact lens, a corneal onlay a corneal inlay, and an anterior or posterior chamber intraocular lens.

Other features and advantages of the subject matter described herein will be apparent from the description and drawings, and from the claims.

BRIEF DESCRIPTION OF THE DRAWINGS

Aspects of the embodiments described herein may be understood from the following detailed description when read with the accompanying figures.

FIGS. 3A and 3B are schematic drawings showing spot diagrams of the focal point, DF1, of object point OP1 formed at the retinal plane by the ophthalmic lenses of FIGS. 1A and 1B.

FIGS. 6A and 6B are schematic drawings showing spot diagrams and RMS values of the focal point, DF1, of object point OP1 formed at the retinal plane by the ophthalmic lenses of FIGS. 4A and 4B in accordance with certain embodiments.

FIGS. 9A and 9B are schematic drawings showing spot diagrams and RMS values of the focal point, DF1, of object point OP1 formed at the retinal plane by the ophthalmic lenses of FIGS. 7A and 7B in accordance with certain embodiments.

FIGS. 15A and 15B are schematic drawings showing spot diagrams and RMS values of the focal point, DF1 and NF1, of object point OP1 formed at the retinal plane by the ophthalmic lens of FIG. 13 in accordance with certain embodiments.

FIG. 16 is a schematic drawing illustrating an exemplary design of an ophthalmic lens using spherical geometry in accordance with certain embodiments.

FIG. 17 is a schematic drawing showing a plan view of an ophthalmic lens (e.g., soft bifocal contact lens) comprising laterally separated optics for distance and near optical zones in accordance with certain embodiments.

FIG. 18 is a schematic drawing showing ray tracing of a distance object and a near object imaged through the ophthalmic lenses of FIG. 17 in accordance with certain embodiments.

FIGS. 19A and 19B are schematic drawings showing spot diagrams and RMS values of the focal point, DF1 and NF1, of object point OP1 formed at the retinal plane by the ophthalmic lens of FIG. 17 in accordance with certain embodiments.

FIGS. 22A and 22B are schematic drawings showing spot diagrams and RMS values of the focal point, DF1 and NF1, of object point OP1 formed at the retinal plane by the ophthalmic lens of FIG. 20 in accordance with certain embodiments.

FIGS. 25A and 25B are schematic drawings showing spot diagrams and RMS values of the focal point, DF1 and NF1, of object point OP1 formed at the retinal plane by the ophthalmic lens of FIG. 23 in accordance with certain embodiments.

FIGS. 28A and 28B are schematic drawings showing spot diagrams and RMS values of the focal point, DF1 and NF1, of object point OP1 formed at the retinal plane by the ophthalmic lens of FIG. 26 in accordance with certain embodiments.

FIGS. 31A and 31B are schematic drawings showing spot diagrams and RMS values of the focal point, DF1 and NF1, of object point OP1 formed at the retinal plane by the ophthalmic lens of FIG. 29B in accordance with certain embodiments.

FIGS. 34A and 34B are schematic drawings showing spot diagrams and RMS values of the focal point, DF1 and NF1, of object point OP1 formed at the retinal plane by the ophthalmic lens of FIG. 32 in accordance with certain embodiments.

FIGS. 37A and 38B are schematic drawings showing spot diagrams and RMS values of the focal point, DF1 and NF1, of object point OP1 formed at the retinal plane by the ophthalmic lens of FIG. 35 in accordance with certain embodiments.

FIG. 38 is a schematic diagram of a progressive addition (PAL) spectacle lens, according certain embodiments.

FIG. 39 is a geometric diagram showing more details of the front surface used to form the example progressive addition spectacle lens (PAL) shown in FIG. 38 in accordance with certain embodiments.

FIG. 40 details the power maps of the PAL spectacle lens design shown in FIG. 39 in accordance with certain embodiments.

FIGS. 44A and 44B are schematic diagrams illustrating an ophthalmic lens incorporating a central optical zone surrounded by an annular zone to create an off-axis focal plane and a depth of focus in accordance with certain embodiments.

FIGS. 49A and 49B are schematic diagrams showing an ophthalmic lens incorporating a central optical zone surrounded by an annular zone to create an off-axis focal plane and a depth of focus in accordance with certain embodiments.

DETAILED DESCRIPTION

Figures 1A, 1B, 2A, 2B:
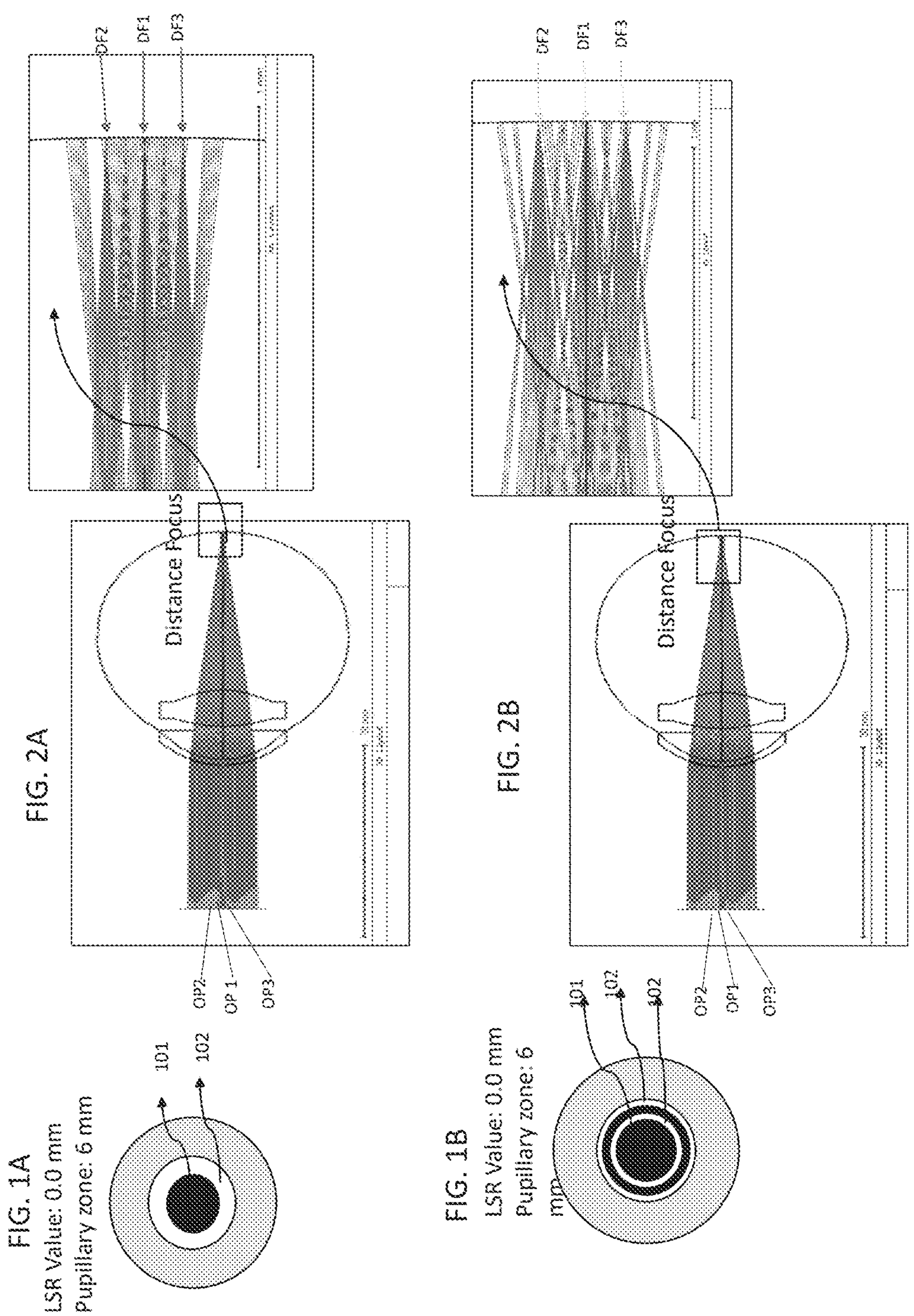
FIGS. 1A and 1B are schematic drawings showing a plan view of dual focus ophthalmic lenses incorporating a central vision correction zone surrounded by zone(s) powered to create myopic defocus for myopia control.
FIGS. 2A and 2B are schematic drawings showing ray tracing of a distance object imaged through the ophthalmic lenses of FIGS. 1A and 1B.

The following disclosure provides many different embodiments, or examples, for implementing different features of the provided subject matter. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

The subject headings used in the detailed description are included for the ease of reference of the reader and should not be used to limit the subject matter found throughout the disclosure or the claims. The subject headings should not be used in construing the scope of the claims or the claim limitations.

The terms “about” as used in this disclosure is to be understood to be interchangeable with the term approximate or approximately.

The term “comprise” and its derivatives (e.g., comprises, comprising) as used in this specification is to be taken to be inclusive of features to which it refers, and is not meant to exclude the presence of additional features unless otherwise stated or implied.

The term “displaced” or “separated” or “laterally separated” as used in this disclosure with reference to two or more optical axes, means that the two or more optical axes or light rays related to optical axes are not substantially coincident and/or do not substantially lie on a common axis but may be parallel, skewed, tilted, or combinations thereof with respect to one another. Additionally, the term “displaced” or “separated” or “laterally separated” as used in this disclosure also means that focal points from the one or more optical zones may be separated from focal points from other one or more optical zones or optical axes of the one or more other optical zones by a distance that is at least one of lateral, vertical, superior, inferior, other angular direction relative to one another, or combinations thereof.

The term “controlled” or “controlling” as used in this disclosure means varying or modifying or reducing the overlap of one or more focal points of an in-focus image at the retina with focal points of one or more out-of-focus images.

The term "interfere" or "interference" as used in this disclosure with reference to light and/or images means at least a portion of the light, at least a portion of the light rays, one or more of the focal points from different optical zones are interfering, overlapping, overlay, conflict, co-occurrence, overlie one another, or combinations thereof.

The term "light quality" or "image quality" as used in this disclosure refers to the performance of the ophthalmic lens as may be determined with, for example, a reduction in root mean square (RMS) spot size, contrast, subjective visual performance measures such as haloes, ghosting and/or combinations thereof. Other suitable ways to determine performance of the ophthalmic lens may also be used.

The term "depth of focus" or "extended depth of focus" as used in this disclosure refers to the distance or range either in front of and/or behind the image plane within which one or more images may be placed/positioned/focused with no substantial reduction in the image quality to the system (such as a living eye or a model eye).

The term "ophthalmic lens" as used in this disclosure is intended to include one or more of the following: a spectacle lens, a contact lens, a film, a sheet, a corneal onlay, a corneal inlay, an intraocular lens, an anterior chamber lens, a lens used to reshape the cornea and a clip-on feature configured to be attached to the spectacle lens.

The term "spectacle lens" as used in this disclosure is intended to include a lens blank, a finished or substantially finished spectacle lens.

The term "out-of-focus" image or light as used in this disclosure is intended to represent an image that appears blurred to a particular user and has a focus that lies substantially at a plane other than the retina.

The term "in-focus" image as used in this disclosure is intended to represent an image that appears clear, substantially clear or suitably clear to a particular user.

The term "optical axis" as used in this disclosure means an optical axis of one or more of the following: a lens, an optical zone, and an optical zone segment.

As discussed in more detail below with respect to the various examples, ophthalmic lenses (e.g., simultaneous vision lenses) are configured to correct combinations of one or more of the following: distance, intermediate, and near vision. In the case of simultaneous vision ophthalmic lenses, the designs provide a plurality of foci corresponding to a plurality of optical zones that share a common axis. In such designs, light passing through the ophthalmic lens may be shared between the plurality of optical zones and, as a result, the focal points from one optical zone may be overlapped by defocused images from the other optical zones—causing interference of in-focus images by out-of-focus images. This may result in a reduction in the image quality (e.g., contrast, sharpness) of the focused image.

An example of a simultaneous vision ophthalmic lens is a distance center bifocal lens (e.g., a contact lens for presbyopia). Most commonly, with such a lens, the lens design may have a central optic zone powered to correct the distance refractive error of the presbyopic eye and may be surrounded by one or more annular or concentric zones with alternate zones powered to correct the refractive error at near. In some other designs, the bifocal lens may be a center near lens, wherein, the design may have a central optic zone powered to correct near refractive error and may be surrounded by one or more annular or concentric zones with alternate concentric zones powered to correct distance refractive error. Commonly, the optical zones are configured to be concentric and coaxial such that the focal points from the plurality of optical zones may fall on the common axis of symmetry of the ophthalmic lens.

Considering the example of a distance center bifocal lens, when viewing distant objects, the ophthalmic lens may provide an in-focus image resulting from light rays refracted by the distance powered optical zone while simultaneously producing one or more out-of-focus images resulting from rays refracted by the one or more concentric near powered optical zones. This may result in the out-of-focus images interfering with the in-focus image, and reducing the image quality (e.g., contrast and/or sharpness of the image). Similarly, when viewing near objects, the ophthalmic lens may provide an in-focus image resulting from rays refracted by the one or more near powered optical zones while simultaneously, or substantially simultaneously, producing an out-of-focus image resulting from light rays refracted by the one or more distance powered optical zones that interfere with the in-focus image, thus reducing the image quality (e.g., contrast and/or sharpness of the image).

FIGS. 1A and 1B are schematic drawings showing a plan view of dual focus ophthalmic lenses incorporating a central vision correction zone 101 surrounded by zone(s) 102 powered to create myopic defocus for myopia control. The dual focus soft contact lenses in FIGS. 1A and 1B incorporate a central vision correction zone 101 surrounded by zones powered to create myopic defocus for myopia control. FIG. 1A comprises a single ring of myopic defocus 102 (e.g., relatively more positively powered compared to the central vision correction zone 101) power and FIG. 1B comprises two rings (annuli) of myopic defocus power (102) separated by a zone 101 that corrects for the distance refractive error. In both lenses the vision correction zones are coaxial with the myopic defocus zones and incorporate, for example, +2.5 D of myopic defocus in the annular zone(s).

FIGS. 2A and 2B are schematic drawings showing ray tracing of a distance object imaged through the ophthalmic lenses of FIGS. 1A and 1B. As illustrated, the light rays pass through the lens and the eye and an image of the distance object forms at the retinal plane. Light rays passing through the respective zones are represented as either a focal point at the image plane for light rays traveling through the vision correction zone 101 ran out-of-focus blur circle at the image plane for light rays passing through the myopic defocus zones 102. In the example of FIGS. 2A and 2B, the distant object has been further defined by 3 points; a central object point 1 (OP1) on axis and points 2 and 3 (OP2 and OP3) positioned about 0.5 degree either side of OP1.

The higher magnification inset of the ray tracing formed at and near the image plane, the focal points of OP1, OP2 and OP3 are illustrated as DF1, DF2 and DF3 at the image plane. FIGS. 2A and 2B show the extent of the interactions between the out-of-focus light rays of object points OP1, OP2 and OP3 from the myopic defocus zones and the in-focus images of OP1, OP2 and OP3 produced by the distance powered zone(s) in these coaxial based optical designs.

FIGS. 3A and 3B are schematic drawings of spot diagrams of the focal point, DF1, of object point OP1 formed at the image plane by the ophthalmic lenses of FIGS. 1A and 1B configured with coaxial optics. The spot diagram represents the size of the focal point at the image plane. In some embodiments, the size of the focal point may be expressed as the root mean square of the spot radius in microns (RMS). A smaller spot size may indicate a more distinct focal point (e.g., a good image quality that is in-focus). Conversely, a larger sized spot radius may be indicative of poorer image quality from a less sharp and/or spread image focus that arises, for example, from the overlap and interference of out-of-focus light from other optical zones on the focal point.

In this example, DF1 has an RMS size of 0.52 um at the image plane and 0.4 um for the single ring and dual ring optical designs respectively. These values may be similar to that expected of focal points produced by a single vision optical design. However, the image quality of DF1 may be influenced by the interaction of light rays from adjacent points on the distant object such as OP2 and OP3. When the effect of defocused light rays of OP2 and OP3 from the myopic defocus annular zone of the lens described in FIG. 2A on DF1 is considered the RMS spot size of DF1 increases substantially from 0.52 um to 145.2 um at the image plane for OP2 and OP3 respectively (overall average 118.55 um). Likewise, in the defocused light rays of OP2 and OP3 formed by the myopic defocus annular zones of the lens described in FIG. 2B, the RMS spot size of DF1 also increases substantially from 0.4 um to 147.05 um respectively (overall average 120.06 um) at the image plane. Thus the small, focal point DF1 of OP1 considered in isolation is blurred and increased in size by the impact of light rays of the adjacent object points OP2 and OP3 which are overlapped by out of focus light formed by the myopic defocus zones. In some embodiments, this may suggest that the image formed of OP1 is deteriorated (e.g., substantially deteriorated) by the out-of-focus light rays of adjacent object points generated by coaxial myopic defocus zones.

In some embodiments, the interference of one or more defocused images with the focused image may be controlled; and/or the visual performance, contrast and/or sharpness of the image or the range of extended depth of focus may be improved by designing one or more of the optical zones of the ophthalmic device to comprise laterally separated or displaced optics with respect to at least one other optical zone.

Some embodiments may relate to an ophthalmic lens design that controls the overlap of one or more focal points of an image by an out-of-focus light. In some embodiments, the overlap of one or more focal points of an image by an out-of-focus light may be reduced at least in part, or completely reduced. In other embodiments, the overlap of one or more focal points of an image by one or more out-of-focus images may be reduced by about 5% to 100%, about 10% to 100%, about 15% to 100%, about 20% to 100%, about 25% to 100%, about 30% to 100%, about 35% to 100%, about 40% to 100%, about 45% to 100%, about 50% to 100%, about 55% to 100%, about 60% to 100%, about 65% to 100%, about 70% to 100%, about 75% to 100%, about 80% to 100%, about 85% to 100%, or about 90% to 100%.

In some embodiments, the overlap of focal points associated with an image by focal points associated with one or more out-of-focus images may be controlled at least in part, or completely by separating or displacing one or more focal points associated with an image with one or more focal points associated with the out-of-focus image by e.g., about 0.01 to about 4 mm about 0.01 to about 5 mm or about 0.01 to about 6 mm. In other embodiments, the overlap of an in-focus image by out-of-focus image(s) may be controlled by separating or displacing the one or more focal points associated with in-focus image with the one or more focal points associated with one or more out-of-focus image(s) by, e.g., about 0.01 to about 3.5 mm, about 0.01 to about 3 mm, about 0.01 to about 2.5 mm, about 0.01 to about 2 mm, about 0.01 to about 1.5 mm, about 0.01 to about 1 mm, about 0.01 to about 0.5 mm, about 0.01 to about 0.1 mm, about 0.1 to about 1.5 mm, about 0.1 to about 2 mm, about 0.1 to about 2.5 mm. In some embodiments, the separation may be about 0.1 mm, about 0.5 mm, about 1 mm, about 1.5 mm, about 2 mm, or about 2.5 mm.

Some embodiments described herein may relate to an ophthalmic lens design that improves the quality of an image by controlling the overlap of the focal points at a given image plane with the focal points associated with one of more out-of-focus images or light, wherein the RMS spot size at the image plane is reduced by 1 μm or more. In some embodiments, the reduction in RMS spot size radius achieved by controlling the overlap of the focal points at a given image plane with the one or more focal points associated with one or more out-of-focus images may be about 1 μm or more. In some embodiments, the reduction in RMS spot size radius at the image plane by controlling the overlap of the focal points at a given image plane with the focal points associated with one or more out-of-focus images may be about 5 μm, about 10 μm, about 15 μm, about 20 μm, about 25 μm, about 30 μm, about 35 μm, about 40 μm, about 45 μm, about 50 μm, about 55 μm, about 60 μm, about 65 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, or about 250 μm. In some embodiments, the reduction in RMS spot size radius by controlling the overlap of the focal points at a given image plane with the focal points associated with one or more out-of-focus images may be about 1 μm, about 10 μm, about 25 μm, or about 50 μm.

In some embodiments, the first focal point may be on a first axis at a first distance from the ophthalmic lens and a second focal point may be at a second distance from the ophthalmic lens, the second distance being different that the first distance and displaced from the first axis.

In some embodiments, the overlap of the focal points associated with an image at a given image plane by the focal points associated with out-of-focus images may be substantially controlled by designing an ophthalmic lens with a plurality of optical zones or segments wherein the optical axes for the plurality of optical zones or segments are different from one another and the plurality of optical zones of segments do not share a common axis. In some embodiments, the optical axes of the plurality of optical zones or segments may not fall on a common axis. In some embodiments, some of the optical axes of the plurality of optical zones or segments may fall on a common axis. In some embodiments, the optical axes of the plurality of optical zones associated with a first power may fall on a first optical axis, and the optical axes of the plurality of the optical zones or segments associated with a second power may fall on a second optical axis. In some embodiments, the optical axes of the plurality of optical zones associated with a first power may fall on a first optical axis, and the optical axes of the plurality of the optical zones or segments associated with a second power may fall on a corresponding plurality of axes different than the first axis (e.g., a second optical axis, a third optical axis, a fourth optical axis, a fifth optical axis and so on).

In some embodiments, the optical axes of the plurality of optical zones associated with a first power may fall on a first optical axis, and the optical axes of the plurality of the optical zones or segments associated with a second power may fall on a second optical axis, and the optical axes of the plurality of the optical zones or segments associated with a third power may fall on a third optical axis and so on.

In some embodiments, the overlap of the focal points associated with an image at a given image plane by the focal points or rays associated with an out-of-focus image may be controlled, by configuring an ophthalmic lens to have a plurality of optical zones or segments. The one or more optical zones or segments may have an optical axis and one or more optical zones or segments may not share a common axis (e.g., may have different optical axes). Therefore, focal points resulting from the one or more optical zones or segments may be displaced with respect to the optical axes and focal points from other optical zones or segments of the ophthalmic lens. In some embodiments, the displacement of focal points resulting from light directed through one or more optical zones or segments with respect to focal points resulting from light directed through other optical zones or segments of the ophthalmic lens may result in a modification or variation of the defocused or out-of-focused light with an image at a given image plane and therefore the quality (e.g., contrast and/or sharpness) of the retinal image may be improved and/or may result in an extended depth of focus.

In some embodiments, the displacement of focal points resulting from light directed through one or more optical zones or segments with respect to focal points resulting from light directed through other optical zones and/or segments on the ophthalmic lens may be addressed by one or more of an optical separation means (e.g., laterally separated optics). In some embodiments, the optical separation means (e.g., laterally separated optics) for displacing focal points resulting from light directed through one or more optical zones or segments with respect to focal points resulting from light directed through other optical zones and/or segments on the ophthalmic lens may comprise utilizing one or more optical surfaces comprising two or more optical elements (for example, sphere, ellipse, conic, asphere, or other suitable elements including non-spheroidal torus elements such as line, conicroids) wherein the two or more optical elements are placed, shifted, rotated, tilted or displaced relative to one another so that at least a substantial portion or at least a portion of the two or more optical elements do not share a common optical axis. In some embodiments, the optical separation means (e.g., laterally separated optics) for displacing focal points resulting from light directed through one or more optical zones or segments with respect to focal points resulting from light directed through other optical zones and/or segments on the ophthalmic lens may comprise utilizing an optical surface comprising two or more optical elements (for example, sphere, ellipse, conic, asphere, or other suitable elements including non-spheroidal torus elements such as line, conicroids), wherein the two or more optical elements may have different radii. The optical surface of the ophthalmic lens may be the front surface, the back surface or both the surfaces of the lens.

In some embodiments, an optical zone with a first power may be in the center of the lens, or substantially in the center of the lens, and the optical zone with a second power may surround the central optical zone as a concentric zone or as a substantially concentric zone. In some embodiments, an optical zone with a first power may occupy a section, a meridian, or a portion of the lens and an optical zone with the second power may occupy a remaining section, a remaining meridian, or a remaining portion of the lens (e.g., a segmented ophthalmic lenses). In some embodiments, an optical zone with a first power may occupy multiple portions of a lens and alternate between the optical zones with the second power (e.g., a multi-ring). In some embodiments, the first power may be uniform or may vary in different portions of the first optical zone. In some embodiments, the ophthalmic lens may comprise a third optical zone with a third power. In some embodiments, the third optical zone may be one or more concentric zones proximate to (e.g., surrounding) the central optical zone. In some embodiments, the third optical zone may be a section, meridian or a portion of the lens other than the section, meridian or portion of the lens occupied by the first optical zone and the second optical zone.

In some embodiments, e.g., with segmented ophthalmic lenses, the optical element with the first power may be the first optical zone and the first axis may be an optical axis of the first optical zone. In some embodiments, the optical element with the second power may be the second optical zone. The second optical zone may have a second axis, the second axis being displaced or laterally separated from the first axis. In some embodiments, the separation of the centers of the two optical elements relative to the center of the ophthalmic lens may range from about 0.01 to about 20 mm (e.g., about 0.01 mm, about 0.02 mm, about 0.03 mm, about 0.04 mm, about 0.05 mm, about 0.06 mm, about 0.07 mm, about 0.08 mm, about 0.09 mm, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 0.95 mm, about 1 mm, about 1.25 mm, about 1.5 mm, about 1.75 mm, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, about 5.25 mm, about 5.5 mm, about 5.75 mm, about 6 mm, about 6.25 mm, about 6.5 mm, about 6.75 mm, about 7 mm, about 7.25 mm, about 7.5 mm, about 7.75 mm, about 8 mm, about 8.25 mm, about 8.5 mm, about 8.75 mm, about 9 mm, about 9.25 mm, about 9.5 mm, about 9.75 mm, about 10 mm, about 10.25 mm, about 10.5 mm, about 10.75 mm, about 11 mm, about 11.25 mm, about 11.5 mm, about 11.75 mm, about 12 mm, about 12.25 mm, about 12.5 mm, about 12.75 mm, about 13 mm, about 13.25 mm, about 13.5 mm, about 13.75 mm, about 14 mm, about 14.25 mm, about 14.5 mm, about 14.75 mm, about 15 mm, about 15.25 mm, about 15.5 mm, about 15.75 mm, about 16 mm, about 16.25 mm, about 16.5 mm, about 16.75 mm, about 17 mm, about 17.25 mm, about 17.5 mm, about 17.75 mm, about 18 mm, about 18.25 mm, about 18.5 mm, about 18.75 mm, about 19 mm, about 19.25 mm, about 19.5 mm, about 19.75 mm, about 20 mm, about 20.25 mm, about 20.5 mm, about 20.75 mm, or about 21 mm). In some embodiments, the separation may be about 10 mm for spectacle lenses and about 2 mm for contact lenses. In some embodiments, the separation may be about 9 mm, about 9.25 mm, about 9.5 mm, about 9.75 mm, about 10 mm, about 10.25 mm, about 10.5 mm, about 10.75 mm, or about 11 mm, for spectacle lenses. In some embodiments, the separation may be about 1 mm, about 1.25 mm, about 1.5 mm, about 1.75 mm, about 2 mm, about 2.25 mm, about 2.5 mm, about 2.75 mm, or about 3 mm for contact lenses.

In some embodiments, the displacement of focal points resulting from light directed through one or more optical zones or segments with respect to focal points resulting from light directed through other optical zones and/or segments on the ophthalmic lens using an optical separation means (e.g., laterally separated optics) may result in a prismatic power and may result with the wearer of ophthalmic lens perceiving the object as being displaced during use. In some embodiments, it may be desirable to reduce but still maintain separation of the images (e.g., the focal points) which may lead to a tradeoff between lower prism power (reduced separation of the images) and higher image quality (increased separation of the images) of the vision in the lens.

In some embodiments, the optical zone with the first power may be the first optical zone and the first axis may be an optical axis of the first optical zone. In some embodiments, the optical zones with the second power may be the second optical zone. The second optical zone may have a second axis, the second axis being displaced or laterally separated from the first axis.

In some embodiments, the second optical zone may be configured such that, in use with the eye, light passing through the second optical zone is refracted to a plurality of second focal points, the plurality of second focal points being on a corresponding one or more of a plurality of second axes associated with the one or more second optical zones, the plurality of second axes being displaced from the first axis. In some embodiments, the second optical zone may have multiple focal points. In some embodiments, the second optical zone may be configured such that, in use with the eye, the light passing through the second optical zone is refracted to multiple (e.g., 1, 2, 3, 4, 5, 6, 7, 8, 9, 10, 11, 12, 13, 14, 15, or 16) focal points, not on the first axis. In some embodiments, the light passing through the second optical zone may be refracted to 3, 3, 4, or 5 focal points, not on the first axis. In some embodiments, this configuration may be useful for ophthalmic lenses used to address myopia.

In some embodiments, the ophthalmic lens may comprise a first optical zone with a first power, a second optical zone with uniform (or varying power), a third optical zone with uniform (or varying power) and so on.

In some embodiments, the displacement of the first axis from the second axis may create a prism power on the ophthalmic lens. In some embodiments, the prism power created by the displacement of the first axis from the second axis may be about 0.01Δ diopter to about 15Δ diopters (e.g., about 0.01Δ, about 0.015Δ, about 0.02Δ, about 0.025Δ, about 0.05Δ, about 0.075Δ, about 0.1Δ, about 0.125Δ, about 0.15Δ, about 0.175Δ, about 0.2Δ, about 0.25Δ, about 0.3Δ, about 0.35Δ, about 0.4Δ, about 0.45Δ, about 0.5Δ, about 0.6Δ, about 0.7Δ, about 0.8Δ, about 0.9Δ, about 1Δ, about 1.25Δ, about 1.5Δ, about 1.75Δ, about 2Δ, about 2.25Δ, about 2.5Δ, about 2.75Δ, about 3Δ, about 3.25Δ, about 3.5Δ, about 3.75Δ, about 4Δ, about 4.25Δ, about 4.5Δ, about 4.75Δ, about 5Δ, about 5.25Δ, about 5.5Δ, about 5.75Δ, about 6Δ, about 6.25Δ, about 6.5Δ, about 6.75Δ, about 7Δ, about 7.25Δ, about 7.5Δ, about 7.75Δ, about 8Δ, about 8.1Δ, about 8.2Δ, about 8.3Δ, about 8.4Δ, about 8.5Δ, about 8.6Δ, about 8.7Δ, about 8.8Δ, about 8.9Δ, about 9Δ, about 9.1Δ, about 9.2Δ, about 9.3Δ, about 9.4Δ, about 9.5Δ, about 9.6Δ, about 9.7Δ, about 9.8Δ, about 9.9Δ, about 10Δ, about 10.1Δ, about 10.2Δ, about 10.3Δ, about 10.4Δ, about 10.5Δ, about 10.6Δ, about 10.7Δ, about 10.8Δ, about 10.9Δ, about 11Δ, about 11.25Δ, about 11.5Δ, about 11.75Δ, about 12Δ, about 12.25Δ, about 12.5Δ, about 12.75Δ, about 13Δ, about 13.25Δ, about 13.5Δ, about 13.75Δ, about 14Δ, about 14.25Δ, about 14.5Δ, about 14.75Δ, or about 15Δ). In some embodiments, the prism power created by the displacement of the first axis from the second axis may be about 1Δ, about 2Δ, about 3Δ, about 4Δ, about 5Δ, about 6Δ, about 7Δ, about 8Δ, or about 9Δ.

In some embodiments, the one or more optical zones with the first power may occupy more than 50% (e.g., about 55%, about 60%, about 65%, about 70%, about 75%, about 80%, about 85%, or about 90%) of the surface area (e.g., the front or back surface area of the lens) of the optic zone of the ophthalmic lens. In some embodiments, the one or more optical zones with the first power may occupy less than 50% (e.g., about 45%, about 40%, about 35%, about 30%, about 25%, or about 20%) of the surface area (e.g., the front or back surface area of the lens) of the optic zone of the ophthalmic lens. In some embodiments, the one or more optical zones with the first power may occupy about 60% (e.g., about 55%, about 56%, about 57%, about 58%, about 59%, about 60%, about 61%, about 62%, about 63%, about 64%, or about 65%) of the surface area (e.g., the front or back surface area of the lens) of the optic zone of the ophthalmic lens. In some embodiments, the one or more optical zones with the first power may occupy about 40% (e.g., about 35%, about 36%, about 37%, about 38%, about 39%, about 40%, about 41%, about 42%, about 43%, about 44%, or about 45%) of the surface area (e.g., the front or back surface area of the lens) of the optic zone of the ophthalmic lens. In some embodiments, the one or more optical zones with the first power may occupy less than about 75% (e.g., about 55%, about 60%, about 65%, about 70%, or about 75%) of the surface area (e.g., the front or back surface area of the lens) of the optic zone of the ophthalmic lens. In some embodiments, the one or more optical zones with the first power may occupy more than about 10%, (e.g., about 15%, about 20%, about 25%, about 30%, about 35%, about 40%, or about 45%) of the surface area (e.g., the front or back surface area of the lens) of the optic zone of the ophthalmic lens.

In some embodiments, the optical zone with the first power may be defined, at least in part, by a sphere having a first radius and/or the optical zone with the second power may be defined, at least in part, by a sphere having a second radius, different than the first radius. In some embodiments, the optical zone with the first power may be defined, at least in part, by a sphere having a first radius and/or the optical zone with the second power may be defined, at least in part, by a sphere having a second radius, smaller than the first radius. In some embodiments, the optical zone with the first power may be defined, at least in part, by a sphere having a first radius and/or the optical zone with the second power may be defined, at least in part, by a sphere having a second radius, larger than the first radius.

In some embodiments, the one or more optical zones with the second power may comprise one or more spheres having one or more radii that are different to the one or more optical zones with the first power and a first radius.

In some embodiments (e.g., for contact lenses), the first optical zone may be substantially circular in shape and have a diameter of about 3 mm (e.g., in some embodiments, the diameter may be about 2 mm, about 2.5 mm, about 3 mm, about 3.5 mm, about 4 mm, about 2-4 mm, about 2-3 mm, about 3-4 mm, less than about 4 mm, less than about 3.5 mm, and/or less than about 3 mm). In some embodiments, the second optical zone may be substantially annular in shape and have an inner diameter of about 3 mm (e.g., in some embodiments, the inner diameter may be about 2 mm, about 2.5 mm, about 3 mm, about 3.5 mm, about 4 mm, about 2-4 mm, about 2-3 mm, about 3-4 mm, less than about 4 mm, less than about 3.5 mm, and/or less than about 3 mm) and an outer diameter of about 7 mm (e.g., in some embodiments, the outer diameter may be about 5 mm, about 5.5 mm, about 6 mm, about 6.5 mm, about 7 mm, about 7.5 mm, about 8 mm, about 5-8 mm, about 6-7 mm, about 6-8 mm, less than about 8 mm, less than about 7.5 mm, and/or less than about 7 mm). In some embodiments, the first optical zone may be substantially circular in shape and the second optical zone may be substantially annular in shape and an inner diameter of the second optical zone may be substantially equal to the diameter of the first optical zone.

In some embodiments (e.g., for spectacle lenses), the first optical zone may be substantially circular in shape and have a diameter of about 10 mm (e.g., in some embodiments, the diameter may be about 7 mm, about 7.5 mm, about 8 mm, about 8.5 mm, about 9 mm, about 9.5 mm, about 10 mm, about 10.5 mm, about 11 mm, about 11.5 mm, about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.5 mm, about 18 mm, about 18.5 mm, about 19 mm, about 19.5 mm, about 20 mm, about 8-10 mm, about 10-12 mm, about 9-11 mm, about 12-14 mm, less than about 10 mm, less than about 12.65 mm, and/or less than about 15 mm). In some embodiments, the second optical zone may be substantially annular in shape and have an inner diameter of about 10 mm (e.g., in some embodiments, the inner diameter may be about 7 mm, about 7.5 mm, about 8 mm, about 8.5 mm, about 9 mm, about 9.5 mm, about 10 mm, about 10.5 mm, about 11 mm, about 11.5 mm, about 12 mm, about 12.5 mm, about 13 mm, about 7-9 mm, about 8-10 mm, about 10-12 mm, less than about 10 mmm, less than about 11 mm, and/or less than about 12 mm) and an outer diameter of about 15 mm (e.g., in some embodiments, the outer diameter may be about 12 mm, about 12.5 mm, about 13 mm, about 13.5 mm, about 14 mm, about 14.5 mm, about 15 mm, about 15.5 mm, about 16 mm, about 16.5 mm, about 17 mm, about 17.5 mm, about 18 mm, about 18.5 mm, about 19 mm, about 19.5 mm, about 20 mm, about 12-15 mm, about 13-16 mm, about 15-18 mm, less than about 15 mm, less than about 17.5 mm, and/or less than about 20 mm). In some embodiments, the first optical zone may be substantially circular in shape and the second optical zone may be substantially annular in shape and an inner diameter of the second optical zone may be substantially equal to the diameter of the first optical zone.

The teachings of the present disclosure may be applied to ophthalmic lenses for presbyopia and/or myopia. The ophthalmic lenses described herein may include one or more of the following: a spectacle lens, a contact lens, a corneal onlay, a corneal inlay, a film or sheet applied to a lens, a clip-on lens, and an intraocular lens. For example, a bifocal ophthalmic lens (e.g., a contact lens or a spectacle lens) may be configured such that the ophthalmic lens has one or more optical zones with a first power to correct for one of a distant, intermediate or near vision and one or more optical zones with a second power to that is more positive than the first power. In some embodiments, the optical zones may be constructed such that when viewing objects, the focal points resulting from light rays (or at least a portion of light rays) refracted from the one or more optical zones with the second power are displaced from the focal points resulting from light rays (or at least a portion of light rays) refracted from the one or more optical zones with the first power and therefore the image quality associated with a first image may be improved (e.g., there may a reduced amount of overlapping light rays from the one or more optical zones with the second power) and/or provide an extended depth of focus. In some embodiments, when viewing objects at a distance, light directed through the one or more optical zones with the first power may come to a focus at a first focal point that is displaced from the light directed through the one or more optical zones with the second power and therefore, the focal points resulting from light directed through the optical zones with the first power may be minimally interfered with (e.g., there is less, substantially less, and/or no interference) by the focal points resulting from light directed through the optical zones with the second power. In some embodiments, the one or more optical zones with the first power and the one or more optical zones with the second power have independent optical axes that are displaced relative to one another with partial or reduced overlap of the resulting images. In some embodiments, during distance and/or near viewing, the interference of the out-of-focus image from one or more optical zones with the second power with the image from the one or more optical zones with the first power may be controlled by using an optical surface comprising 2 or more optical elements (for example, sphere, ellipse, conic, asphere or other suitable element including non-spheroidal torus elements such as line, conicroids.) wherein the two or more optical elements are placed, shifted, tilted, rotated or displaced relative to one another so that they do not share a common optical axis.

Figures 4A, 4B, 5A, 5B:
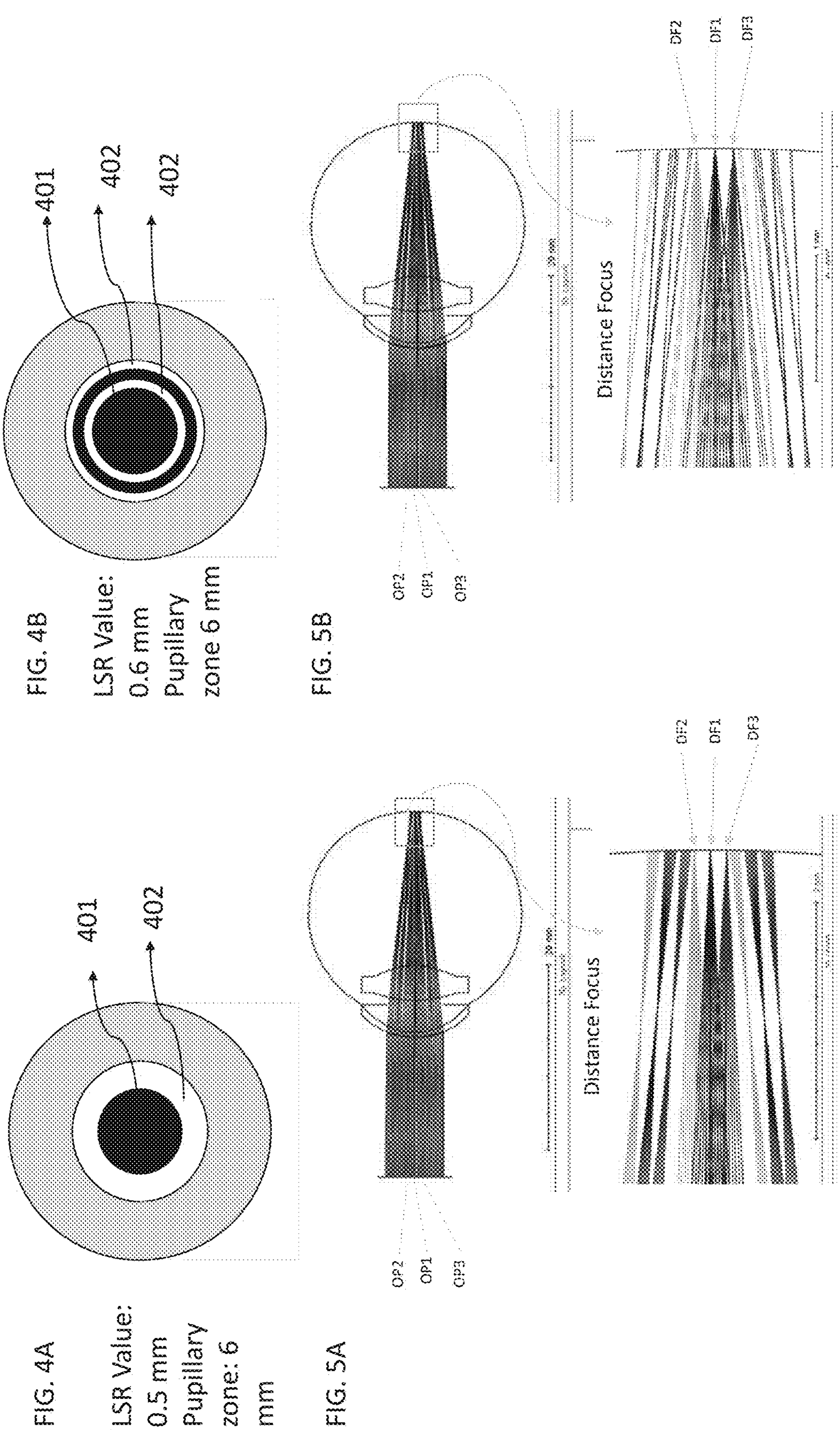
FIGS. 4A and 4B are schematic drawings showing a plan view of ophthalmic lenses (e.g., contact lenses) incorporating a central vision correction zone surrounded by zones powered to create myopic defocus for myopia control in accordance with certain embodiments.
FIGS. 5A and 5B are schematic drawings showing ray tracing of a distance object imaged through the ophthalmic lenses of FIGS. 4A and 4B in accordance with certain embodiments.

FIGS. 4A and 4B are schematic drawings showing a plan view of ophthalmic lenses (e.g., contact lenses) incorporating a central zone 401 with first power surrounded by zones 402 powered to create myopic defocus relative to zone 401 for myopia control in accordance with certain embodiments. As illustrated, the central zone 401 and surrounding myopic defocus powered zones 402 are configured to be non-coaxial such that the focal points produced by the myopic defocus zones are laterally separated from one another and also separated from the axis on which the distance focal point is created. FIG. 4A has a single ring of myopic defocus power and FIG. 4B has 2 annuli of myopic defocus power separated by a zone with first power. Both lenses comprise a zone on axis with a first power while the focal points of the myopic defocus zones are configured to be laterally separated by e.g., 0.5 mm in FIG. 4A or 0.6 mm in FIG. 4B. In the examples shown, both lens types incorporate +2.5 D of myopic defocus in annular arrangements. FIGS. 4A and 4B illustrate continuous surrounding zones, however, also contemplated are surrounding zones that may be discontinuous or combinations of continuous and discontinuous. FIGS. 4A and 4B illustrate concentric circular zones, however, other shapes are also contemplated, for example, sphere, ellipse, conic, asphere or other suitable elements including non-spheroidal torus elements such as line, conicroids. FIGS. 4A and 4B illustrate concentric zones, however, also contemplated are substantially concentric and/or partially concentric zones.

FIGS. 5A and 5B are schematic drawings showing ray tracing of a distance object imaged through the ophthalmic lenses of FIGS. 4A and 4B in accordance with certain embodiments. Light rays passing through the respective zones are represented as either a focal point at the image plane for light rays traveling through the zones with the first power or as an out-of-focus blur circle at the image plane for light rays passing through the myopic defocus zones. In FIGS. 5A and 5B, the distance object is further defined by three points; a central object point 1 (OP1) on axis and points 2 and 3 (OP2 and OP3) positioned 0.5 degrees on either side of OP1.

FIGS. 5A and 5B also illustrate a higher magnification inset of the ray tracing formed at and near the retinal plane. The inset shows the focal points of OP1, OP2 and OP3 as DF1, DF2 and DF3 at the image plane. In addition, the out-of-focus rays of OP1, OP2 and OP3 passing through the myopic defocus zones make up the remaining light rays falling at the image plane. Both FIGS. 5A and 5B illustrate the extent of the interactions between the out-of-focus light rays of object points OP1, OP2 and OP3 from the myopic defocus zones and the images of OP1, OP2 and OP3 by the distance powered zone(s) in these lenses configured to laterally separate the focal points.

FIGS. 6A and 6B are schematic drawings showing spot diagrams and RMS values of the focal point, DF1, of object point OP1 formed at the retinal plane by the ophthalmic lenses of FIGS. 4A and 4B in accordance with certain embodiments based on optical designs creating lateral separation of the focal points. DF1 has an RMS value of 0.46 um and 0.41 um for the single ring and dual ring optical designs respectively. These values may be similar to that expected of a focal point of a single vision optical design. However, unlike the example of ophthalmic lenses configured with coaxial optics, such as in FIGS. 2A and 2B, there may not be interaction from the defocused light rays of object points OP2 and OP3 formed by the myopic defocus zones (e.g., RMS values=0). The focal point DF1 may not have defocused light rays from adjacent object points overlaying and increasing the RMS spot size and the overall average RMS values remain relatively small at 0.46 um and 0.41 um because the lens designs comprise laterally separated foci. Likewise, DF2 and DF3 are also not impacted by defocused light from adjacent object points. Therefore, the laterally separated optics described in this example show improved sharpness and higher image quality than the coaxial based designs of FIGS. 2A and 2B.

Figures 7A, 7B, 8A, 8B:
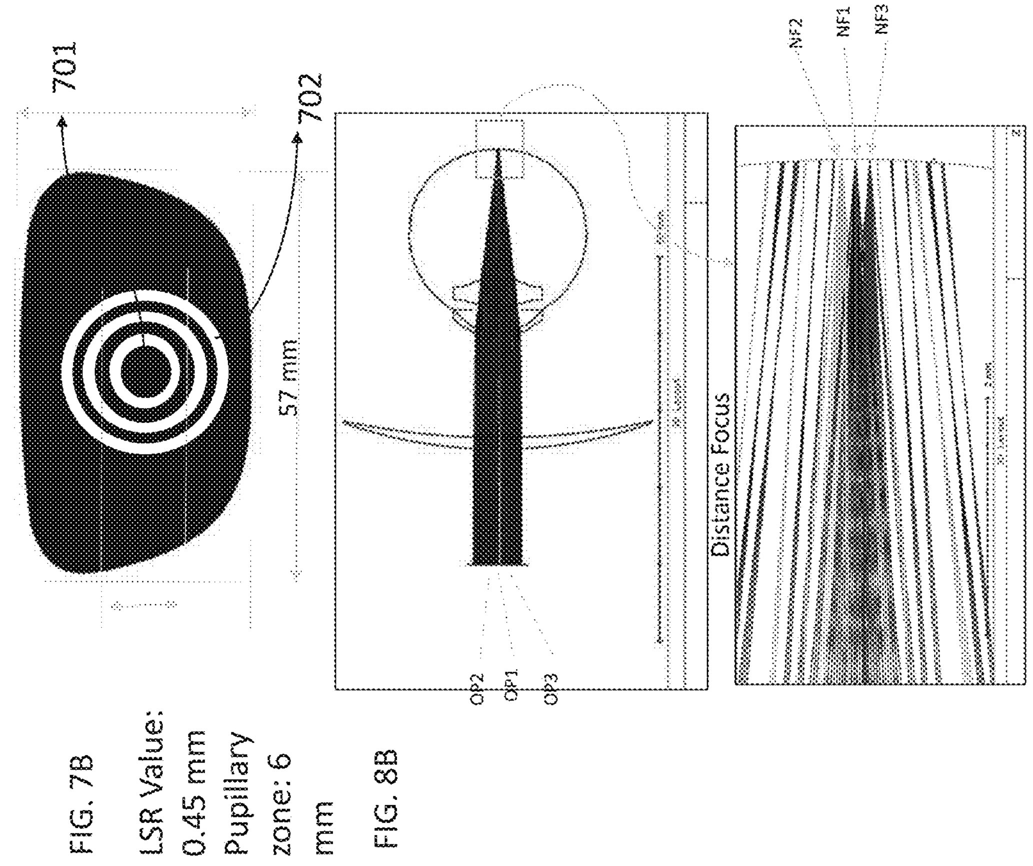
FIGS. 7A and 7B are schematic drawings showing a plan view of ophthalmic lenses (e.g., spectacle lenses) configured for myopia control and incorporating a central vision correction zone and multiple annular zones alternating in power between to create myopic defocus in accordance with certain embodiments.
FIGS. 8A and 8B are schematic drawings showing ray tracing of a distance object imaged through the ophthalmic lenses of FIGS. 7A and 7B in accordance with certain embodiments.

FIGS. 7A and 7B are schematic drawings showing a plan view of ophthalmic lenses (e.g., spectacle lenses) configured for myopia control and incorporating a central zone with a first power 701 surrounded by multiple annular zones 702 alternating in power between to create myopic defocus in accordance with certain embodiments. The lens shown in FIG. 7A is configured so that the zone with the first power 701 and myopic defocus zones may be coaxial and incorporate +2.5 D of myopic defocus in the myopic defocus annular zones. The lens shown in FIG. 7B is configured so that the zone with the first power 701 and myopic defocus zones 702 may comprise laterally separated optics and incorporate +2.5 D of myopic defocus in the myopic defocus annular zones. FIGS. 7A and 7B illustrate continuous surrounding zones, however, also contemplated are surrounding zones that may be discontinuous or combinations of continuous and discontinuous. FIGS. 7A and 7B illustrate concentric circular zones, however, other shapes are also contemplated, for example, sphere, ellipse, conic, asphere or other suitable elements including non-spheroidal torus elements such as line, conicroids. FIGS. 7A and 7B illustrate concentric zones, however, also contemplated are substantially concentric and/or partially concentric zones.

FIGS. 8A and 8B are schematic drawings showing ray tracing of a distance object imaged through the ophthalmic lenses of FIGS. 7A and 7B in accordance with certain embodiments. Light rays passing through the respective zones are represented as either a focal point on the retina for light rays traveling through the distance powered zones or as an out-of-focus blur circle at the image plane for light rays passing through the myopic defocus zones. The distance object has been further defined by three points; a central object point 1 (OP1) on axis and points 2 and 3 (OP2 and OP3) positioned 0.45 degrees on either side of OP1.

FIGS. 8A and 8B also include a higher magnification inset of the ray tracing formed at and near the retinal plane. The inset shows the focal points of the distance object points OP1, OP2 and OP3 as DF1, DF2 and DF3 at the image plane. In addition, the out-of-focus rays of OP1, OP2 and OP3 passing through the myopic defocus zones make up the remaining light rays falling at the image plane. Both FIGS. 8A and 8B illustrate the extent of the interactions between the out-of-focus light rays of object points OP1, OP2 and OP3 from the myopic defocus zones and the in-focus images of OP1, OP2 and OP3 by zones with the first power in these lenses configured with either coaxial optical designs (FIG. 8A) or optical designs that laterally separate the focal points (FIG. 8B).

FIGS. 9A and 9B are schematic drawings showing spot diagrams and RMS values of the focal point, DF1, of object point OP1 formed at the retinal plane by the ophthalmic lenses of FIGS. 7A and 7B in accordance with certain embodiments. FIG. 9A illustrates spot diagrams and RMS values of the focal point, F1, of object point OP1 formed at the retinal plane by the myopia control lenses of FIG. 8*a* based on coaxial optical designs. DF1 has an RMS value of 0.38 um which is a value comparable to that expected of a focal point of a single vision optical design. However, the image quality of DF1 may be influenced by the interaction of light rays from adjacent points on the distance object such as OP2 and OP3. When the effect of defocused light rays of OP2 and OP3 from the myopic defocus annular zone of the lens described in FIG. 8A on F1 is considered, then the RMS spot size of DF1 increases substantially from 0.38 um to 126.39 um for OP2 and OP3 respectively (overall average 103.19 um). Thus the defined focal point F1 of OP1 considered in isolation has now been blurred and increased in size by the impact of myopically defocused light rays of the adjacent object points OP2 and OP3 formed by the myopic defocus zones. This shows the image formed of OP1 may be deteriorated by the out-of-focus light rays of adjacent object points generated by coaxial myopic defocus zones.

FIG. 9B illustrates spot diagrams and RMS values of the focal point, DF1, of object point OP1 formed at the retinal plane by the myopia control lenses of FIG. 8B based on optical designs creating lateral separation of the focal points. DF1 has an RMS value of 0.36 um and this value, like in FIG. 9A, is similar to that expected of a focal point of a single vision optical design. However, unlike the cases of lenses configured with coaxial optics such as in FIG. 2A and FIG. 8A, contact lenses and spectacles respectively with coaxial optical designs, there does not seem to be interaction from the defocused light rays of object points OP2 and OP3 formed by the myopic defocus zones (RMS values=0.0). In the example of FIG. 9B, the focal point DF1 does not have defocused light rays from adjacent object points overlaying and increasing the RMS spot size and so the overall average RMS values remain small at 0.36 um for this spectacle lens configured with laterally separated foci. Likewise, F2 and F3 are also similarly not impacted by defocused light from adjacent object points. Therefore, the laterally separated optics described in this exemplary embodiment show improved sharpness and/or higher image quality than coaxial based designs.

Figures 10A, 11A:
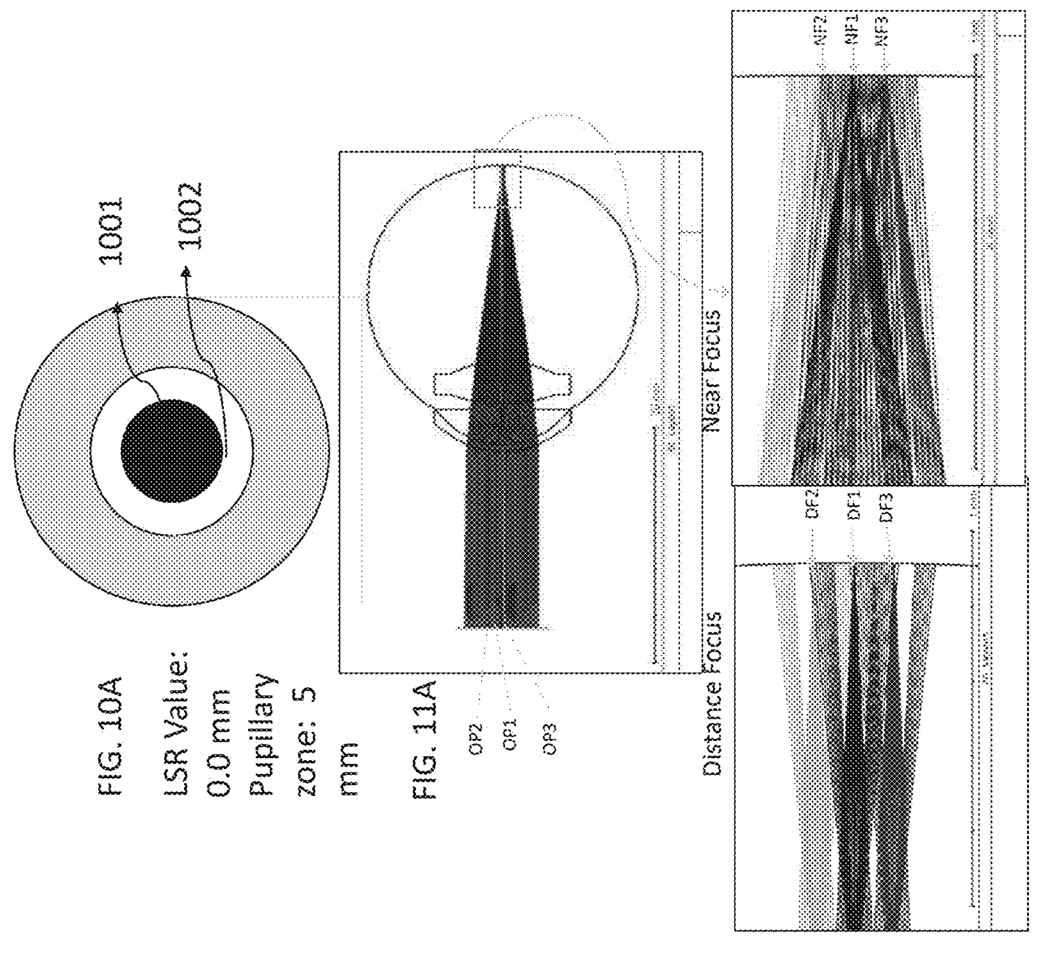
FIGS. 10A and 10B are schematic drawings showing a plan view of ophthalmic lenses (e.g., bifocal soft contact lenses for presbyopia) incorporating a central vision correction zone and zone(s) powered to correct the near vision of a presbyope.
FIGS. 11A and 11B are schematic drawings showing ray tracing of a distance object and a near object imaged through the ophthalmic lenses of FIGS. 10A and 10B.
Figures 10B, 11B:
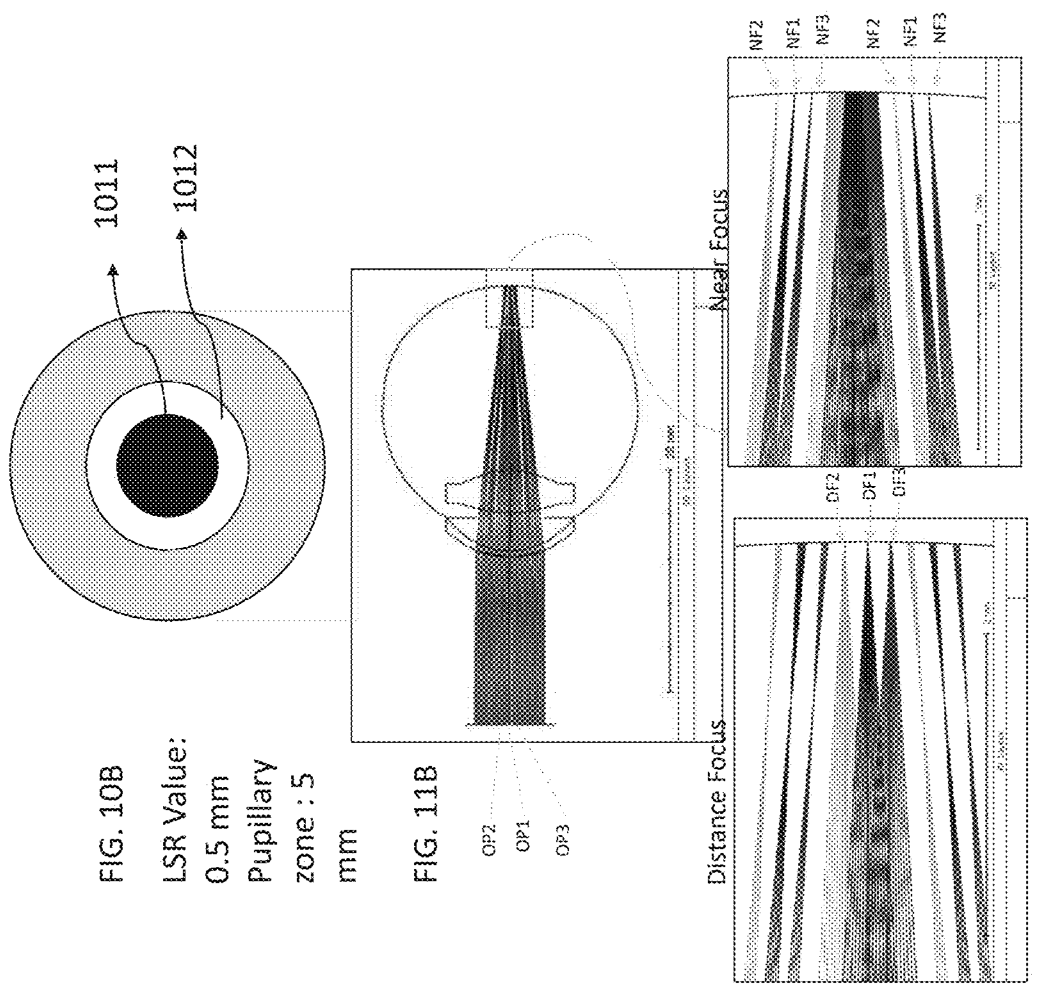

FIGS. 10A and 10B are schematic drawings showing a plan view of ophthalmic lenses (e.g., bifocal soft contact lenses for presbyopia) incorporating a central vision correction zone surrounded by zone(s) powered to correct the near vision of a presbyope in accordance with certain embodiments. FIG. 10A illustrates a plan view of a bifocal soft contact lens for presbyopia incorporating a central distance vision correction zone 1001 surrounded by a single zone 1002 powered to correct the near vision of the presbyope. The distance and near correction zones may be configured to be coaxial and incorporate +2.5 D near addition in the surrounding annular zone.

FIG. 10B illustrate a plan view of a soft bifocal contact lens incorporating a central distance vision correction zone 1011 surrounded by a zone 1012 powered to correct the near vision of the presbyope. The distance zone and surrounding near powered zone may be configured to comprise laterally separated optics such that the focal points produced by the zones are laterally separated from one another and also separated from the axis on which the distance focal point is created. The lens of FIG. 10B may be configured to have the focal point from the distance zone formed on axis but the focus formed by the near vision zone is laterally separated from the optical axis by 0.5 mm. In this exemplary embodiment, the near annular zone does not converge light to a single focal point but rather forms a continuous ring of focus surrounding and separated from the optical axis on which the distance focal point lies. Thus, the near focal ring is laterally separated from the optical axis by 0.5 mm. The bifocal lens in this example incorporates +2.50 D near addition. FIG. 10B illustrate continuous surrounding zones, however, also contemplated are surrounding zones that may be discontinuous or combinations of continuous and discontinuous. FIGS. 10A and 10B illustrate concentric circular zones, however, other shapes are also contemplated, for example, sphere, ellipse, conic, asphere or other suitable elements including non-spheroidal torus elements such as line, conicroids. FIGS. 10A and 10B illustrate concentric zones, however, also contemplated are substantially concentric and/or partially concentric zones.

FIGS. 11A and 11B are schematic drawings showing ray tracing of a distance object and a near object imaged through the ophthalmic lenses of FIGS. 10A and 10B.

FIG. 11A shows the ray tracing of a distance object imaged through the contact lens of FIG. 10A. The light rays pass through the lens and the eye and an image of the distance object forms at the retinal plane. Light rays passing through the respective zones may be represented as either a focal point at the image plane for light rays traveling through the distance powered zones or an out-of-focus blur circle at the image plane for light rays passing through the near addition zone. The distance object has been further defined by three points; a central object point 1 (OP1) on axis and points 2 and 3 (OP2 and OP3) positioned 0.5 degrees either side of OP1 of the distance object and 0.15 degrees either side of OP1 of the near object.

FIG. 11A also illustrates a higher magnification inset of the ray tracing formed when the distance object is in focus (distance) and when the near image is in focus (near) at the retinal plane. FIG. 11A shows the focal points of the distance object OP1, OP2 and OP3 as DF1, DF2 and DF3 at the image plane and, in addition, the out-of-focus rays of OP1, OP2 and OP3 passing through the near addition zones make up the remaining light rays falling at the image plane. FIG. 11A further illustrates the focal points of a near object OP1, OP2 and OP3 as NF1, NF2 and NF3 at the image plane and. The out-of-focus rays of OP1, OP2 and OP3 passing through the distance vision zone make up the remaining light rays falling at the image plane. FIG. 11A illustrates the extent of the interactions between the out-of-focus light rays of object points OP1, OP2 and OP3 and the images of OP1, OP2 and OP3 produced by the distance or near powered zone(s) in these coaxial based optical designs.

FIG. 11B illustrates the cross-section of ray tracing of a distance object imaged through the contact lens of FIG. 10B. The light rays pass through the lens and the eye and an image of the distance object forms at the retinal plane. Light rays passing through the respective zones may be represented as either a focal point at the image plane for light rays traveling through the distance powered zones or an out-of-focus blur circle at the image plane for light rays passing through the near addition zone. The distance object may be further defined by three points; a central object point 1 (OP1) on axis and points 2 and 3 (OP2 and OP3) positioned 0.5 degrees either side of OP1 of the distance object and 0.15 degrees either side of OP1 of the near object.

FIG. 11B also provides a higher magnification inset of the ray tracing formed when the distance object is in focus (distance) and when the near image is in focus (near) at the retinal plane. FIG. 11B illustrates the focal points of the distance object OP1, OP2 and OP3 as DF1, DF2 and DF3 at the image plane and the out-of-focus rays of OP1, OP2 and OP3 passing through the near addition zones make up the remaining light rays falling at the image plane. This example further illustrates the focal points of a near object OP1, OP2 and OP3 as NF1, NF2 and NF3 at the image plane and, in addition, the out-of-focus rays of OP1, OP2 and OP3 passing through the distance vision zone make up the remaining light rays falling at the image plane. FIG. 11B illustrates the extent of the interactions between the out-of-focus light rays of object points OP1, OP2 and OP3 and the in focus images of OP1, OP2 and OP3 produced by the distance or near powered zone(s) in these laterally separated optical designs.

FIGS. 12A, 12B, 12C, and 12D are schematic drawings showing spot diagrams and RMS values of the focal point, DF1 and NF1, of object point OP1 formed at the retinal plane by the ophthalmic lenses of FIGS. 10A and 10B.

Figures 12A, 12B:
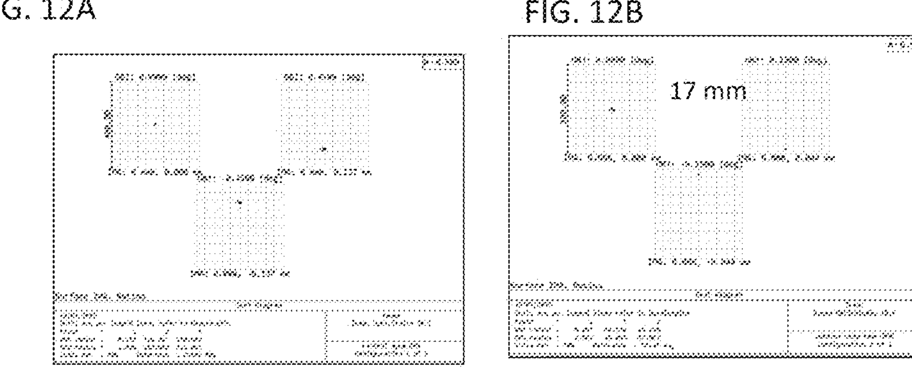
FIGS. 12A, 12B, 12C, and 12D are schematic drawings showing spot diagrams and RMS values of the focal point, DF1 and NF1, of object point OP1 formed at the retinal plane by the ophthalmic lenses of FIGS. 10A and 10B.

FIG. 12A illustrates the spot diagram and RMS values of the focal point DF1 of the distance object point OP1 formed at the retinal plane by the bifocal contact lens of FIG. 11A. DF1 has an RMS size of 0.71 um. These values are approximately similar to focal points produced by a single vision optical design for this aperture size. However, the image quality of DF1 may be influenced by the interaction of light rays from adjacent points on the distance object such as OP2 and OP3. When the effect of defocused light rays of OP2 and OP3 from the near powered annular zone of the lens described in FIG. 10A on D-F1 is considered, the RMS spot size of DF1 increases substantially from 0.71 um to 110.99 um for OP2 and OP3 respectively (overall average 90.62 um). Thus, the focal point DF1 of OP1 considered in isolation has now been blurred and increased in size by the real impact of defocused light rays of the adjacent object points OP2 and OP3 formed by the near powered zones. In some embodiments, this illustrates the image formed of OP1 is deteriorated by the out-of-focus light rays of adjacent object points generated by coaxial near powered zone.

FIG. 12B illustrates the spot diagram and RMS values of the focal point NF1 of the near object point OP1 formed at the retinal plane by the bifocal contact lens of FIG. 11A. N-F1 has an RMS size of 0.2 um. These values are approximately similar to that expected of focal points produced by a single vision optical design for this aperture size. However, the image quality of NF1 may be influenced by the interaction of light rays from adjacent points on the near object such as OP2 and OP3. When the effect of defocused light rays of OP2 and OP3 from the distance powered central zone of the lens described in FIG. 10A on N-F1 is considered, the RMS spot size of N-F1 increases substantially from 0.2 um to 44.15 um for OP2 and OP3 respectively (overall average 36.05 um). Thus, the focal point N-F1 of OP1 considered in isolation has now been blurred and increased in size by the impact of defocused light rays of the adjacent near object points OP2 and OP3 formed by the distance powered zone. In some embodiments, this shows the near image formed of OP1 is deteriorated by the out-of-focus light rays of adjacent object points generated by the coaxial distance powered zone.

Figures 12C, 12D:
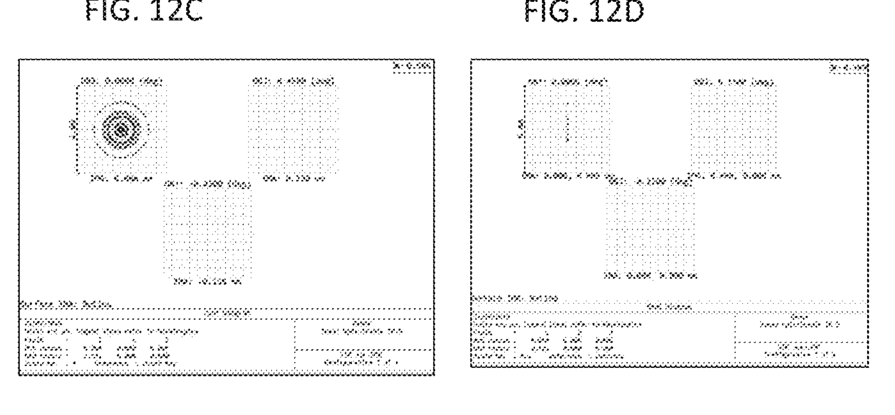

FIG. 12C illustrates the spot diagram and RMS values of the focal point DF1 of the distance object point OP1 formed at the retinal plane by the bifocal contact lens of FIG. 11B having laterally separated optics for distance and near optical zones. DF1 has an RMS size of 0.7 um. These values are approximately similar to that expected of focal points produced by a single vision optical design. However, unlike the cases of lenses configured with coaxial optics such as in FIG. 10A, there is no interaction from the defocused light rays of object points OP2 and OP3 formed by the near zone (RMS values=0). The focal point DF1 does not have defocused light rays from adjacent object points overlaying and increasing the RMS spot size and so the overall average RMS values remain small at 0.7 um for the lens configured with laterally separated foci. Likewise, DF2 and DF3 are also similarly not impacted by defocused light from adjacent object points. Therefore, the laterally separated optics described herein show improved sharpness and/or higher image quality than the coaxial based designs of FIG. 10A.

FIG. 12D illustrates the spot diagram and RMS values of the near focal point N-F1 of the near object point OP1 formed at the retinal plane by the bifocal contact lens of FIG. 11B. NF1 has an RMS size of 0.05 um. However, unlike the cases of lenses configured with coaxial optics such as in FIG. 10A, there may not be an interaction from the defocused light rays of near object points OP2 and OP3 formed by the distance zone (RMS values=0.0). The focal point NF1 has no defocused light rays from adjacent object points overlaying and increasing the RMS spot size and so the overall average RMS values remain small at 0.05 um for the lens configured with a laterally separated near focal ring. Likewise, NF2 and NF3 are also not impacted by defocused light from adjacent object points. Therefore, the laterally separated optics described herein show much improved sharpness and/or higher image quality than the coaxial based designs of FIG. 10*a*.

Figures 13, 14:
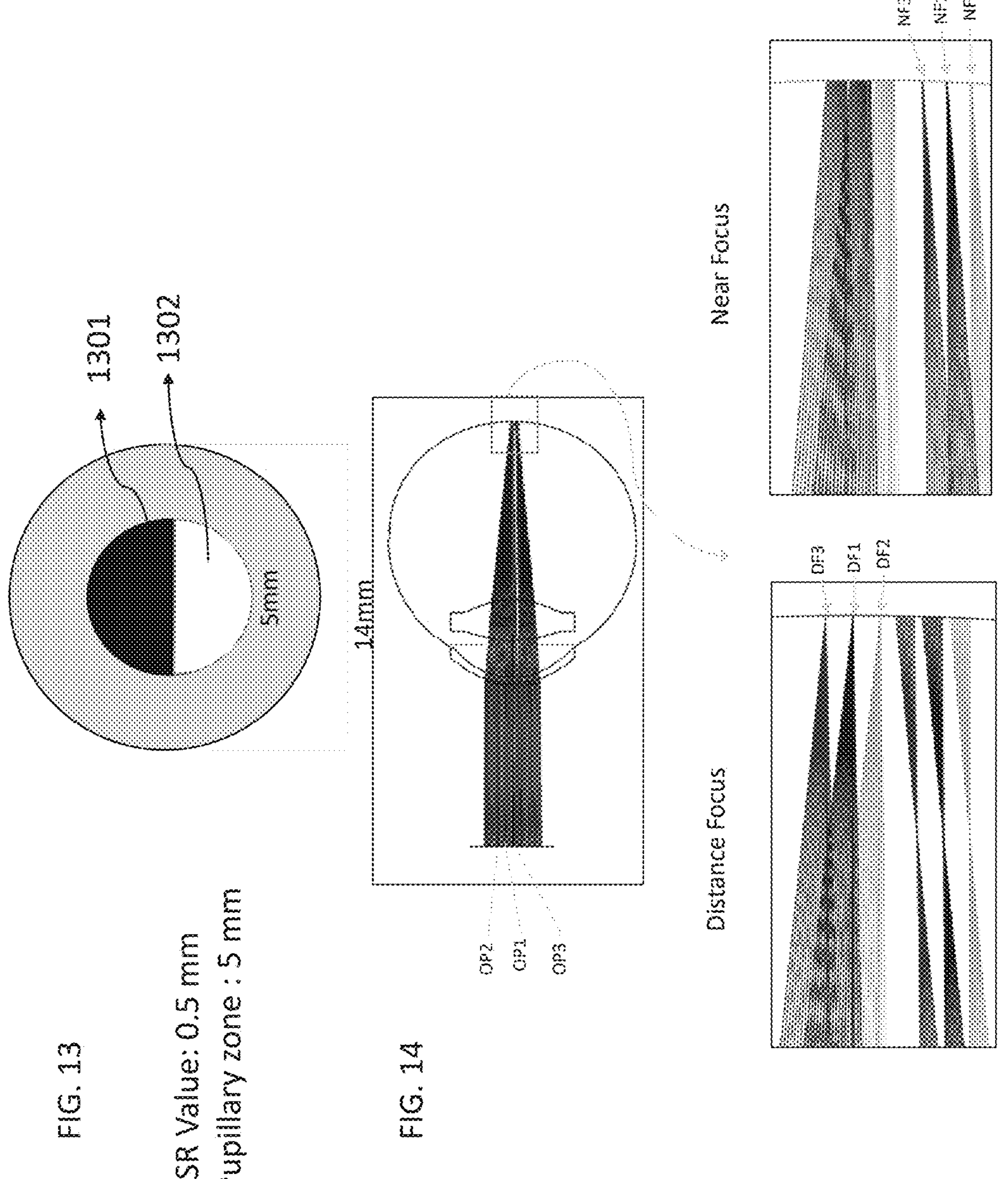
FIG. 13 is a schematic drawing showing a plan view of an ophthalmic lens (e.g., soft bifocal contact lens) comprising laterally separated optics for distance and near optical zones in accordance with certain embodiments.
FIG. 14 is a schematic drawing showing ray tracing of a distance object and a near object imaged through the ophthalmic lenses of FIG. 13 in accordance with certain embodiments.

FIG. 13 is a schematic drawing showing a plan view of an ophthalmic lens (e.g., soft bifocal contact lens) comprising laterally separated optics for distance and near optical zones in accordance with certain embodiments. FIG. 13 illustrates a plan view of a soft bifocal contact lens with laterally separated optics for distance and near optical zones. In this example, both the distance 1301 and near powered 1302 zones have been configured with a single focal point with their optical axes configured to be laterally separated by 0.5 mm. This example differs from the example of FIG. 12B where the lateral separation of the near optical axes was configured to form a ring of near focus separated from and surrounding the distance optical axis. The near zone has a power of +2.5 D. The lens of FIG. 13 has also been configured such that the near focal point has been laterally separated or displaced downward relative to the distance focal point. The plan view shows the optical zone split into two hemispheres, a superior zone and an inferior zone.

FIG. 14 is a schematic drawing showing ray tracing of a distance object and a near object imaged through the ophthalmic lenses of FIG. 13 in accordance with certain embodiments. FIG. 14 also illustrates a higher magnification inset of the ray tracing formed when the distance object is in focus at the retinal plane (distance focus) and when the near object is in focus at the image plane (near focus). In the respective illustrations, light rays passing through the respective out-of-focus zones are represented as an out-of-focus blur circle at the image plane. The distance object in FIG. 14 has been further defined by three points; a central object point 1 (OP1) on axis and points 2 and 3 (OP2 and OP3) positioned 0.5 degree either side of OP1. Likewise, the near object in FIG. 14*b* has been further defined by 3 points; a central object point 1 (OP1) on axis and points 2 and 3 (OP2 and OP3) positioned 0.15 degree on either side of OP1.

As illustrated in the distance focus chart, the focal points of the distance object OP1, OP2 and OP3 as DF1, DF2 and DF3 are at the image plane and, the out-of-focus rays of OP1, OP2 and OP3 passing through the near addition zone make up the remaining light rays falling at the image plane (below the in focus distance object points). The near focus chart illustrates the focal points of a near object OP1, OP2 and OP3 as NF1, NF2 and NF3 at the image plane and the out-of-focus rays of OP1, OP2 and OP3 passing through the distance vision zone make up the remaining light rays falling above the near focal points at the image plane. The ray tracing in FIG. 14 illustrates the absence of interactions between the out-of-focus light rays of object points OP1, OP2 and OP3 and the in-focus images of OP1, OP2 and OP3 produced by the distance and/or near powered zone(s) in this example of a laterally separated ring bifocal contact lens designs.

FIGS. 15A and 15B are schematic drawings showing spot diagrams and RMS values of the focal point, DF1 and NF1, of object point OP1 formed at the retinal plane by the ophthalmic lens of FIG. 13 in accordance with certain embodiments.

FIG. 15A illustrates a spot diagram and RMS values of the focal point DF1 of the distance object point OP1 formed at the retinal plane by the bifocal contact lens of FIG. 13 having laterally separated optics for distance and near optical zones. In this example, DF1 has an RMS size of 2.16 um. These values are approximately similar to that expected of focal points produced by a single vision optical design. However, unlike the cases of lenses configured with coaxial optics such as in FIG. 10A, there may not be an interaction from the defocused light rays of object points OP2 and OP3 formed by the near zone (RMS values=0). The focal point DF1 does not have defocused light rays from adjacent object points overlaying and increasing the RMS spot size and so the overall average RMS values remain small at 2.16 um for the exemplary lens configured with laterally separated foci. Likewise, DF2 and DF3 may also similarly not be impacted by defocused light from adjacent object points.

FIG. 15B illustrates a spot diagram and RMS values of the near focal point NF1 of the near object point OP1 formed at the retinal plane by the bifocal contact lens of FIG. 13. In this example, NF1 has an RMS size of 1.80 um. These values are similar to that expected of focal points produced by a single vision optical design. However, unlike the cases of lenses configured with coaxial optics such as in FIG. 10A, there may not be an interaction from the defocused light rays of near object points OP2 and OP3 formed by the distance zone (RMS values=0). The focal point NF1 may not have defocused light rays from adjacent object points overlaying and increasing the RMS spot size and so the overall average RMS values remain small at 1.8 um for the lens configured with a laterally separated near focal point. Likewise, NF2 and NF3 may also similarly not be impacted by defocused light from adjacent object points.

Therefore, the lens of FIG. 15 (e.g., FIGS. 13-15) configured with laterally separated optics described herein show improved sharpness and higher distance and near image quality.

FIG. 16 is a schematic drawing illustrating an exemplary design of an ophthalmic lens using spherical geometry in accordance with certain embodiments. In some embodiments, to reduce the discontinuity between the two optical zones as in the embodiment illustrated in FIG. 13, an ophthalmic lens 700 may be created utilizing two spheres

702, 704. The spheres 702, 704 have varying diameters (with diameter of sphere 702 larger than sphere 704) and may intersect at a boundary 706. An optic zone 708 is defined and includes a first optical zone 710 and a second optical zone 712. The properties of the first optical zone 710 are defined by the sphere 702 and the properties of the second optical zone 712 are defined by the sphere 704. Since the spheres intersect at the junction 706, there may be reduced discontinuity and may reduce the need for blending (e.g., a blending zone). In some embodiments, no blending zone may be present. The resulting lens 700 may be characterized using several parameters. In some embodiments, the first optical zone 710 comprises a first optical power and the second optical zone 712 comprises a second optical power different from the first optical power. In some embodiments, the first optical zone comprises a first optical power and the second optical zone comprises a second optical power relatively more positive than the first optical power. In some embodiments, the first optical zone comprises a first optical power and the second optical zone comprises a second optical power relatively more positive than the first optical power by approximately +0.25 D to approximately +3 D. In some embodiments, the second optical zone comprises a second optical power relatively more positive than the first optical power by approximately +0.25 D to +2.5 D, approximately +0.25 D to +2 D, approximately +0.25 D to +1.5 D, approximately +0.25 D to +1 D and approximately +0.25 D to +0.5 D. In some embodiments, the first optical zone comprises a first optical power and the second optical zone comprises a second optical power relatively more positive than the first optical power by approximately +3 D or more. In some embodiments, the first optical zone comprises a first optical power and the second optical zone comprises a second optical power relatively less positive than the first optical power. In some embodiments, the first optical zone comprises a first optical power and the second optical zone comprises a second optical power relatively more positive than the first optical power by approximately −0.25 D to approximately −3 D. In some embodiments, the first optical zone may occupy an upper portion of the ophthalmic lens. In some embodiments, the second optical zone may occupy a lower portion of the ophthalmic lens. In some embodiments, the first optical zone may be configured to correct one of distance, intermediate, or near vision; and/or the second optical zone may be configured to correct a different one of distance, intermediate, or near vision. In some embodiments, the first optical zone may be configured to correct distance vision and the second optical zones may be configured to correct near vision. In some embodiments, the first optical zone may be configured to correct near vision and the second optical zone may be configured to correct distance vision. With the utilization of the two spheres 702 and 704 and radii of the first optical zone and the second optical zone not intersecting along the surface of the lens, the images are optically separated (e.g., laterally displaced), and therefore, the resultant RMS spot size of the retinal image may be reduced.

Figures 17, 18:
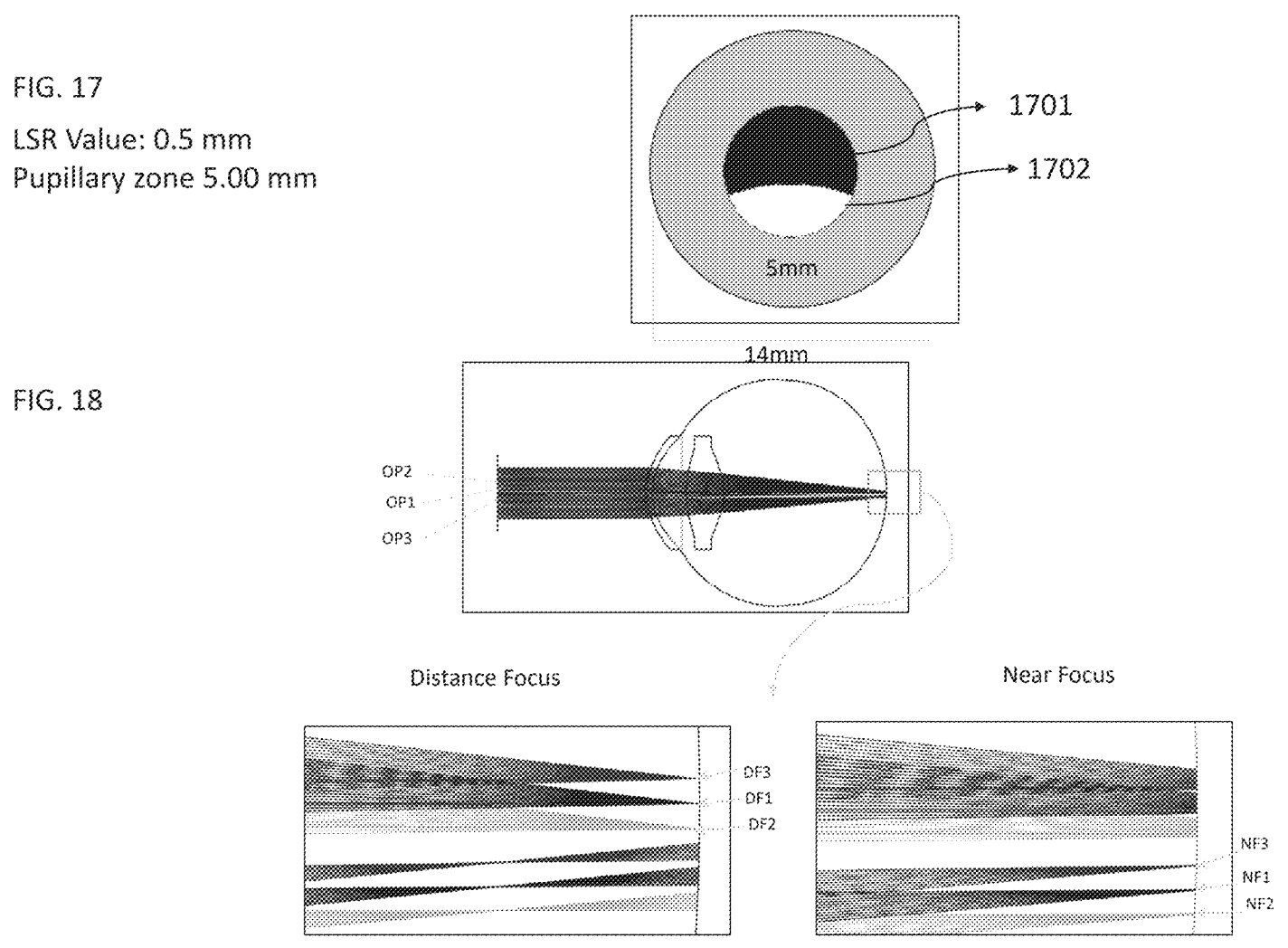

FIG. 17 is a schematic drawing showing a plan view of an ophthalmic lens (e.g., soft bifocal contact lens) comprising laterally separated optics for distance and near optical zones in accordance with certain embodiments. FIG. 17 shows a plan view of a soft bifocal contact lens configured with laterally separated optics for distance and near optical zones. In this example, both the distance 1701 and near powered 1702 zones have been configured with a single focal point with their optical axes configured to be laterally separated by 0.5 mm. The near addition has a power of +2.5 D. This example lens is configured so that the near focal point is laterally separated inferiorly. The plan view shows the optical zone split into two hemispheres, a superior zone and an inferior zone. This example differs from the example of FIG. 13 where the lateral separation of the near optical axis was configured without modification of the junction between the laterally separated distance and near optical zones. The intersection of the two zones in the lens of FIG. 17 is curved and has been configured so that the junction between the distance and near zones is substantially seamless and/or substantially junction less. The improved junction has been achieved by the use of spherical surface curvatures discussed in this disclosure. In some embodiments, spherical surface curvatures may be utilized without utilizing a substantially seamless and/or substantially junction less configuration (e.g., a blending zone or step may still be utilized).

FIG. 18 is a schematic drawing showing ray tracing of a distance object and a near object imaged through the ophthalmic lenses of FIG. 17 in accordance with certain embodiments. FIG. 18 also provides a higher magnification inset of the ray tracing formed when the distance object is in focus at the retinal plane (distance focus) and when the near object is in focus at the retinal plane (near focus). In the respective figures, defocused light rays passing through the zones not in focus are represented as an out-of-focus blur circle at the image plane. The distance object has been further defined by three points; a central object point 1 (OP1) on axis and points 2 and 3 (OP2 and OP3) positioned 0.5 degrees apart on either side of OP1. Likewise the near object in FIG. 18 has been further defined by three points; a central object point 1 (OP1) on axis and points 2 and 3 (OP2 and OP3) positioned 0.15 degrees apart on either side of OP1.

The distance focus chart in FIG. 18 illustrates the focal points of the distance object OP1, OP2 and OP3 as DF1, DF2 and DF3 at the image plane and the out-of-focus rays of OP1, OP2 and OP3 passing through the near addition zone make up the remaining light rays falling at the image plane (below the in focus distance object points). The near focus chart shows the focal points of a near object OP1, OP2 and OP3 as NF1, NF2 and NF3 at the image plane and the out-of-focus rays of OP1, OP2 and OP3 passing through the distance vision zone make up the remaining light rays falling above the near focal points at the image plane. FIG. 18 illustrates the absence of the interactions between the out-of-focus light rays of object points OP1, OP2 and OP3 and the in focus images of OP1, OP2 and OP3 produced by the distance or near powered zone(s) in these laterally separated bifocal contact lens designs.

FIGS. 19A and 19B are schematic drawings showing spot diagrams and RMS values of the focal point, DF1 and NF1, of object point OP1 formed at the retinal plane by the ophthalmic lens of FIG. 17 in accordance with certain embodiments.

FIG. 19A illustrates a spot diagram and RMS values of the focal point DF1 of the distance object point OP1 formed at the retinal plane by the bifocal contact lens of FIG. 17 having laterally separated optics for distance and near optical zones. In this example, DF1 has an RMS size of 2.32 um. These values are approximately similar to that of focal points produced by a single vision optical design. However, unlike the cases of lenses configured with coaxial optics such as in FIG. 10A, there may not be an interaction from the defocused light rays of object points OP2 and OP3 formed by the near zone (RMS values=0). The focal point DF1 does not have defocused light rays from adjacent object points overlaying and increasing the RMS spot size and so the overall average RMS values remain small at 2.32 um for the lens configured with laterally separated foci. Likewise, DF2 and DF3 may also similarly not be impacted by defocused light from adjacent object points.

FIG. 19B illustrates a spot diagram and RMS values of the near focal point NF1 of the near object point OP1 formed at the retinal plane by the bifocal contact lens of FIG. 17. In this example, NF1 has an RMS size of 1.98 um. These values are similar to that of focal points produced by a single vision optical design. However, unlike the cases of lenses configured with coaxial optics such as in FIG. 10*a*, there may not be an interaction from the defocused light rays of near object points OP2 and OP3 formed by the distance zone (RMS values=0). The focal point NF1 does not have defocused light rays from adjacent object points overlaying and increasing the RMS spot size and so the overall average RMS values remain small at 1.98 um for the lens configured with a laterally separated near focal point. Likewise, NF2 and NF3 may also similarly not be impacted by defocused light from adjacent object points.

Therefore, the lens of FIG. 17 configured with laterally separated optics show improved sharpness and higher distance and near image quality than the coaxial based designs of FIG. 10A. Further examples of introducing laterally separated optics geometry into a contact or spectacle lens may include: (1) designing a partial overlap of object images, (2) introducing lateral separation of both the distance and near optical portions in equal or unequal amounts and in the same or opposite directions or other relative direction or amount independently. Furthermore, varying the lateral separation may influence the shape of the junction between the two optical zones with relatively smaller separations resulting in relatively more curved junction and relatively larger separations resulting in relatively less curved junctions.

Figures 20, 21:
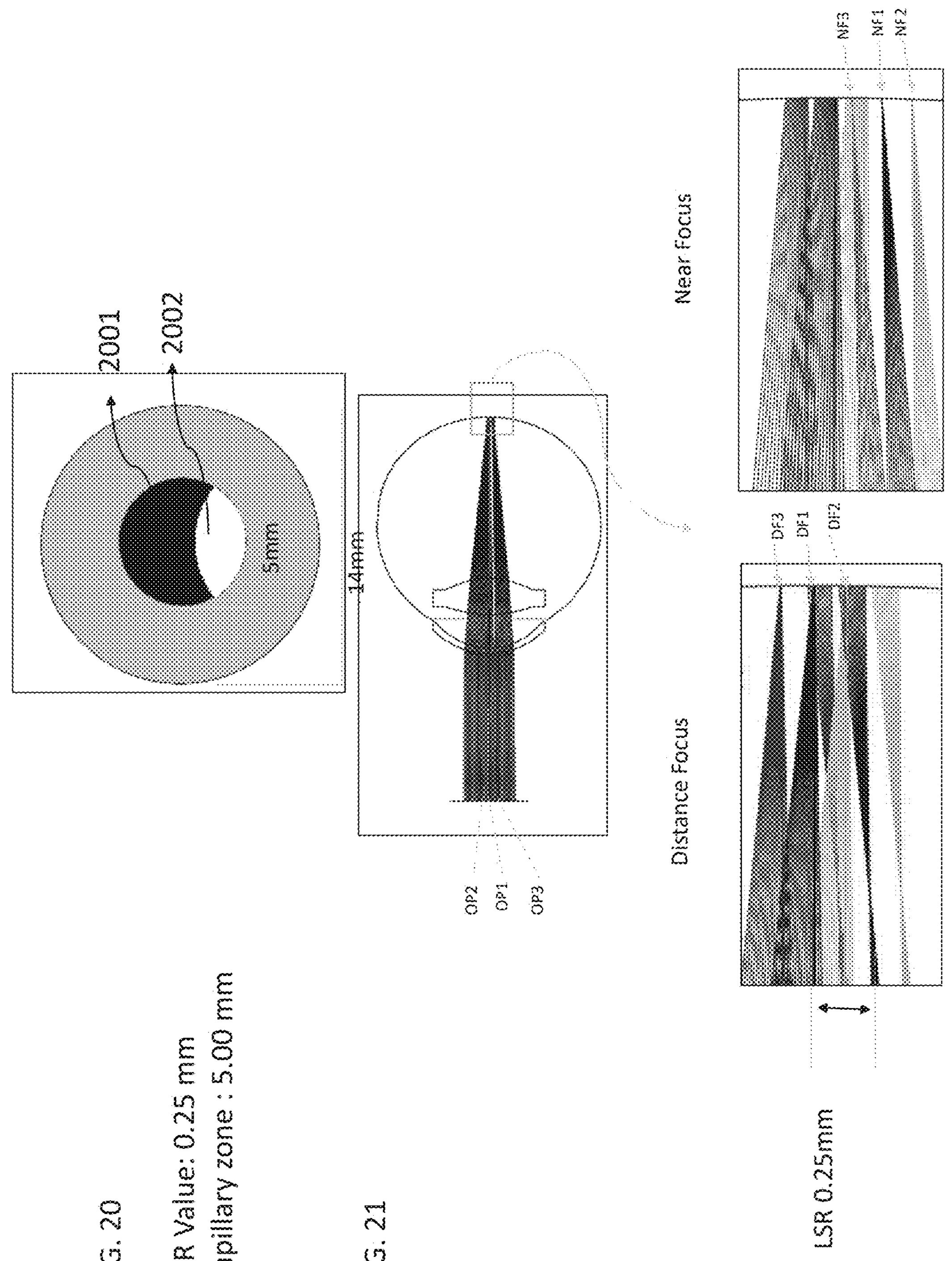
FIG. 20 is a schematic drawing showing a plan view of an ophthalmic lens (e.g., soft bifocal contact lens) comprising laterally separated optics for distance and near optical zones in accordance with certain embodiments.
FIG. 21 is a schematic drawing showing ray tracing of a distance object and a near object imaged through the ophthalmic lenses of FIG. 20 in accordance with certain embodiments.

FIG. 20 is a schematic drawing showing a plan view of an ophthalmic lens (e.g., soft bifocal contact lens) comprising laterally separated optics for distance and near optical zones in accordance with certain embodiments. In this example, both the distance 2001 and near 2002 powered zones have been configured with a single focal point with their optical axes configured to be laterally separated by 0.25 mm. The near addition has a power of +2.5 D. This exemplary lens is configured so that the near focal point is laterally separated inferiorly. The plan view shows the optical zone split into two hemispheres, a superior zone and an inferior zone. This example differs from the example of FIG. 13 where the lateral separation of the near optical axis was configured with a junction less connection between the laterally separated distance and near optical zones. The intersection of the two zones in the lens of FIG. 20 is curved and has been configured so that the junction between the distance and near zones is substantially seamless and/or substantially junction less. The improved junction has been achieved by the use of spherical surface curvatures.

FIG. 21 is a schematic drawing showing ray tracing of a distance object and a near object imaged through the ophthalmic lenses of FIG. 20 in accordance with certain embodiments. FIG. 21 also provides a higher magnification inset of the ray tracing formed when the distance object is in focus at the retinal plane (distance focus) and when the near object is in focus at the retinal plane (near focus). In the respective figure defocused light rays passing through the zones not in focus are represented as an out-of-focus blur circle at the image plane. The distance object in in the distance focus chart has been further defined by three points; a central object point 1 (OP1) on axis and points 2 and 3 (OP2 and OP3) positioned 0.5 degrees apart on either side of OP1. Likewise, the near object in the near focus chart has been further defined by three points; a central object point 1 (OP1) on axis and points 2 and 3 (OP2 and OP3) positioned 0.15 degrees apart on either side of OP1.

The distance focus chart illustrates the focal points of the distance object OP1, OP2 and OP3 as DF1, DF2 and DF3 at the image plane and, the out-of-focus rays of OP1, OP2 and OP3 passing through the near addition zone make up the remaining light rays falling at the image plane (below the in focus distance object points). The near focus chart illustrates the focal points of a near object OP1, OP2 and OP3 as NF1, NF2 and NF3 at the image plane and the out-of-focus rays of OP1, OP2 and OP3 passing through the distance vision zone make up the remaining light rays falling above the near focal points at the image plane. FIG. 21 illustrates interactions between the out-of-focus light rays of the distance object points through the near zone on DF-1 and DF-2 but not DF-3 while the near focus chart shows interactions between the out-of-focus light rays of the near object points through the distance zone on NF-3 by the distance powered zone in these laterally separated bifocal contact lens designs.

FIGS. 22A and 22B are schematic drawings showing spot diagrams and RMS values of the focal point, DF1 and NF1, of object point OP1 formed at the retinal plane by the ophthalmic lens of FIG. 20 in accordance with certain embodiments.

FIG. 22A illustrates a spot diagram and RMS values of the focal point DF1 of the distance object point OP1 formed at the retinal plane by the bifocal contact lens of FIG. 20 having laterally separated optics for distance and near optical zones. In this example, DF1 has an RMS size of 1.93 um. These values are approximately similar to that of focal points produced by a single vision optical design. However, unlike the cases of lenses configured with larger laterally separated focal points of FIG. 17, there is some interaction from the defocused light rays of object point OP3 formed by the near zone on DF-1 (RMS values=162.6 um) but not from OP2 on DF-1 (0 um). Therefore, overall blurring of the focal point D-F1 may still be affected by defocused light rays from adjacent object points overlaying and increasing the RMS spot size (overall average RMS values 93.88 um) for this lens configured with laterally separated foci. The ray tracing also indicates D-F2 is also similarly impacted by defocused light from adjacent object points but DF-3 is not.

FIG. 22B illustrates a spot diagram and RMS values of the near focal point NF1 of the near object point OP1 formed at the retinal plane by the bifocal contact lens of FIG. 20. NF1 has an RMS size of 1.84 um. These values are similar to that of focal points produced by a single vision optical design. However, unlike when focusing distance objects as in FIG. 22A, there is may not be an interaction from the defocused light rays of near object points OP2 and OP3 formed by the distance zone (RMS values=0). The focal point NF1 does not have defocused light rays from adjacent object points overlaying and increasing the RMS spot size and so the overall average RMS values remain small at 1.84 um for the lens configured with a laterally separated near focal point.

Therefore, the lens of FIG. 20 illustrates that lenses configured with laterally separated optics described herein may differentially manipulate the image quality between distance and near focus.

Figures 23, 24:
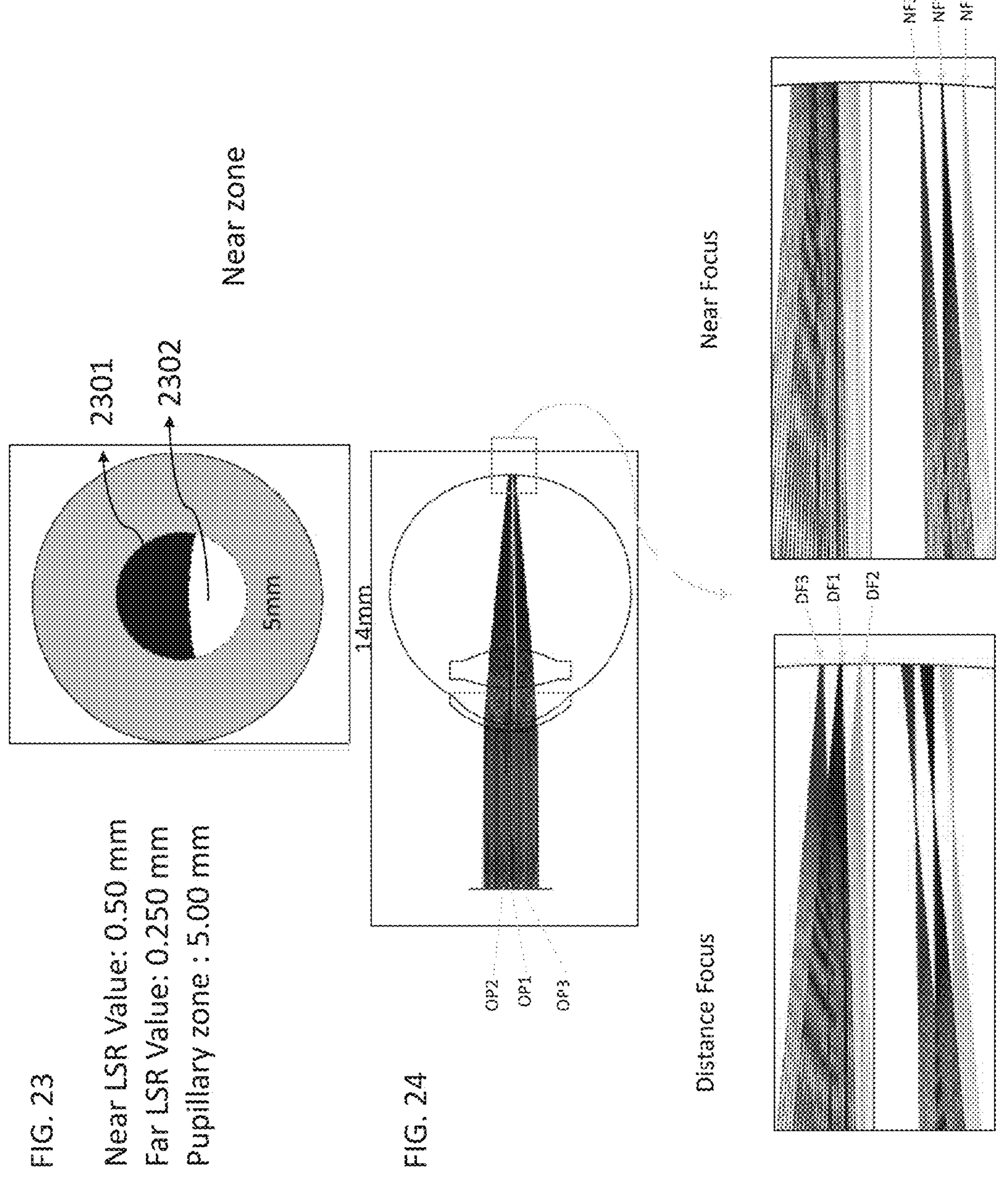
FIG. 23 is a schematic drawing showing a plan view of an ophthalmic lens (e.g., soft bifocal contact lens) comprising laterally separated optics for distance and near optical zones in accordance with certain embodiments.
FIG. 24 is a schematic drawing showing ray tracing of a distance object and a near object imaged through the ophthalmic lenses of FIG. 23 in accordance with certain embodiments.
Figures 26, 27:
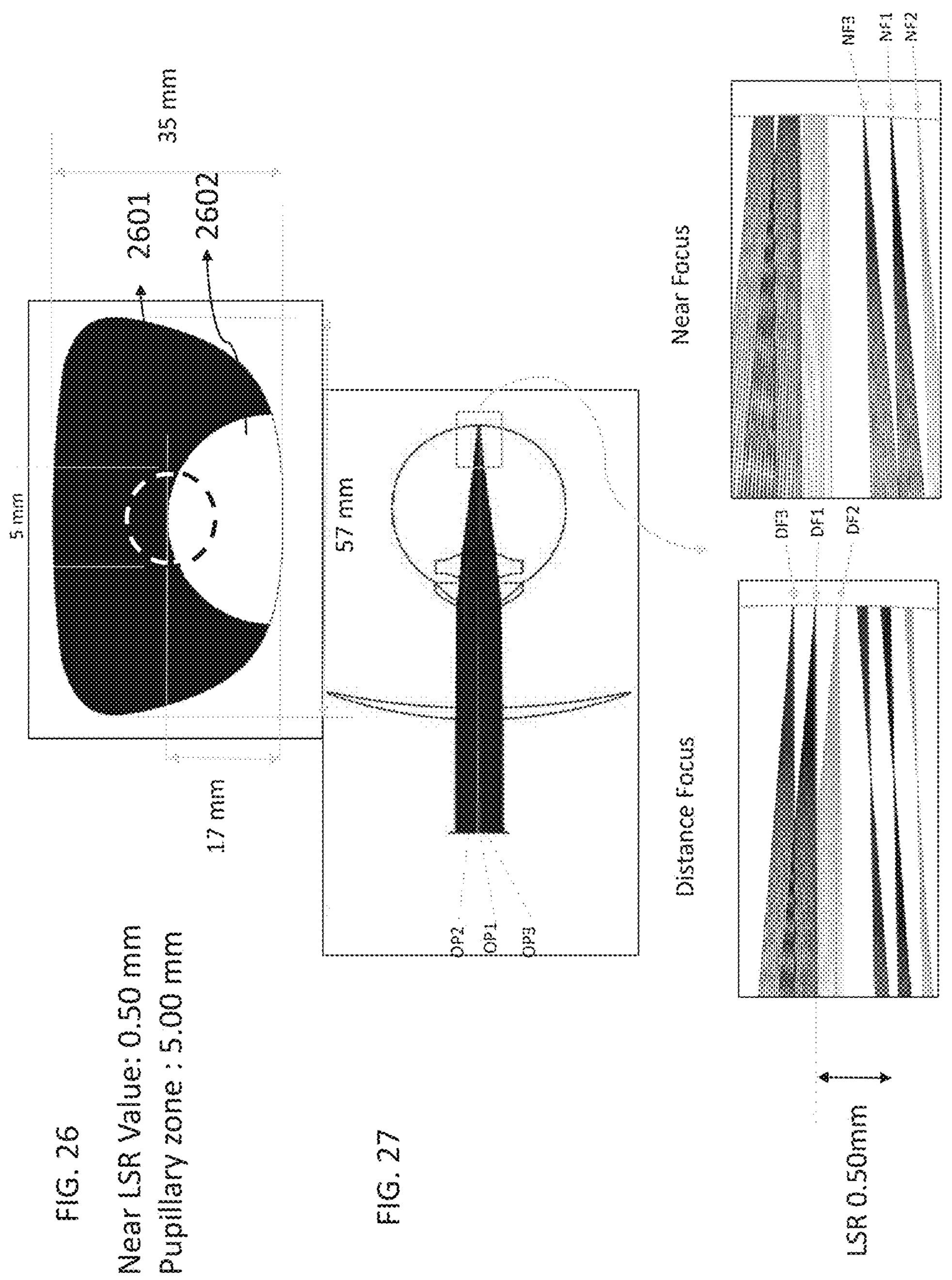
FIG. 26 is a schematic drawing showing a plan view of an ophthalmic lens (e.g., bifocal spectacle lens) comprising laterally separated optics for distance and near optical zones in accordance with certain embodiments.
FIG. 27 is a schematic drawing showing ray tracing of a distance object and a near object imaged through the ophthalmic lenses of FIG. 26 in accordance with certain embodiments.

FIG. 23 is a schematic drawing showing a plan view of an ophthalmic lens (e.g., soft bifocal contact lens) comprising laterally separated optics for distance and near optical zones in accordance with certain embodiments. In this example, both the distance 2301 and near 2302 powered zones have been configured with a single focal point with their distance and near optical axes configured to be laterally separated by 0.25 mm inferiorly and 0.50 mm superiorly from the optical center of the contact lens. The near addition has a power of +2.5 D. This exemplary lens is configured so that the near focal point is located inferiorly. The plan view shows the optical zone split into two hemispheres, a superior zone and an inferior zone. This example differs from the example of FIG. 13 where the lateral separation of the near optical axis was configured without modification of the junction between the laterally separated distance and near optical zones. The intersection of the two zones in the lens of FIG. 26 is curved and has been configured so that the junction between the distance and near zones is substantially seamless and/or substantially junction less. The improved junction has been achieved by the use of spherical surface curvatures.

FIG. 24 is a schematic drawing showing ray tracing of a distance object and a near object imaged through the ophthalmic lenses of FIG. 23. FIG. 24 also provides a higher magnification inset of the ray tracing formed when the distance object is in focus at the retinal plane (distance focus) and when the near object is in focus at the retinal plane (near focus). In the respective figures defocused light rays passing through the zones not in focus are represented as an out-of-focus blur circle at the image plane. The distance object in the distance focus chart has been further defined by three points; a central object point 1 (OP1) on axis and points 2 and 3 (OP2 and OP3) positioned 0.5 degrees apart on either side of OP1. Likewise, the near object in FIG. 24 has been further defined by three points; a central object point 1 (OP1) on axis and points 2 and 3 (OP2 and OP3) positioned 0.15 degrees apart on either side of OP1.

The distance focus chart illustrates the focal points of the distance object OP1, OP2 and OP3 as DF1, DF2 and DF3 at the image plane, and the out-of-focus rays of OP1, OP2 and OP3 passing through the near addition zone make up the remaining light rays falling at the image plane (below the in focus distance object points). The near focus chart illustrates the focal points of a near object OP1, OP2 and OP3 as NF1, NF2 and NF3 at the image plane and the out-of-focus rays of OP1, OP2 and OP3 passing through the distance vision zone make up the remaining light rays falling above the near focal points at the image plane. FIG. 24 illustrates the absence of interactions between the out-of-focus light rays of object points OP1, OP2 and OP3 and the in focus images of OP1, OP2 and OP3 produced by the distance or near powered zone(s) in these laterally separated bifocal contact lens designs.

FIGS. 25A and 25B are schematic drawings showing spot diagrams and RMS values of the focal point, DF1 and NF1, of object point OP1 formed at the retinal plane by the ophthalmic lens of FIG. 23 in accordance with certain embodiments.

FIG. 25A illustrates a spot diagram and RMS values of the focal point D-F1 of the distance object point OP1 formed at the retinal plane by the bifocal contact lens of FIG. 17 having laterally separated optics for distance and near optical zones. In this example, DF1 has an RMS size of 5.71 um. These values are approximately similar to that expected of focal points produced by a single vision optical design. However, unlike the cases of lenses configured with coaxial optics such as in FIG. 10A, there may not be an interaction from the defocused light rays of object points OP2 and OP3 formed by the near zone (RMS values=0). The focal point DF1 does not have defocused light rays from adjacent object points overlaying and increasing the RMS spot size and so the overall average RMS values remain small at 5.71 um for the lens configured with laterally separated foci. Likewise, D-F2 and D-F3 may also similarly not be impacted by defocused light from adjacent object points.

FIG. 25B illustrates a spot diagram and RMS values of the near focal point N-F1 of the near object point OP1 formed at the retinal plane by the bifocal contact lens of FIG. 23. In this example, NF1 has an RMS size of 2.01 um. These values are similar to that of focal points produced by a single vision optical design. However, unlike the cases of lenses configured with coaxial optics such as in FIG. 10A, there may not be an interaction from the defocused light rays of near object points OP2 and OP3 formed by the distance zone (RMS values=0). The focal point NF1 does not have defocused light rays from adjacent object points overlaying and increasing the RMS spot size and so the overall average RMS values remain small at 2.01 um for the lens configured with a laterally separated near focal point. Likewise, NF2 and NF3 may also similarly not be impacted by defocused light from adjacent object points.

Therefore, the lens of FIG. 23 configured with distance and near focal points laterally separated by different amounts may still maintain improved sharpness and higher distance and near image quality than coaxial based designs of e.g., FIG. 10A.

FIG. 26 is a schematic drawing showing a plan view of an ophthalmic lens (e.g., bifocal spectacle lens) comprising laterally separated optics for distance and near optical zones in accordance with certain embodiments. In this example, both the distance 2601 and near 2602 powered zones have been configured with a single focal point with their optical axes configured to be laterally separated by 0.5 mm. The near addition has a power of +2.5 D. The lens of FIG. 26 has also been configured such that the near focal point has been laterally separated or displaced downward. The plan view shows the optical zone split into two regions, a superior zone and an inferior zone. Like the contact lens described in FIG. 23, this spectacle lens example is configured so that the junction between the distance and near zones is substantially seamless and/or substantially junction less. The improved junction has been achieved by the use of spherical front surface curvatures and in this example the junction may be nonlinear due to the selection of the lateral and downward separation of the near focal point by 0.5 mm.

FIG. 27 is a schematic drawing showing ray tracing of a distance object and a near object imaged through the ophthalmic lenses of FIG. 26 in accordance with certain embodiments. FIG. 27 also provides higher magnification insets of the ray tracing formed when the distance object is in focus at the retinal plane (distance focus) and when the near object is in focus at the retinal plane (near focus). In the respective figures light rays passing through the respective out-of-focus zones are represented as an out-of-focus blur circle at the image plane. The distance object in the distance focus chart has been further defined by three points; a central object point 1 (OP1) on axis and points 2 and 3 (OP2 and OP3) positioned 0.50 degrees apart on either side of OP1. Likewise, the near object in in the near focus chart has been further defined by three points; a central object point 1 (OP1) on axis and points 2 and 3 (OP2 and OP3) positioned 0.15 degrees apart on either side of OP1.

The distance focus chart illustrates the focal points of the distance object OP1, OP2 and OP3 as DF1, DF2 and DF3 at the image plane and, the out-of-focus rays of OP1, OP2 and OP3 passing through the near addition zone make up the remaining light rays falling at the image plane (below the in focus distance object points). The near focus chart illustrates the focal points of a near object OP1, OP2 and OP3 as NF1, NF2 and NF3 at the image plane and the out-of-focus rays of OP1, OP2 and OP3 passing through the distance vision zone make up the remaining light rays falling above the near focal points at the image plane. FIG. 27 illustrates the absence of interactions between the out-of-focus light rays of object points OP1, OP2 and OP3 and the images of OP1, OP2 and OP3 produced by the distance or near powered zone(s) in these laterally separated ring spectacle lens designs.

FIGS. 28A and 28 are schematic drawings showing spot diagrams and RMS values of the focal point, DF1 and NF1, of object point OP1 formed at the retinal plane by the ophthalmic lens of FIG. 26 in accordance with certain embodiments.

FIG. 28A illustrates a spot diagram and RMS values of the focal point DF1 of the distance object point OP1 formed at the retinal plane by the spectacle lens of FIG. 26 having laterally separated optics for distance and near optical zones sampled over a 5 mm aperture at the spectacle lens plane. In this example, DF1 has an RMS size of 0.49 um. These values are similar to that of focal points produced by a single vision optical design of similar aperture size. However, unlike the cases of lenses configured with coaxial optics such as in FIG. 10A, there may not be an interaction from the defocused light rays of object points OP2 and OP3 formed by the near zone (RMS values=0). The focal point DF1 does not have defocused light rays from adjacent object points overlaying and increasing the RMS spot size and so the overall average RMS values remain small at 0.49 um for the lens configured with laterally separated foci. Likewise, DF2 and DF3 may also similarly not be impacted by defocused light from adjacent object points.

FIG. 28B illustrates a spot diagram and RMS values of the near focal point NF1 of the near object point OP1 formed at the retinal plane by the spectacle lens of FIG. 26. In this example, NF1 has an RMS size of 0.42 um. These values are similar to that expected of focal points produced by a single vision optical design because of the lack of interaction from the defocused light rays of near object points OP2 and OP3 formed by the distance zone (RMS values=0). The focal point NF1 does not have defocused light rays from adjacent object points overlaying and increasing the RMS spot size and so the overall average RMS values remain small at 0.42 um for the lens configured with a laterally separated near focal point. Likewise, NF2 and NF3 may also similarly not be impacted by defocused light from adjacent object points.

Therefore, the spectacle lens of FIG. 26 configured with laterally separated optics described herein show improved sharpness and higher distance and near image quality than the coaxial based designs of e.g., FIG. 10A.

Figure 29A:
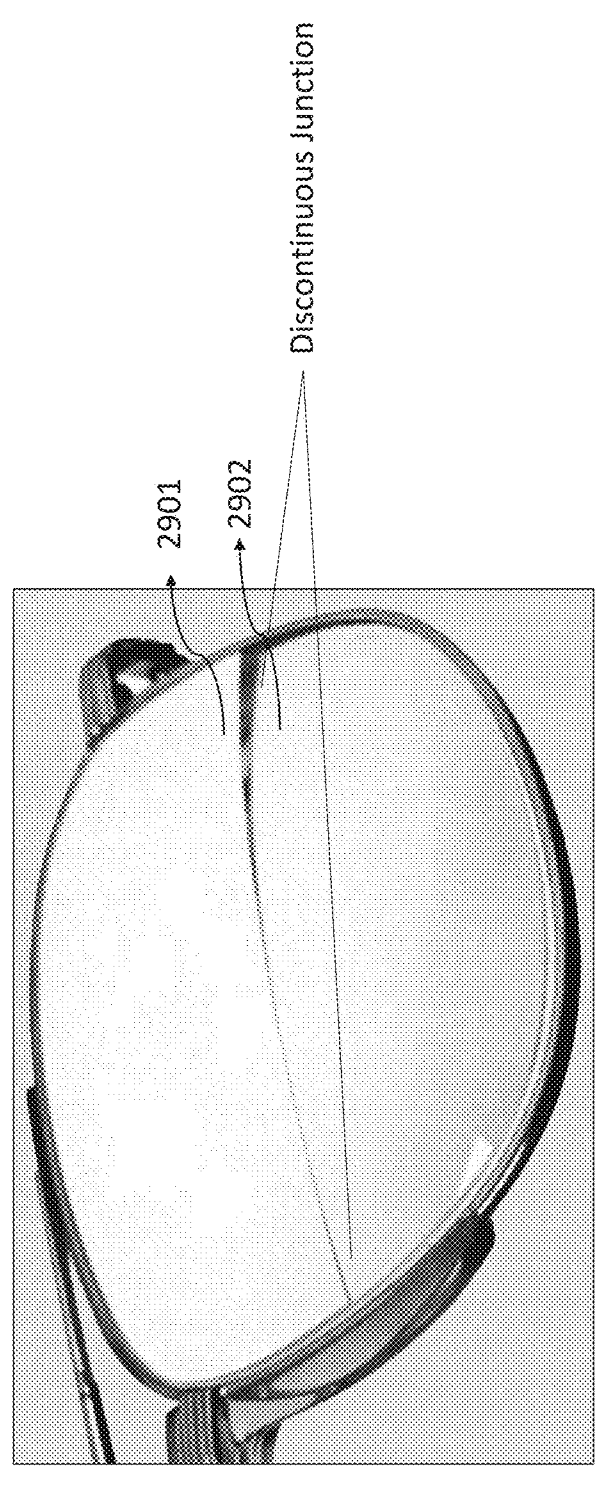
FIG. 29A is a schematic drawing showing a plan view of an executive bifocal spectacle lens.

FIG. 29A is a schematic drawing showing a plan view of an executive bifocal spectacle lens. As illustrated in FIG. 29A, the executive bifocal spectacle lens comprises a discontinuous junction between the distance zone 2901 and the near zone 2902.

Figures 29B, 30:
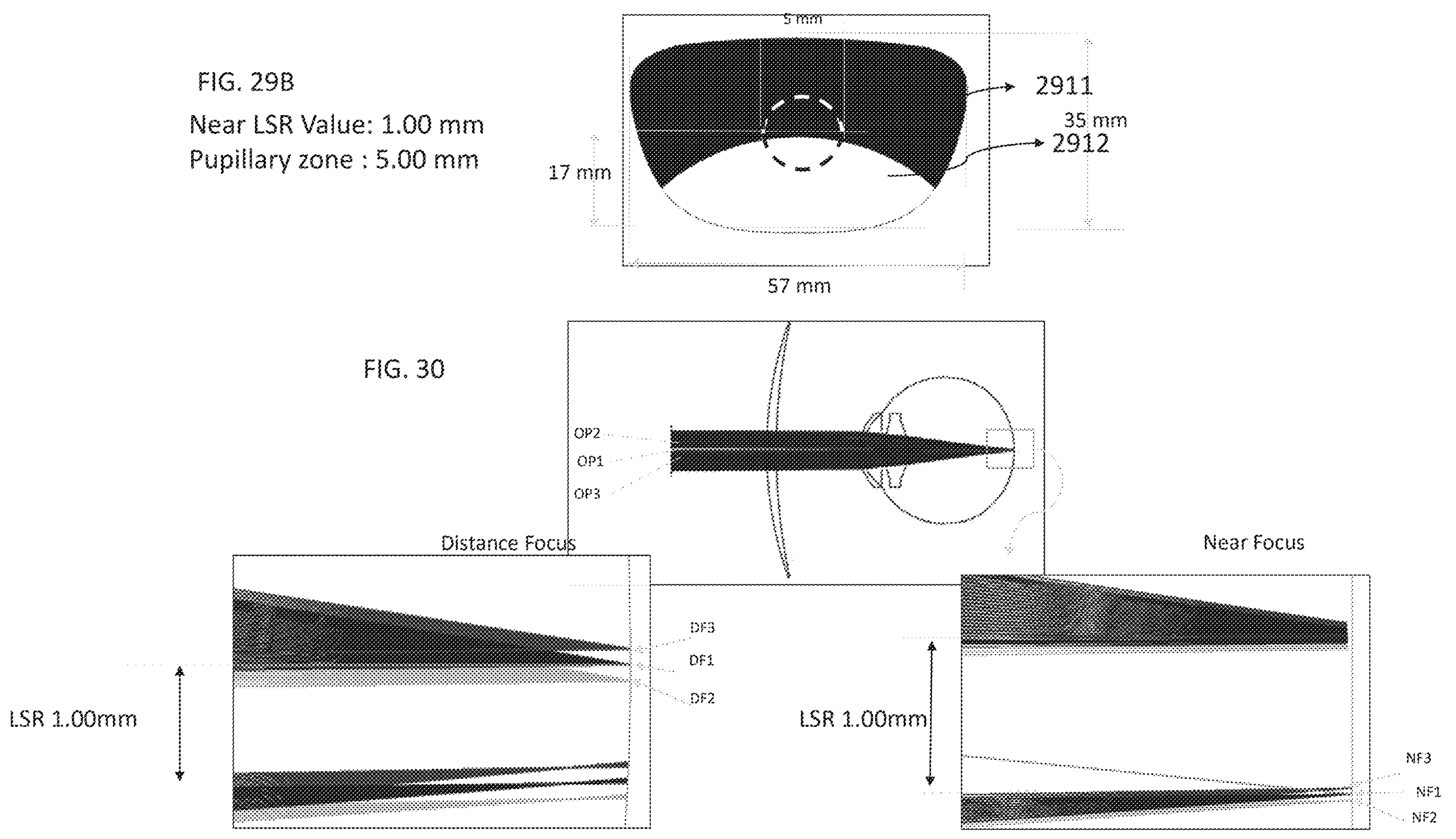
FIG. 29B is a schematic drawing showing a plan view of an ophthalmic lens (e.g., bifocal spectacle lens) comprising laterally separated optics for distance and near optical zones in accordance with certain embodiments.
FIG. 30 is a schematic drawing showing ray tracing of a distance object and a near object imaged through the ophthalmic lenses of FIG. 29B in accordance with certain embodiments.

FIG. 29B is a schematic drawing showing a plan view of an ophthalmic lens (e.g., bifocal spectacle lens) comprising laterally separated optics for distance 2911 and near 2912 optical zones in accordance with certain embodiments. In this example, both the distance and near powered zones have been configured with a single focal point with their optical axes configured to be laterally separated by 1 mm. The near addition has a power of +2.5 D. The lens of FIG. 29B has also been configured such that the near focal point is laterally separated or displaced downward. The plan view shows the optical zone split into two regions, a superior zone and an inferior zone. Like the spectacle lens described in FIG. 26, this spectacle lens example of FIG. 29B was also configured so that the junction between the distance and near zones is substantially seamless and/or substantially junction less. The improved junction may be achieved by the use of spherical front surface curvatures, and in this example the junction may be nonlinear due to the selection of the lateral and downward separation of the near focal point by 1 mm. However, compared to the example shown in FIG. 26, with a lateral separation value of 0.5 mm, the lens of FIG. 29B with a lateral separation value of 1 mm has enabled the junction between the distance and near zones to be less curved and the near zone of the spectacle lens to be widened to increase the field of view through the near zone.

FIG. 30 is a schematic drawing showing ray tracing of a distance object and a near object imaged through the ophthalmic lenses of FIG. 29B in accordance with certain embodiments. FIG. 30 also provides higher magnification insets of the ray tracing formed when the distance object is in focus at the retinal plane (distance focus) and when the near object is in focus at the retinal plane (near focus). In the respective figures, light rays passing through the respective out-of-focus zones are represented as an out-of-focus blur circle at the image plane. The distance object in the distance focus inset has been further defined by three points; a central object point 1 (OP1) on axis and points 2 and 3 (OP2 and OP3) positioned 0.50 degrees apart on either side of OP1. Likewise, the near object in the near focus inset has been further defined by three points; a central object point 1 (OP1) on axis and points 2 and 3 (OP2 and OP3) positioned 0.15 degrees apart on either side of OP1.

The distance focus chart illustrates the focal points of the distance object OP1, OP2 and OP3 as DF1, DF2 and DF3 at the image plane and the out-of-focus rays of OP1, OP2 and OP3 passing through the near addition zone make up the remaining light rays falling at the image plane (below the in focus distance object points). The near focus chart illustrates the focal points of a near object OP1, OP2 and OP3 as NF1, NF2 and NF3 at the image plane and the out-of-focus rays of OP1, OP2 and OP3 passing through the distance vision zone make up the remaining light rays falling above the near focal points at the image plane. FIG. 30 illustrates the greater separation between the in focus and out-of-focus light at the image planel plane as well as the absence of interactions between the out-of-focus light rays of object points OP1, OP2 and OP3 and the images of OP1, OP2 and OP3 produced by the distance or near powered zone(s) in these laterally separated ring spectacle lens designs.

FIGS. 31A and 31B are schematic drawings showing spot diagrams and RMS values of the focal point, DF1 and NF1, of object point OP1 formed at the retinal plane by the ophthalmic lens of FIG. 29B in accordance with certain embodiments.

FIG. 31A illustrates a spot diagram and RMS values of the focal point DF1 of the distance object point OP1 formed at the retinal plane by the spectacle lens of FIG. 29B having laterally separated optics for distance and near optical zones sampled over a 5 mm aperture at the spectacle lens plane. In this example, DF1 has an RMS size of 0.72 um. These values are similar to that of focal points produced by a single vision optical design of similar aperture size. However, unlike the cases of lenses configured with coaxial optics such as in FIG. 10A, there may not be an interaction from the defocused light rays of object points OP2 and OP3 formed by the near zone (RMS values=0). The focal point DF1 does not have defocused light rays from adjacent object points overlaying and increasing the RMS spot size and so the overall average RMS values remain small at 0.72 um for the lens configured with laterally separated foci. Likewise, DF2 and DF3 may also similarly not be impacted by defocused light from adjacent object points.

FIG. 31B illustrates a spot diagram and RMS values of the near focal point NF1 of the near object point OP1 formed at the retinal plane by the spectacle lens of FIG. 29B. In this example, NF1 has an RMS size of 0.8 um. These values are similar to that expected of focal points produced by a single vision optical design because of the lack of interaction from the defocused light rays of near object points OP2 and OP3 formed by the distance zone (RMS values=0). The focal point NF1 does not have defocused light rays from adjacent object points overlaying and increasing the RMS spot size and so the overall average RMS values remain small at 0.8 um for the lens configured with a laterally separated near focal point. Likewise, NF2 and N-F3 may also similarly not be impacted by defocused light from adjacent object points.

Therefore, the spectacle lens of FIG. 29B configured with laterally separated optics described herein may show improved sharpness and higher distance and near image quality than the coaxial based designs of e.g., FIG. 10A. In addition the increased lateral separation of the focal points may widen the near zone and the field of view through the near zone compared to the lens described in e.g., FIG. 26 configured with a smaller separation of the focal points.

Figures 32, 33:
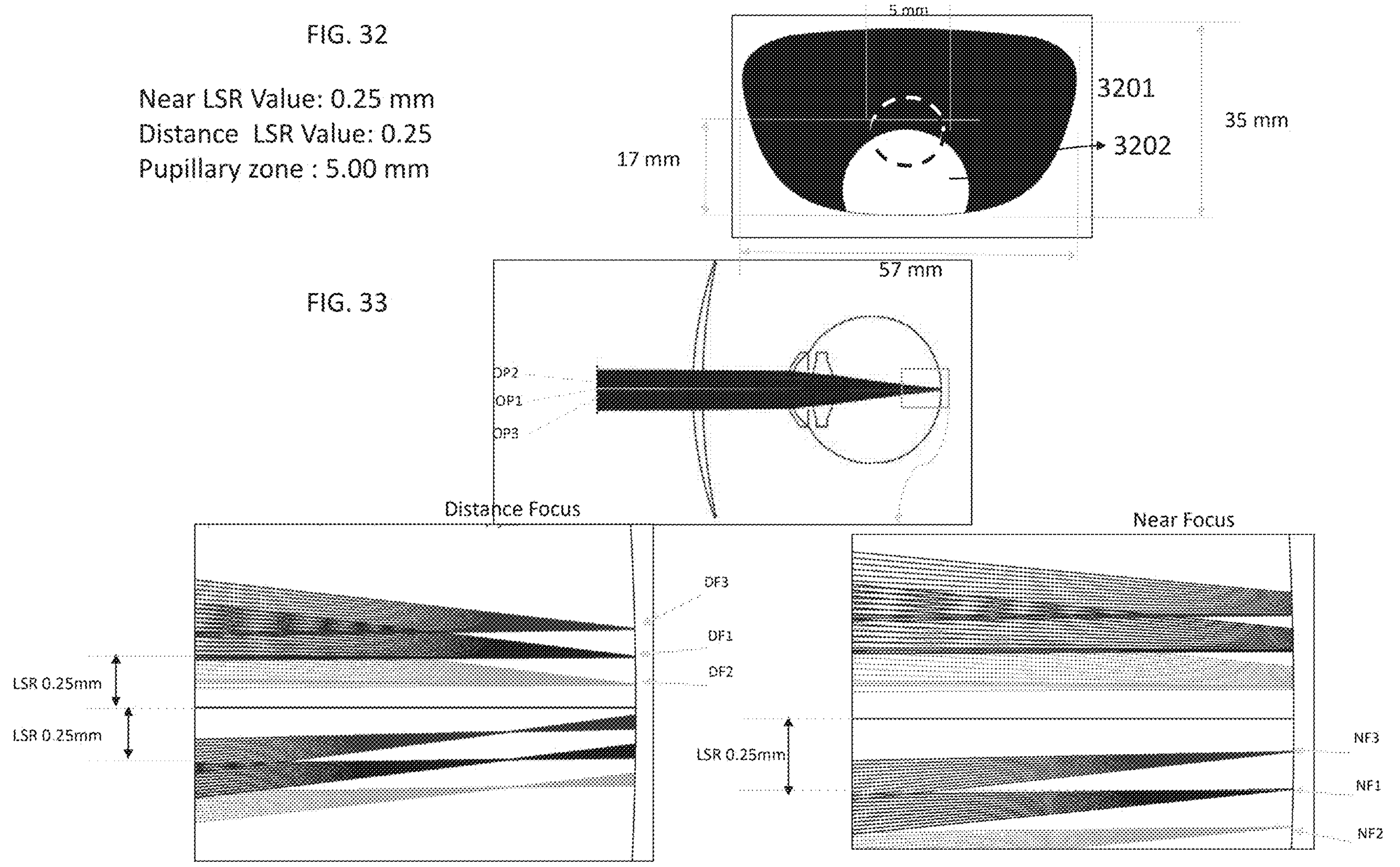
FIG. 32 is a schematic drawing showing a plan view of an ophthalmic lens (e.g., bifocal spectacle lens) comprising laterally separated optics for distance and near optical zones in accordance with certain embodiments.
FIG. 33 is a schematic drawing showing ray tracing of a distance object and a near object imaged through the ophthalmic lenses of FIG. 32 in accordance with certain embodiments.

FIG. 32 is a schematic drawing showing a plan view of an ophthalmic lens (e.g., bifocal spectacle lens) comprising laterally separated optics for distance 3201 and near 3202 optical zones in accordance with certain embodiments. In this example, both the distance and near powered zones have been configured with a single focal point with their optical axes configured to be laterally separated by 0.5 mm. The near addition has a power of +2.5 D. However, unlike the lens of FIG. 29B where only the near focal point was laterally separated or displaced downward the lens in FIG. 32 has been configured so that the distance focal point is displaced superiorly by 0.25 mm while the near focal point has been displaced downward by an equal and opposite amount of 0.25 mm for a total net lateral separation between the focal points of 0.5 mm. The plan view shows the optical zone split into two regions, a superior zone and an inferior zone. Like the spectacle lens described in FIG. 29B, this spectacle lens example is configured so that the junction between the distance and near zones is substantially seamless and/or substantially junction less. The improved junction may be achieved by the use of spherical front surface curvatures.

FIG. 33 is a schematic drawing showing ray tracing of a distance object and a near object imaged through the ophthalmic lenses of FIG. 32 in accordance with certain embodiments. FIG. 33 also provides higher magnification insets of the ray tracing formed when the distance object is in focus at the retinal plane (distance focus) and when the near object is in focus at the retinal plane (near focus). In the respective figures light rays passing through the respective out-of-focus zones are represented as an out-of-focus blur circle at the image plane. The distance object in the distance focus chart is further defined by three points; a central object point 1 (OP1) on axis and points 2 and 3 (OP2 and OP3) positioned 0.5 degrees apart on either side of OP1. Likewise, the near object in the near focus inset has been further defined by three points; a central object point 1 (OP1) on axis and points 2 and 3 (OP2 and OP3) positioned 0.15 degrees apart on either side of OP1.

The distance focus chart illustrates the focal points of the distance object OP1, OP2 and OP3 as DF1, DF2 and DF3 at the image plane and the out-of-focus rays of OP1, OP2 and OP3 passing through the near addition zone make up the remaining light rays falling at the image plane (below the in focus distance object points). The near focus chart illustrates the focal points of a near object OP1, OP2 and OP3 as NF1, NF2 and NF3 at the image plane and the out-of-focus rays of OP1, OP2 and OP3 passing through the distance vision zone make up the remaining light rays falling above the near focal points at the image plane. FIG. 33 illustrates the separation between the in focus and out focus light at the image planel plane on either side of a geometrical center of the 5 mm aperture of the spectacle lens plane as well as the absence of interactions between the out-of-focus light rays of object points OP1, OP2 and OP3 and the images of OP1, OP2 and OP3 produced by the distance or near powered zone(s) in these laterally separated ring spectacle lens designs.

FIGS. 34A and 34B are schematic drawings showing spot diagrams and RMS values of the focal point, DF1 and NF1, of object point OP1 formed at the retinal plane by the ophthalmic lens of FIG. 32.

FIG. 34A illustrates a spot diagram and RMS values of the focal point DF1 of the distance object point OP1 formed at the retinal plane by the spectacle lens of FIG. 32 having laterally separated optics for distance and near optical zones sampled over a 5 mm aperture at the spectacle lens plane. In this example, DF1 has an RMS size of 0.8 um. These values are similar to that of focal points produced by a single vision optical design of similar aperture size. However, unlike the cases of lenses configured with coaxial optics such as in FIG. 10A, there is may not be an interaction from the defocused light rays of object points OP2 and OP3 formed by the near zone (RMS values=0). The focal point DF1 does not have defocused light rays from adjacent object points overlaying and increasing the RMS spot size and so the overall average RMS values remain small at 0.84 um for a lens configured with laterally separated foci. Likewise, DF2 and DF3 may also similarly not be impacted by defocused light from adjacent object points.

FIG. 34B illustrates a spot diagram and RMS values of the near focal point NF1 of the near object point OP1 formed at the retinal plane by the spectacle lens of FIG. 32. In this example, NF1 has an RMS size of 1.49 um. These values are similar to that expected of focal points produced by a single vision optical design because of the lack of interaction from the defocused light rays of near object points OP2 and OP3 formed by the distance zone (RMS values=0). The focal point NF1 does not have defocused light rays from adjacent object points overlaying and increasing the RMS spot size and so the overall average RMS values remain small at 1.49 um for a lens configured with a laterally separated near focal point. Likewise, NF2 and NF3 may also similarly not be impacted by defocused light from adjacent object points.

Therefore, the spectacle lens of FIG. 32 configured with laterally separated optics described herein show improved sharpness and higher distance and near image quality than the coaxial based designs of e.g., FIG. 10A. In addition, the lateral separation of both distance and near focal points superiorly and inferiorly, respectively, has not impacted the desirable image quality of the focal points DF-1 and NF-1.

Figures 35, 36:
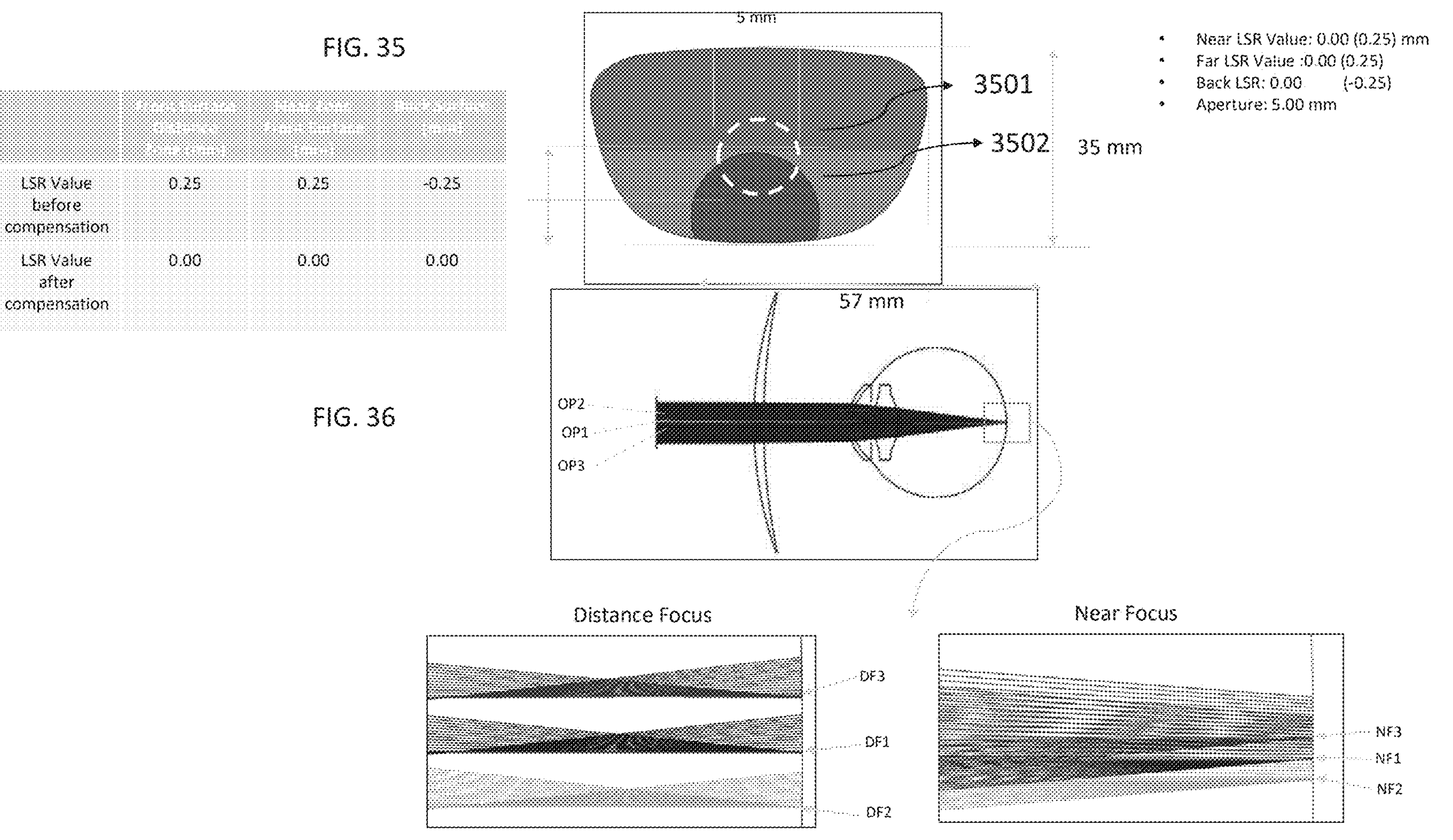
FIG. 35 is a schematic drawing showing a plan view of an ophthalmic lens (e.g., a progressive spectacle lens) comprising laterally separated optics for distance and near optical zones in accordance with certain embodiments.
FIG. 36 is a schematic drawing showing ray tracing of a distance object and a near object imaged through the ophthalmic lenses of FIG. 35 in accordance with certain embodiments.

FIG. 35 is a schematic drawing showing a plan view of an ophthalmic lens (e.g., a bifocal spectacle lens) comprising laterally separated optics for distance 3501 and near 3502 optical zones in accordance with certain embodiments. In this example, both the distance and near powered zones have been configured with a single focal point with their optical axes and focal points configured to be laterally separated by 0.5 mm. The near addition has a power of +2.5 D. Like the lens of FIG. 35, the lens in FIG. 35 has been configured so that the distance focal point is displaced superiorly by 0.25 mm while the near focal point has been displaced downward by an equal and opposite amount of 0.25 mm for a total net lateral separation between the focal points of 0.5 mm. The plan view shows the optical zone split into two regions a superior zone and an inferior zone. The superior zone in this example contains the distance power, while the inferior zone contains both a near power area and distance power areas in the periphery. Like the spectacle lens described in FIG. 32, this spectacle lens example is configured so that the junction between the distance and near zones is substantially seamless and/or substantially junction less. The substantially seamless and/or substantially junction less intersection between the zones may be achieved by the use of spherical front surface curvatures. When laterally separating optical axes and focal points an amount of prismatic power may be introduced to the spectacle lens. The lens of FIG. 35 has been designed with a spherical back surface curvature that creates an equal and opposite amount of lateral separation (−0.25 mm) from that provided to the front surface distance and near zones. The net result of that back surface design is that prismatic power introduced by the front surface design is eliminated whilst the advantage of the lateral separation of the distance and near optical zones in producing a substantially seamless and/or substantially junction less intersection remains.

FIG. 36 is a schematic drawing showing ray tracing of a distance object and a near object imaged through the ophthalmic lenses of FIG. 35. FIG. 36 also provides higher magnification insets of the ray tracing formed when the distance object is in focus at the retinal plane (distance focus) and when the near object is in focus at the retinal plane (near focus). In the respective figures light rays passing through the respective out-of-focus zones are represented as an out-of-focus blur circle at the image plane. The distance object in the distance focus chart is further defined by three points; a central object point 1 (OP1) on axis and points 2 and 3 (OP2 and OP3) positioned 0.5 degrees apart on either side of OP1. Likewise the near object in the near focus inset has been further defined by three points; a central object point 1 (OP1) on axis and points 2 and 3 (OP2 and OP3) positioned 0.15 degrees apart on either side of OP1.

The distance focus chart illustrates the focal points of the distance object OP1, OP2 and OP3 as DF1, DF2 and DF3 at the image plane and the out-of-focus rays of OP1, OP2 and OP3 passing through the near addition zone make up the remaining light rays falling at the image plane (above the in focus distance object points). The near focus chart illustrates the focal points of a near object OP1, OP2 and OP3 as NF1, NF2 and NF3 at the image plane and the out-of-focus rays of OP1, OP2 and OP3 passing through the distance vision zone make up the remaining light rays falling at the image plane. FIG. 36 illustrates the separation between the in focus and out focus light at the image plane on either side of a geometrical center of the 5 mm aperture of the spectacle lens plane as well as the extent of interactions between the out-of-focus light rays of object points OP1, OP2 and OP3 and the images of OP1, OP2 and OP3 produced by the distance or near powered zone(s) in these laterally separated spectacle lens designs incorporating laterally separated optical axes and focal points.

FIGS. 37A and 37B are schematic drawings showing spot diagrams and RMS values of the focal point, DF1 and NF1, of the respective object point OP1 formed at the retinal plane by the ophthalmic lens of FIG. 35 in accordance with certain embodiments. In this example, DF1 has an RMS size of 5.79 um. The small amount of lateral separation of the focal points (0.25 mm) was not sufficient to eliminate an overlap of out of focus light from OP1 passing through the near zone on DF1. However, unlike the cases of ophthalmic lenses configured with coaxial optics such as in FIG. 10A, even with a relatively small amount of lateral separation such as used in the example (0.25 mm) there is still no interaction from the defocused light rays of distance object points OP2 and OP3 formed by the near zone (RMS values=0). The focal point DF1 only has a reduced amount of defocused light rays from object points overlaying and increasing the RMS spot size and so the overall average RMS values remain smaller at 5.79 um for a lens configured with laterally separated foci. Likewise, DF2 and DF3 would also be similarly impacted by defocused light from adjacent object points.

FIG. 37B illustrates a spot diagram and RMS values of the near focal point NF1 of the near object point OP1 formed at the image plane by the spectacle lens of FIG. 36. In this example, NF1 has an RMS size of 1.84 um. These values are similar to that expected of focal points produced by a single vision optical design because of the lack of interaction from the defocused light rays of near object points OP2 and OP3 formed by the distance zone (RMS values=0). However, because the back surface was designed to optically eliminate the lateral separation of the focal points to nullify induced prismatic power of the overall lens the focal point NF1 does have defocused light rays from the adjacent object point OP2 overlaying and increasing the RMS spot size to 41.29 um and so the overall average RMS value increased to 23.86 um for a lens configured without prismatic power. Likewise, NF2 and NF3 may also be similarly impacted by defocused light from adjacent object points without residual lateral separation of focal points.

Therefore, the spectacle lens of FIG. 36 configured with laterally separated optics on the front and back surfaces show a substantially seamless and/or substantially junction less surface without prismatic power but with slight compromises to image quality. Image quality may be improved to single vision quality with slight increases in lateral separation and the introduction of a small amount of prism power.

FIG. 38 is a schematic diagram of a progressive addition (PAL) spectacle lens, according certain embodiments. The PAL lens may be designed with a distance area 3801 that may be larger than the distance area available with conventional PAL type lenses and an inferiorly located near power area 3802 surrounded by one or more progressively powered areas. The progressive power zone in this example progresses in three steps from the distance refraction power to the full near refraction power of +2.5 D. In some embodiments, an increase in distribution of the power progression may be incorporated into such a lens design based on the patient's refractive and visual requirements and the desired length of the power progression. In this example, the length of the power progression is about 17 mm. The three power areas and their focal points in the progressive power area of this example are laterally separated from the distance focal point. The first, second and third power areas of the progressive power area are laterally separated from the distance power focal point by 1.5 mm. In this example, the front surface curvature of the distance area and the progressive power areas are spherical and the junction between the areas is substantially seamless and/or substantially junction less (e.g., little to no blending is necessary). The diameter of the first area in the progressive power zone is larger than the second progressive power zone and both the first and second areas are larger in diameter than the third progressive area. The location of the improved junctions of this example are illustrated in FIG. 38 as lines B, C, D and E but are substantially invisible to an observer and no actual line or mark are present on the ophthalmic lens. FIG. 38 includes a schematic diagram of the profile of the PAL spectacle lens. The smooth progressive power profile and the spherical surface curvatures and the substantially seamless and/or substantially junction less intersections of the surface curvatures are represented along with the imaginary location of junction lines B, C, D and E.

The PAL lens shown in FIG. 38 has been designed with 1.5 mm of lateral separation between the optical axis of the distance area, on which the distance focal point is formed, and the first optical axis, and the first focal point, of the three power areas of the progressive power area. Therefore, an amount of prismatic power would be introduced by the difference in surface curvatures of the areas on front surface of the PAL spectacle lens. However, similarly to the lens of FIG. 35, the PAL spectacle lens of FIG. 38 has been designed with a back surface that creates an equal (or substantially equal) and opposite (or substantially opposite) amount of lateral separation (e.g., −1.5 mm) from that provided to the front surface progressive power zones in the inferior region of the lens. The net result of incorporating this opposite amount of lateral separation in the back surface curvature may be that prismatic power introduced in the inferior area of the front surface may be eliminated whilst the advantage of the lateral separation of the distance and near optical zones in producing a substantially seamless and/or substantially junction less intersection remains.

Figure 39:
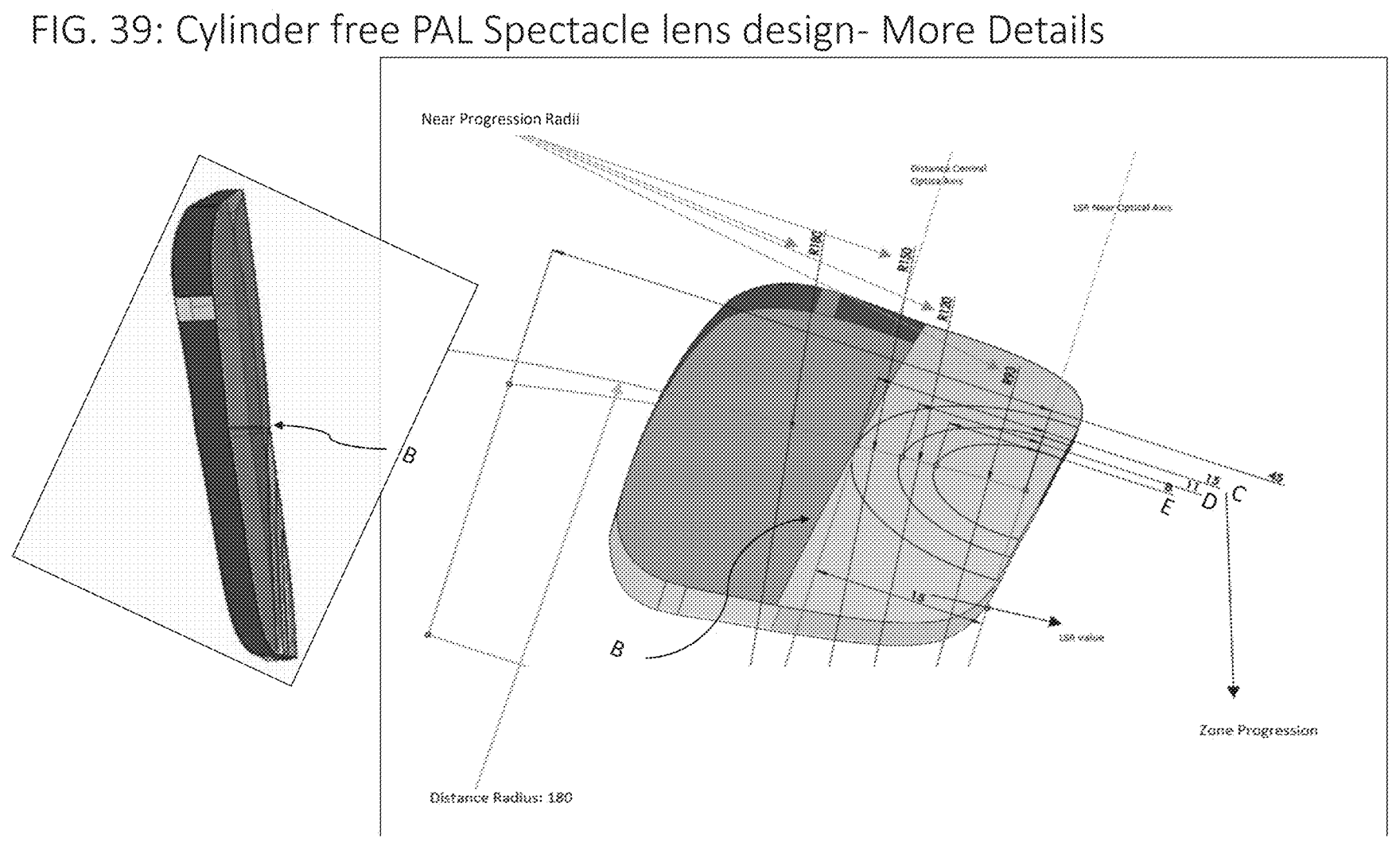

FIG. 39 is a geometric diagram showing more details of the front surface used to form the example progressive addition spectacle lens (PAL) shown in FIG. 38. The figure shows an optical center of the lens, A, the location of the imaginary join of the superior and inferior zones of the lens, B, and the three progressive power areas C, D and E. The superior area of the lens in this example contains only distance power. The inferior area may be the area where a portion of the area contains the progressive power area and the near power area and the remainder being the distance power area. The superior distance powered area may be described by a spherical curvature and the inferior area, may be described by a series of spherical curvatures to create the three powers in the progressive power area and the remainder is the same curvature that describes the distance power. Values are in millimeters with the distance radius being 180 and the near radii being R93, R120, and R150. The lateral separation of the progressive powered zones may be shown as a difference in distance between the A the optical center of the lens and the progressive powered zones.

FIG. 40 details the power maps of the PAL spectacle lens design shown in FIG. 39. Two power maps are represented covering an area of the spectacle lens. An average sphere power map 35 mm×35 mm and a cylinder power map 35 mm×60 mm of the PAL spectacle lens designed with lateral separation of the distance and progressive power areas are represented. The sphere power map shows large and wide areas of uniform power in the distance powered, progressive powered and near powered areas in this example. The sphere and cylinder power maps shown in FIG. 40 are substantially more uniform and substantially wider average spherical power zones (than those of other PAL designs) that are substantially free of a blending area and of total and surface cylinder power but still delivering a substantially seamless and substantially junction less surface. Therefore, the ophthalmic lens design and construction has maintained a substantially similar tangential and sagittal surface curvatures and powers through the progressive corridor. The prior art PAL designs are compromised by a significant blending area containing significant cylinder power of more than 0.5 DC, more than 1.0 DC and even more than 2.0 DC in order to provide a corridor of progressive power in a substantially junction less surface.

The exemplary embodiment PAL spectacle lens depicted in FIG. 39 is symmetrical about a vertical meridian. Additional embodiments of PAL spectacle lens may be designed for custom or individualized parameters desired by the wearer or practitioner (e.g.,dimensions or locations of the distance and progressive areas as so desired). The PAL lens may be asymmetric for example and may be designed for a right or left eye and the change in convergence of the eyes and the associated changes in distance between the two eyes when looking from distance vision to near vision or the preference of a user to prefer the objects being gazed to be offset to one side while using a portion of the progressive power area. The PAL spectacle lens may be designed with an amount of lateral separation and that lateral separation may be distributed between areas of the lens to a desired degree between the upper and lower portion of the lens and the distance area and the progressive area and within the progressive areas. The lateral separation may be distributed between the front and back surfaces to a desired appropriate degree to meet the ophthalmic needs of the wearer, the practitioner, the manufacturer and/or the manufacturing process. The design may be wholly or partially contained on the front surface of the ophthalmic lens or the back surface of the ophthalmic lens. The lateral separation of the optical axes may be wholly or partially contained in a semi-finished lens blank and the final desired lens design may be finished in a final manufacturing process at the same location or at a different location and different time once the complete prescription of the patient is determined and ordered. The new design may be applied to an suitable manufacturing process like other ophthalmic lens, spectacle lens, contact lens or intraocular lens. In the case of a spectacle lens and for example a PAL, the lens may be fully molded, partially produced on a semi-finished blank containing a front or back surface portion of the PAL surface or a single vision blank and the PAL may be surfaced on the back surface of the blank by a surface cutting and polishing process. The ophthalmic lens may be constructed and applied to increase the efficiency of the manufacturing process and supply chain by using a reduced number of semi-finished blanks or base curve blanks in stock or reduces the need for a unique right and left asymmetric design because of the wider fields of view of the vision correction areas.

The final spherical and cylindrical dioptric powers and axes of the astigmatism powers desired for the patient's refractive error may be completed in a finishing step from a stock of semi-finished or unfinished lens blanks at the laboratory or office. The final lateral separation of the optical axes may also be completed to the desired level during a final finishing step along with the progressive power profile and fitting heights and interpupillary distances required for the most desirable function of the presbyope or myope. For example, a residual prismatic power that may be present on a semi-finished or finished lens blank may be eliminated by the final processing production of the spectacle lens. For example the prismatic power may be desired to be less than 0.12 D or 0.25 D or less than 0.5 D or less than 1.5 D or less than 3 D prism diopters or more.

Extended Depth of Focus (EDOF)

In some embodiments, the ophthalmic lenses described herein may provide extended depth of focus (EDOF). In some embodiments, the light rays passing through the ophthalmic lens and converging to form one or more off-axis focal points continue further beyond the one or off-axis focal points and may in conjunction with on-axis light rays provide EDOF. In some embodiments, the light rays passing through the ophthalmic lens and converging to form one or more off-axis focal points continue further beyond the one or off-axis focal points and may in conjunction with on-axis light rays provide EDOF with good image quality. In some embodiments, a desirable amount of EDOF may be achieved by having a desirable amount of lateral separation of focal points between the one or more on-axis and one or more off-axis focal points, wherein the lateral separation of focal points between the on-axis and off-axis focal points results from incorporation of optically normal to surface configuration in the ophthalmic lens. In some embodiments, a desirable amount of EDOF may be achieved with an ophthalmic lens incorporating a first and a second optical zone wherein the power profile of the second optical zone incorporates a relatively more negative power (m component) and a relatively more positive power (p component) than the first zone power and where m=p<+/−20%. In some embodiments, the EDOF is located substantially anterior to the retinal image plane.

Figure 41:
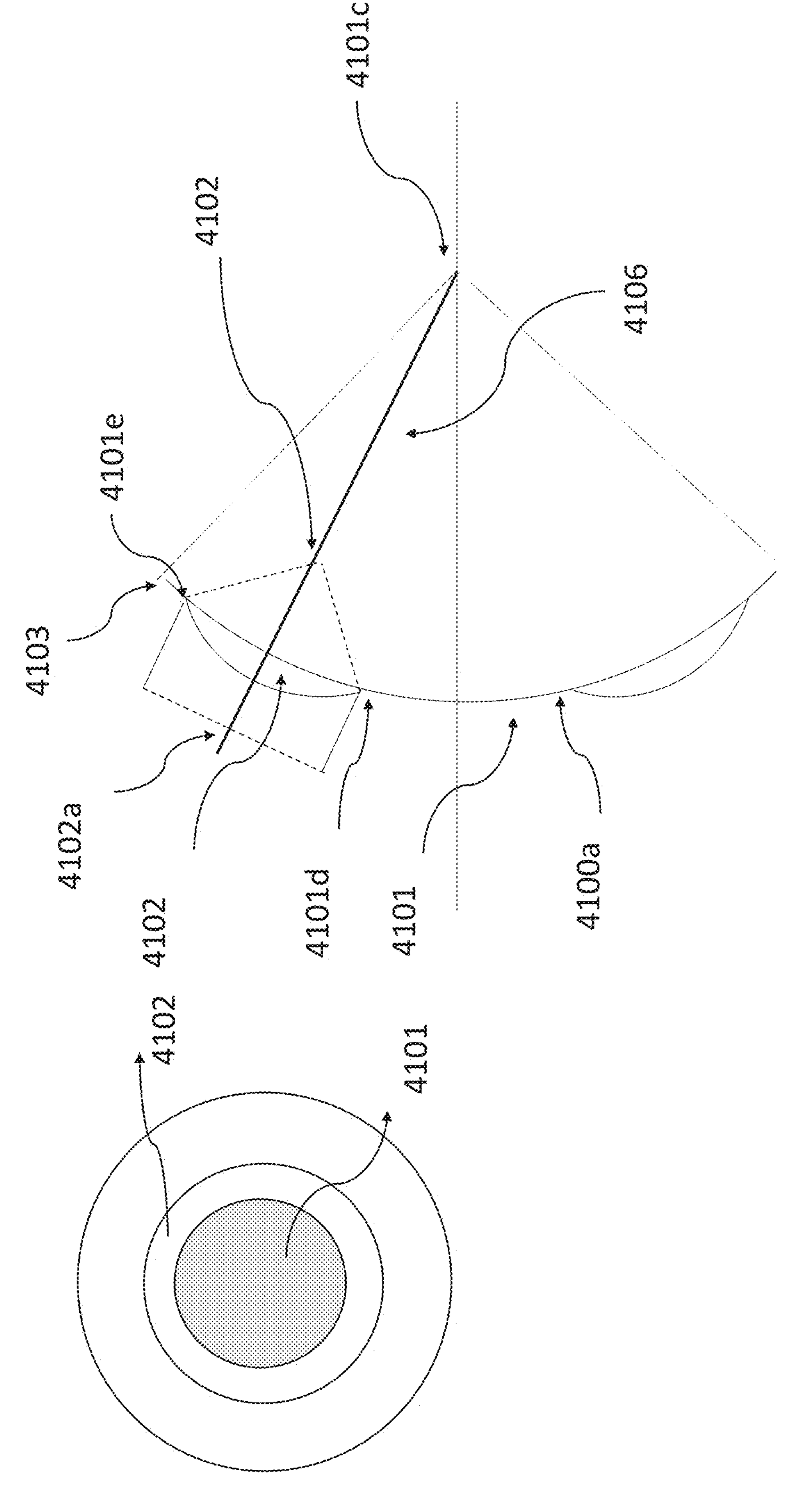
FIG. 41 is a schematic diagram of an ophthalmic lens showing an exemplary embodiment of a geometrically normal to surface optical zone in accordance with certain embodiments.

FIG. 41 is a schematic diagram showing an ophthalmic lens 4100 comprising a first optical zone 4101 with a first power, at least one second zone 4102 concentric with the first optical zone and structured with a curvature that is referred to as geometrically normal to the base surface (i.e. curvature) configuration. A normal to the base (base herein refers to the first optical zone) surface geometry feature may be used to configure or achieve a desirable amount of lateral separation of off-axis focal points formed by second optical zone 4102 from the on-axis focal points formed by the first optical zone 1401. As illustrated in FIG. 41, a geometrically normal to surface curvature is where the center of the second optical zone 4102, the center of the curvature/arc of 4102, and the center of curvature of the first optical zone the ophthalmic lens 4100 may be located along a single line. In some embodiments, there may be a certain amount of lateral separation of the optical axes of the first and second optical zone of a lens designed with a geometrically normal to surface features. Configuring the second optical zone 4102 as geometrically normal to the surface may result in the second optical zone being discontinuous (not a smooth transition) with the surrounding zones e.g. the first optical zone and a third annular optical zone 4103.

Figure 42:
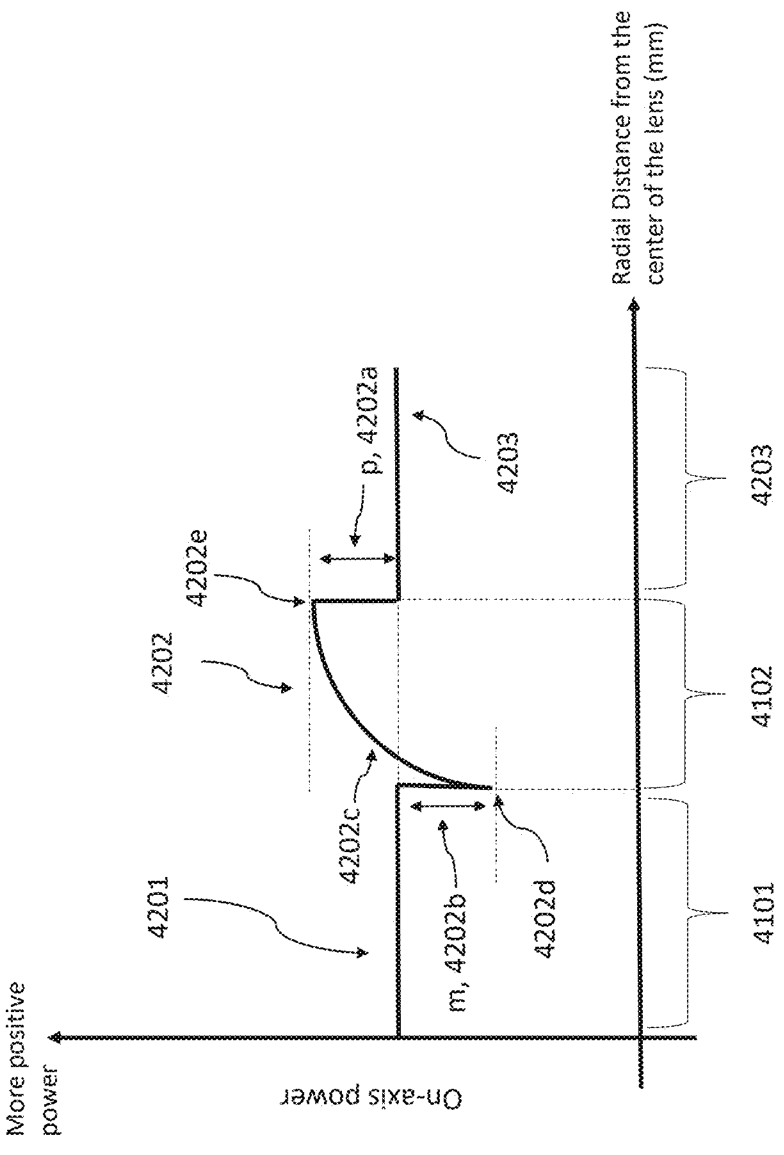
FIG. 42 is a schematic diagram showing an exemplary embodiment of a normal to surface curvature of an optical zone of an ophthalmic lens in accordance with certain embodiments.

FIG. 42 is a schematic of the on-axis power profile of the optical zone of an ophthalmic lens configured with a first central optical zone 4201 and an annular second optical zone 4202 configured as geometrically normal to the base (i.e. central optical zone). As illustrated, the first optical zone 4101 may have a first power 4201 that is more positively powered than the distance refractive error of the eye and thus light traveling through the first optical zone may result in one or more focal points at a plane other than the retina of the eye and a third optical zone 4203 powered to provide an on axis focal point coincident with the center zone focal point. The second annular optical zone 4102 may incorporate a power profile 4202 with a more positive ("p", 4202*a*) and/or more negative ("m", 4202*b*) component relative to first power 4201 and a progressive power profile component 4202*c* that increases in positive power from 4202*d* to 4202*e*. The difference between the absolute power between 4202*d* and 4202*e* is a measure of the on axis depth of focus in diopters. The "m" component arises from the geometrically normal to the surface discontinuity between the first optical zone and the innermost portion of the second optical zone; the "p" component arises from the geometrically normal to the surface discontinuity between the outermost portion of second optical zone and innermost portion of a third optical zone providing a coaxial focal point coincident with the center zone. The progressive power profile 4202*c* in the second annular optical zone joining 4202*d* and 4202*e* may be a sloped (e.g., curved, curvilinear or linear or other) power profile depending on the surface configuration of the second optical zone and the amount of lateral separation of the optical axes of the first and second optical zones. In the embodiment of FIG. 41 the ophthalmic lens is configured with geometrically normal to surface features creating a lateral separation between the on-axis and off-axis focal points resulting in an on-axis power profile where m=p is <about ±20%. An ophthalmic lens is deemed as fulfilling an 'optically normal to the surface condition' when m=p<about ±20%. In some embodiments, an ophthalmic lens configured with a optically normal to the surface configuration provides a better image quality because a geometrically normal to the base surface configuration may not result in the lens fulfilling the condition such as for example, m=p<about ±20%. As the difference between m and p becomes larger, image quality along the depth of focus is compromised by an increased interference between light rays from on axis and off axis light rays. In some embodiments, the location and diameter of the first optical zone may impact the m:p ratio. For example, a smaller central optical zone (e.g., <about 2 mm) may result in m:p ratio >20% since the light rays passing through the innermost portion of the second optical zone tend to be flatter (more parallel and results in 'm' having a greater relative minus power compared to 'p' component), thus the angle between these rays and the optical axis decreases resulting in the intersection of the rays with the optical axis may result in the "m" component having a greater relative minus power then the 'p' component and interference between the on axis and off axis light rays at image planes along the depth of focus increases. Furthermore, a geometrical normal to the surface configuration over wider, e.g. >1.5 to 2.0 mm or more, second optical zone may not maintain a geometrical normal to the surface configuration. As the zone widens, the outermost portion of the second optical zone may increase the p component and consequently, the interference between on axis and off axis light rays at image planes along the depth of focus increases.

Therefore, in exemplary embodiments described herein, to achieve a depth of focus that does not substantially comprise image quality, a desirable amount of lateral separation between focal points from the one or more first optical zone and the one or more second optical zones is obtained by incorporation of one or more optically normal to surface features that results from consideration and incorporation of one or more features of, a) substantially similar discontinuity at both the edges of the second optical zone, b) the components of m and p of the one or more second optical zone, wherein m:p component is <about ±20%, between 1 to 20%, 1 to 5%, 5 to 10%, 10-15% or about 10 to 20%, and c) location and width of the one or more second optical zones on the ophthalmic lens and d) width of the central optical zone on the ophthalmic lens.

In some embodiments, the ophthalmic lens configured with optically normal to surface features may comprise at least one first optical zone with a first axis, the at least one first optical zone being configured such that, in use with an eye, at least a portion of light passing through the at least one first optical zone is refracted to one or more focal points on the first axis; and at least one second optical zone configured such that, in use with the eye, at least a portion of light passing through the at least one second optical zone is refracted to one or more focal points. The one or more focal points from the at least one second optical zones may not be on the first axis and the second zone may be configured such that light that converges to form the one or more focal points continue or extend beyond the one or more focal points and in conjunction with the light rays from the first optical zone provide an extended depth of focus.

In some embodiments, the at least one first optical zone of the ophthalmic lens with optically normal to surface features may comprise a first portion that has a substantially circular shape located centrally on the ophthalmic lens and a second optical zone that has a substantially annular shape and located between the first portion of the first optical zone and the second portion of the first optical zone. The at least one first optical zone and the at least one second optical zone may be concentric (e.g., substantially concentric, and/or partially concentric). In some embodiments, the ophthalmic lens may comprise alternating zones of first optical zones and second optical zones. In some embodiments, the second optical zone may comprise one or more zones that are conjoint and may vary in power.

In some embodiments, the at least one second optical zone of the ophthalmic lens with optically normal to surface features may be configured such that, in use with the eye, the light passing through the at least one second optical zone is refracted to multiple (e.g., 1, 2, 3, 4, 5, 6, 7, 8, 9, 10, 11, 12, 13, 14, 15, or 16) focal points, not on the first axis. In some embodiments, the multiple focal points resulting from light passing through the at least one second optical zone may form a continuous ring of focus (e.g., have a significant and/or infinite number of focal points) surrounding and separated from the first axis. In certain embodiments, the multiple focal points resulting from light passing through the at least one second optical zone may form an incomplete ring of focus.

In some embodiments, one or more characteristics of the one or more second optical zone of the ophthalmic lens with optically normal to surface features may be configured such that the light passing through the one or more second optical zone and converging to form the one or more focal points continues or extends beyond the one or more focal points and may in conjunction with the light passing through the first optical zone provides an extended depth of focus. In some embodiments, one or more characteristics of the second optical zone such as the width, circumferential extent (e.g. arc or annulus), curvature, number of zones, focal power and focal length of the one or more focal points associated with one or more sections of the zone, location on the ophthalmic lens, base power of the ophthalmic lens and the extent and/or means of lateral separation between the first and second optical zone may influence the extended depth of focus provided by the ophthalmic lens.

In some embodiments, the one or more second optical zones may be between about 0.05 mm to 3 mm. For example, in some embodiments, the optical zone width may be about 0.05 mm, 0.1 mm, 0.15 mm, 0.2 mm, 0.3 mm, 0.4 mm, 0.5 mm, 0.6 mm, 0.7 mm, 0.75 mm, 0.8 mm, 0.9 mm, 1 mm, 1.25 mm, 1.5 mm, 1.75 mm, 2 mm, 2.25 mm, 2.5 mm, 2.75 mm, or 3 mm. In some embodiments, the ring width may be between about 0.05 to 2.0 mm, about 0.1 mm to 2.0 mm, about 0.2-0.5 mm, 0.5-0.75 mm, 0.75-1 mm, 1-1.5 mm, 1.25-1.75 mm, 1.5-2 mm, 1.75-2.25 mm, 2-2.5 mm, 2.25-2.75 mm, and/or 2.5-3 mm.

In some embodiments, the absolute power of curvature of the one or more second optical zones may be between about −10 to +10 D. For example, in some embodiments, the ring curvature may be about −10 D, −9 D, −8 D, −7 D, −6 D, −5 D, −4 D, −3 D, −2 D, −1 D, +1 D, +2 D, +3 D, +4 D, +5 D, +6 D, +7 D, +8 D, +9 D, and/or +10 D. As described herein the term "curvature" may refer to a geometrical curvature (or line) or the curvature (or line) that mathematically best fits an area or cross-section of the surface (power profile) of the lens.

In some embodiments, the lateral separation of the focal points from the first optical zone and the second optical zone may be between 0.2 to 2 mm. For example the lateral separation of the focal points from the one or more first optical zone and the one or more second optical zone at the image plane may be about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm, about 1 mm, about 1.1 mm, about 1.2 mm, about 1.25 mm, about 1.3 mm, about 1.35 mm, about 1.4 mm, about 1.45 mm, about 1.5 mm, about 1.55 mm, about 1.6 mm, about 1.65 mm, about 1.7 mm, about 1.75 mm, about 1.8 mm, about 1.85 mm, about 1.9 mm or about 2 mm). In some embodiments, the lateral separation of the focal points from the first optical zone and the second optical zone at the image plane may be less than about 50 um, 60 um, 70 um, 80 um, 90 um, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.7 mm, 0.75 mm, 0.8 mm, 0.85 mm, 0.9 mm, 0.95 mm, and/or 1 mm). In some embodiments, the lateral separation of the focal points from the one or more first optical zone and the one or more second optical zone at the image plane may be more than about 50 um, 60 um, 70 um, 80 um, 90 um, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.7 mm, 0.75 mm, 0.8 mm, 0.85 mm, 0.9 mm, 0.95 mm, and/or 1 mm).

Figures 43A, 43B:
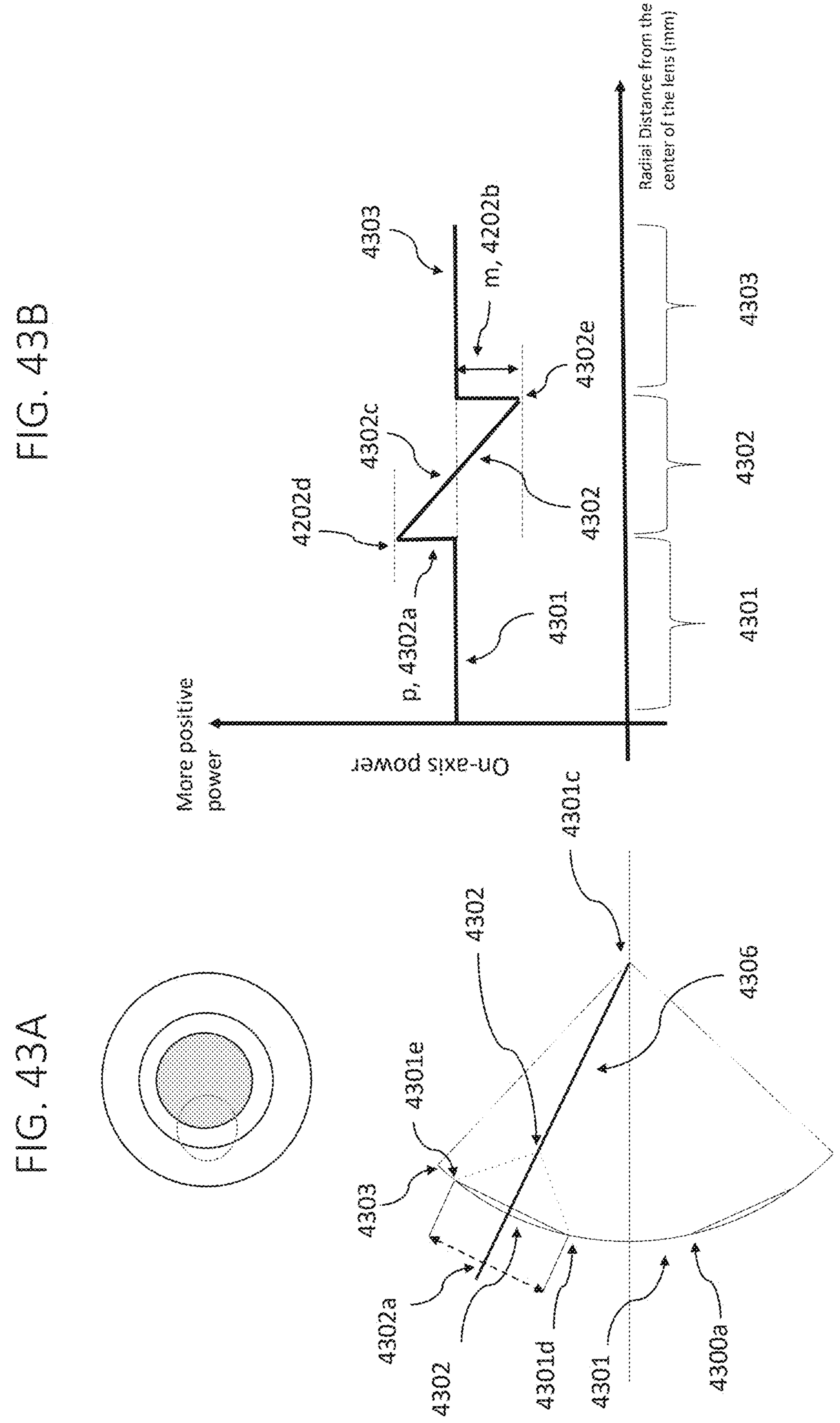
FIGS. 43A and 43B are schematic diagrams illustrating an exemplary embodiment of an ophthalmic lens with a geometrically normal to surface line curvature of an optical zone in accordance with certain embodiments

FIG. 43 is a schematic diagram showing exemplary embodiment of the an ophthalmic lens incorporating a central optical zone 4301 surrounded by an annular zone 4302, wherein light rays passing through the annular zone 4302 result in one or more off-axis focal points that interact with the on-axis rays from the central optical zone 4301. However, instead of the second optical zone configured with a curved surface as in the embodiment of FIG. 41, in the embodiment of FIG. 43, a line is used to form the annular zone on the back surface of the ophthalmic lens (FIG. 43A). As illustrated, the central zone power 4301 is more positively powered than the refractive error of the eye and thus light traveling through the first optical zone may result in one or more focal points at a plane other than the retina of the eye and a third optical zone 4303 powered to provide an on axis focal point coincident with the central zone focal point. The second annular optical zone 4302 (FIG. 43B) may incorporate a power profile 4202 with a more positive ("p", 4302*a*) or more negative ("m", 4302*b*) components relative to first power 4301 and a progressive power profile component 4302*c* that decreases in positive power from 4302*d* to 4302*e*. The "m" arises from the geometrically normal to the surface discontinuity between the first optical zone and the innermost portion of the second optical zone; the "p" component arises from the geometrically normal to the surface discontinuity between the outermost portion of second optical zone and innermost portion of a third optical zone providing a coaxial focal point coincident with the center zone. The progressive power profile in the second annular optical zone 4302*c* joining 4302*d* and 4302*e* is a linear power profile. This configuration on the back surface of the ophthalmic lens results in the innermost portion of the second optical zone forming less positive power than the first central zone and thus the power profile shows more positive (p) at the innermost portion of the second optical zone and a less positive (m) at the outermost portion of the second optical zone. Consistent with the embodiment described in FIG. 42, because p=m, about <±20%, the second optical zone is optically normal to the surface and the use of a line to form the second optical zone results in the desired lateral separation of the focal points between the first and second optical zones.

FIG. 44 is a schematic diagram showing an ophthalmic lens incorporating a central optical zone (first optical zone 4401) surrounded by an annular zone (second optical zone 4404) to create an off-axis focal plane 4404*a* and an extended depth of focus 4403 in accordance with certain embodiments. Specifically, the ophthalmic lens of FIG. 44 (A and B) has a central optical zone 4401 forming a coaxial (high intensity) focal point 1A along optical axis 4402 anterior to the retinal image plane 4405, an annular zone 4404 that is relatively positively powered than central zone 4401 and forming a non-coaxial focal point 5 at image plane 4404*a* (in some embodiments, the non-axial points result in a defocus ring appreciated in 3D). Light rays passing through the, through the inner 7, outer 8 and the central portion 9 of the annular zone 4404 intersect the optical axis 4402 to form coaxial focal points 10, 11 and 12 at anterior to retina (10), in between anterior and retinal plane (11) and at the retinal plane (12) respectively.

Figure 44A:
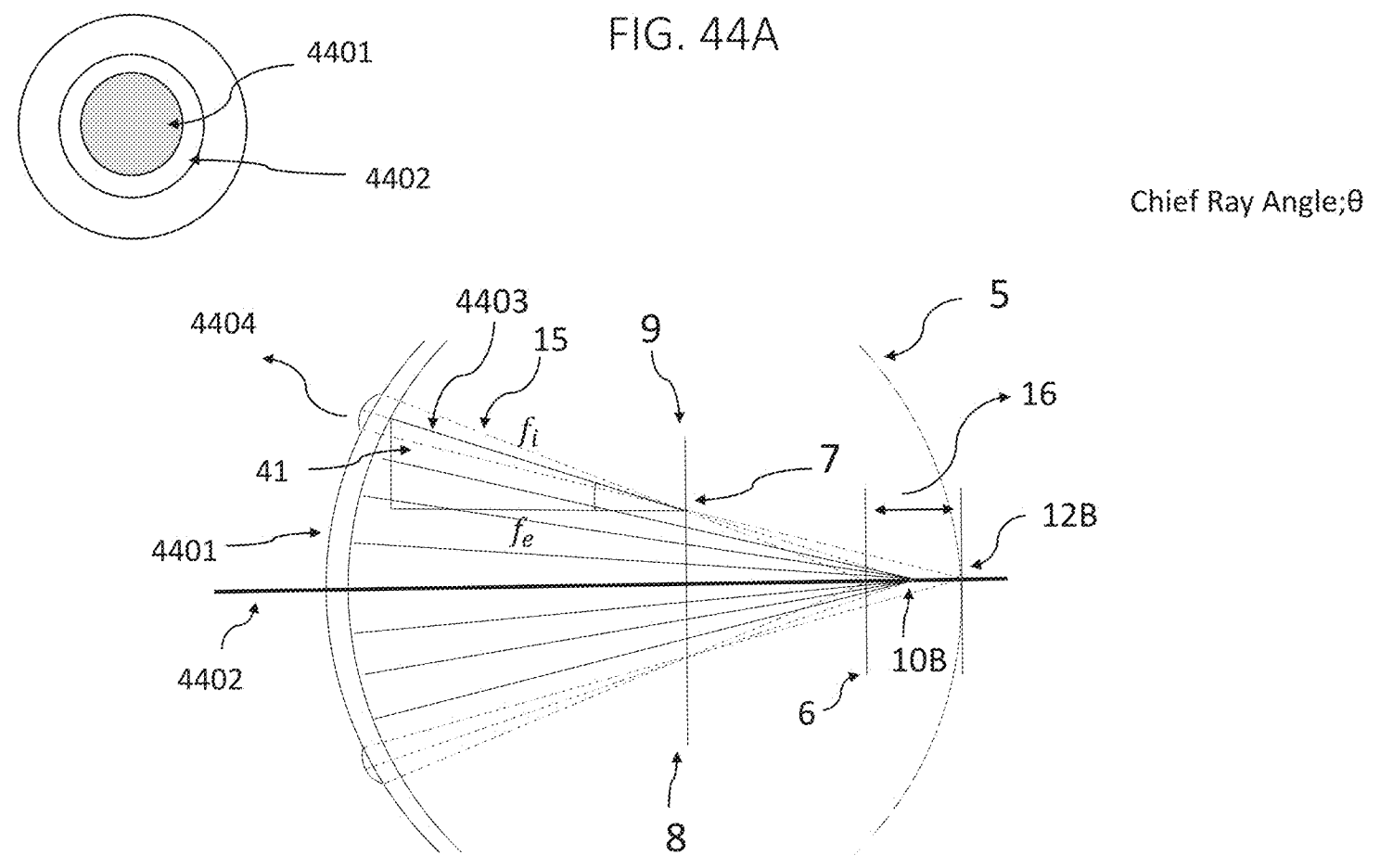
Figure 44B:
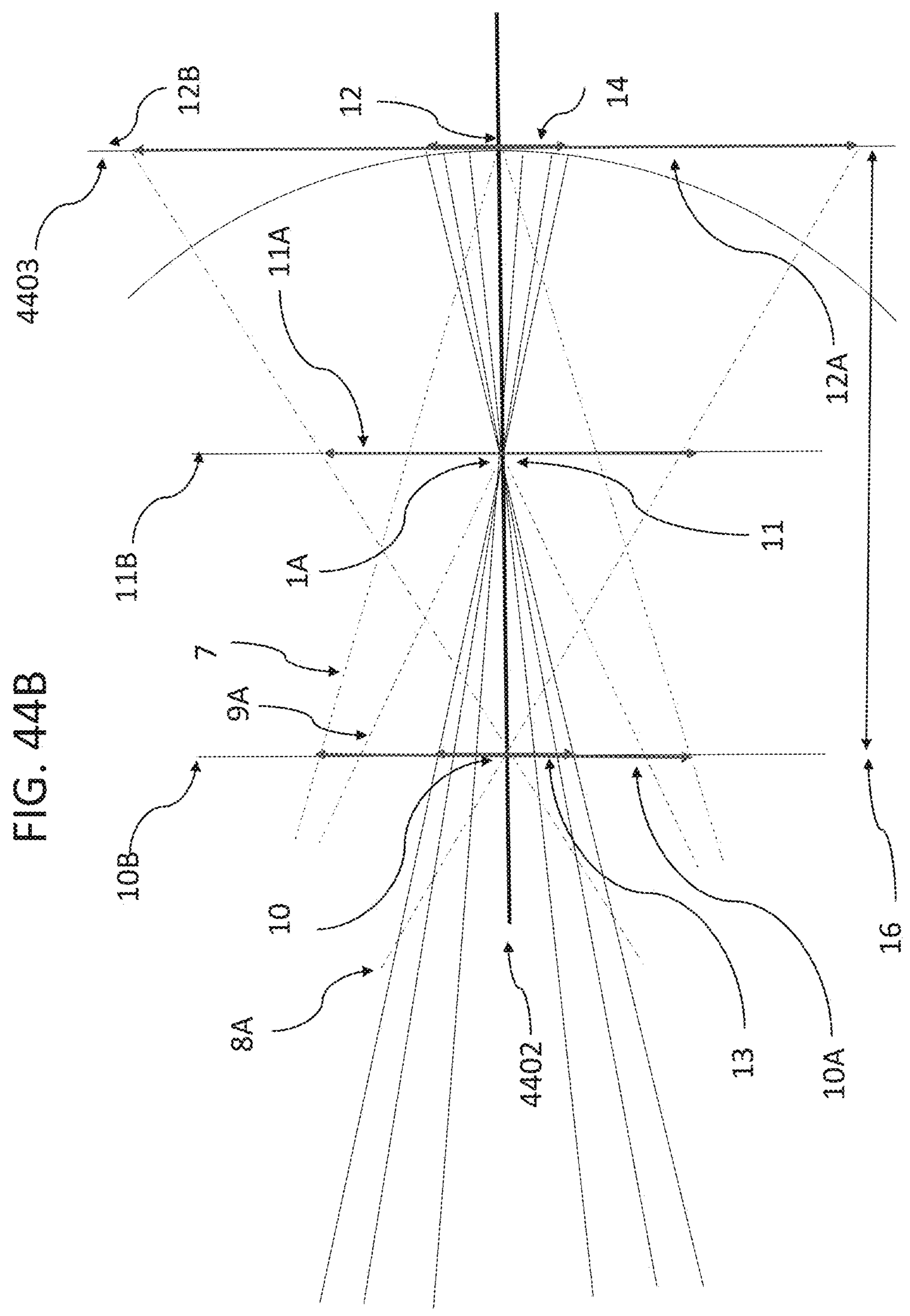

In some embodiments, focal points 10, 11 and 12 may be of lower light intensity than focal point 1A formed by rays passing through first optical zone 4401 whereas in other embodiments they may be of higher light intensity than focal point 1A. In some embodiments, the light intensity of the focal points 10, 11 and 12 may vary from each other. In some embodiments, focal points 10, 11 and 12 may be equally spaced apart from each other whereas in other embodiments, they may not be spaced apart from each other. In the embodiment of FIG. 44(B), the focal points 10, 11 and 12 are not substantially similar in light intensity. The focal point 1A from central optical zone 4401 coincides with the focal point 11 formed by the centermost rays 9 of the annular zone 4404. Light rays passing through the central zone 4401 also form higher intensity light areas 13 and 14 at image planes 10B (anterior to retina) and 12B (at retina) that are of equal size and intensity. Light rays passing through annular zone 4404 to form coaxial focal points 10, 11 and 12 and light intensity areas at 10A, 11A and 12A at image planes 10B, 11B and 12B constructively interfere with light rays from central zone 4401 that form coaxial focal point 1A and light intensity areas 13 and 14 at image planes 10B and 12B to form a depth of focus 4403 extending from image planes 10B to 12B.

In FIGS. 44A and B rays passing through the annular zone 4404, create a relatively myopic (in front of retina) off-axis focal plane 4404*a*, that is anterior to the focal point 1A created by the central optical zone but in some other embodiments, the off-axis focal plane 4404*a* may be in front of, behind or in substantially the same plane as the image plane for rays passing through the central optical zone 11B. In addition, the rays continue and extend beyond the off-axis focal plane to form a depth of focus behind and in front of the central focal point 1A. In some embodiments, the depth of focus 4403 may be entirely in front of 1A or entirely behind the central focal plane 11B. In some embodiments, a portion of the depth of focus 4403 may be in front of and another portion behind the central focal point at 11B. In some embodiments, the ratio of the depth of focus in front versus behind the central focal point may be about 100:0 (entirely in front of the central focal point), 90:10, 80:20, 75:25, 70:30, 60:40, 50:50 (equally in front of and behind the central focal point), 40:60, 30:70, 25:75, 20:80, 10:90, and/or 0:100 (entirely in behind of the central focal point).

The example illustrated in FIG. 44 (A and B) creates a depth of focus that is continuous and in some embodiments improve the image quality in front of the retina compared to behind and may therefore be used for controlling/slowing/reducing the progression of myopia.

In some embodiments, the focal point created by the central or first optical zone may be located on the retinal image plane (or substantially on the retinal image plane), in front of the retinal image plane, and/or behind the retinal image plane.

In some embodiments, rays from the central optical zone 4401 (may have a higher light intensity, relative to rays from the annular optical zone. By positioning the higher intensity rays at the midpoint of the near (most anterior) and distant (most posterior or retinal image) image planes (e.g., at the mid-point of the depth of focus), the effect of these rays on the light spot characteristics may be substantially evenly distributed across the planes encompassing the depth of focus (DOF). In some embodiments, this configuration may result in improved vision at various DOF planes. Additionally, as illustrated in FIG. 44B, as the light rays from the annular zones have lower light intensity, they may have a reduced or lower destructive effect on the near, intermediate, and/or distant planes and therefore may not affect or interfere with vision even when the light is distributed across a larger area. As illustrated, in this embodiment, the interference from light rays created by the annular zone 4404 on the area of light intensity at the anterior most plane from retina (near plane 10B) was less than the interference on the light intensity area formed at the posterior (distant plane 12B) so the image at the near plane may be better than the image at the distant plane.

Figure 45:
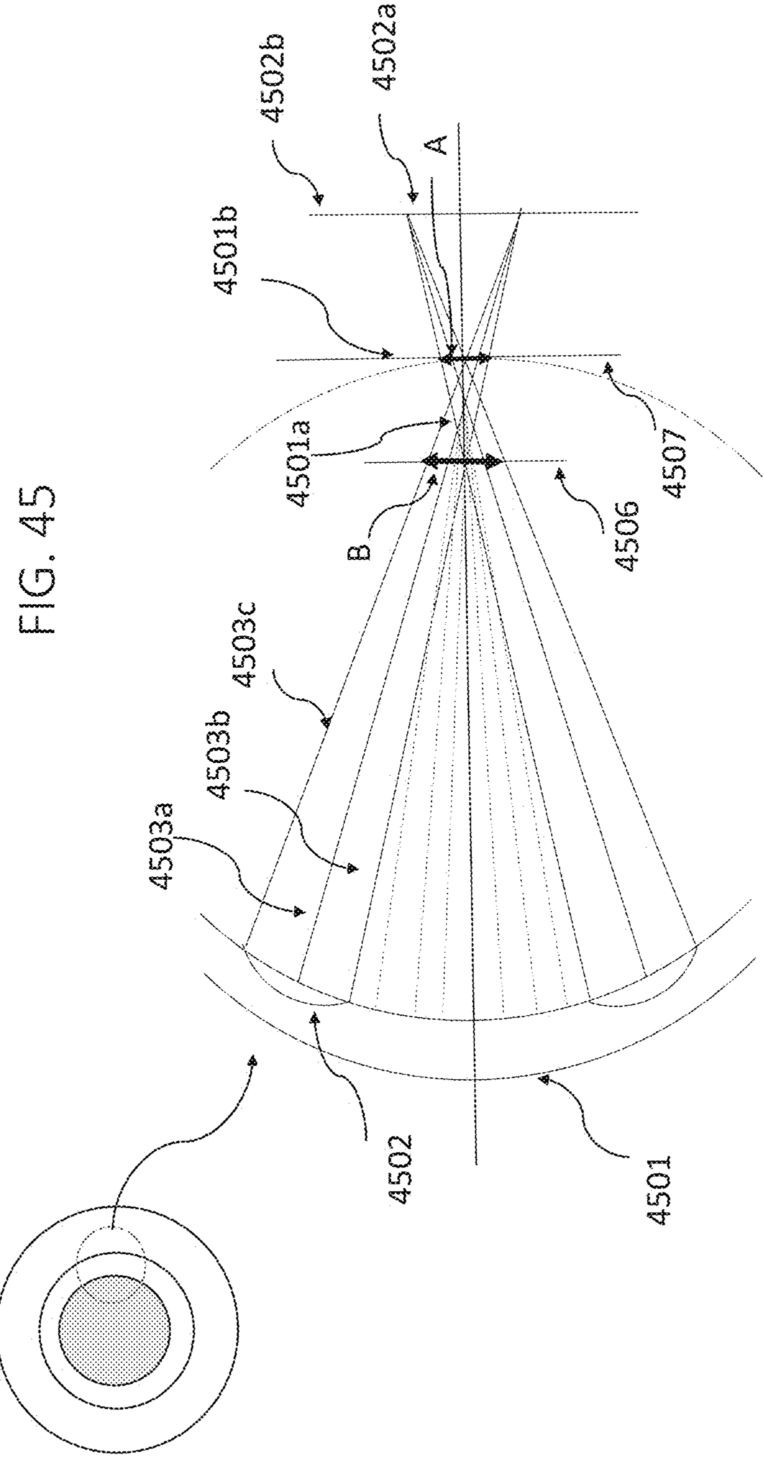
FIG. 45 is a schematic diagram showing an ophthalmic lens incorporating a central optical zone surrounded by an annular zone to create an off-axis focal plane and a depth of focus in accordance with certain embodiments.

FIG. 45 is a schematic diagram of an ophthalmic lens incorporating a central optical zone 4501 surrounded by an annular zone 4502, wherein light rays passing through the annular zone 4502 result in one or more off-axis focal points 4502*a* that interact with the on-axis rays 4501*a* and result in a depth of focus. In FIG. 45, the back surface of the annular optical zone 4502 is relatively more negative powered (steeper curvature) than the back surface of the central zone 4501 and results in the off-axis focal plane 4502*b* to form behind the center zone on-axis focal point 4501*a* and the retinal image plane 4501*b*. The annular zone 4502 may be configured as optically normal to the surface (the annular zone 4502 power profile provides m=p<about ±20% resulting in a) lateral separation of some of the off axis focal points from the on-axis focal points and, b) light rays from the centermost portion of the annular zone 4503*a* being about coincident with the central zone focal point 4501*a* as they intersect the optical axis. Likewise, the light rays from the innermost 4503*b* and outermost 4503*c* portions of the annular zone 4502 form the endpoints of the depth of focus at 4506 and 4507 when they intersect the optical axis equidistant from the center zone focal point 4501*a*. In this configuration, the depth of focus may be located wholly within the eye (i.e., anterior to the retinal plane). However, since the steeper curvature of the back surface of the lens causes the off-axis focal plane 4502*b* to form behind the retina, no off axis focal points (or defocus ring) are formed anterior to the retinal image plane. This configuration may be desirable in some embodiments because the image quality may be improved at the retinal image plane. A lens of this embodiment may result in low light intensity of off-axis focal points 4502*a*, and as the off-axis focal points are positioned posterior to the on-axis image points 4502*a*, there is reduced light interference at A and thus may improve the image quality. This differs from the example of FIG. 44 where the interference of light rays at the light intensity area at the innermost image plane 10B was less than that formed at the retinal image plane 12B.

Figure 46:
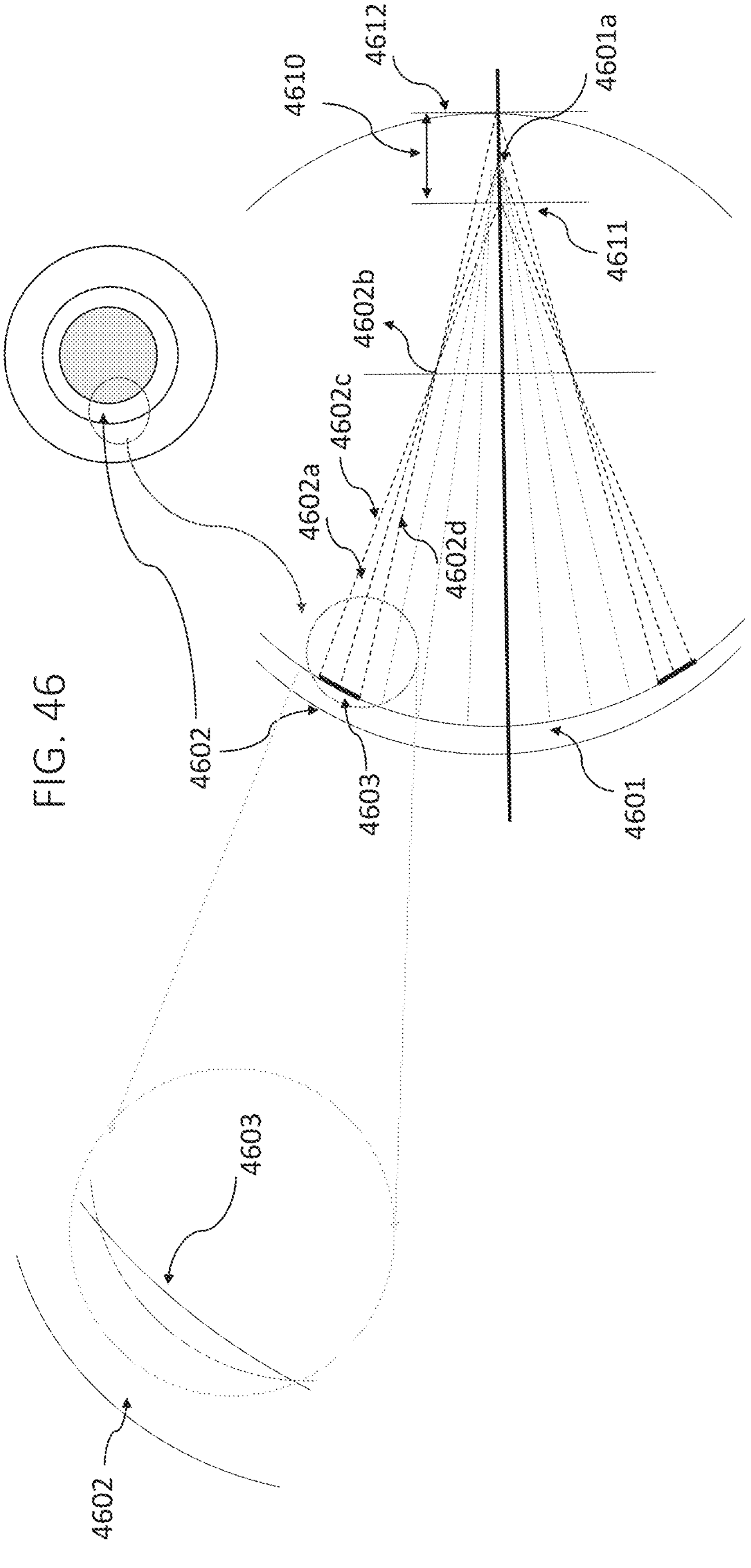
FIG. 46 is a schematic diagram showing an ophthalmic lens incorporating a central optical zone surrounded by an annular zone to create an off-axis focal plane and a depth of focus in accordance with certain embodiments.

In accordance with an embodiment, FIG. 46 is a schematic diagram showing an ophthalmic lens incorporating a central optical zone 4601 surrounded by an annular zone 4602 to create an off-axis focal plane and a depth of focus. As illustrated, light passing through the central zone 4601 forms an on-axis focal point 4601*a* in front of the retinal image plane; the central zone 4601 is surrounded by an annular zone 4602 comprising a flatter back surface curvature (more positive powered than the central optical zone 4601 power). In some embodiments, use of a flatter back surface curvature of the annular zone 4602 may provide a positive power relative to the central optical zone 4601 power and may provide similar results to the embodiment of FIG. 44. Accordingly, the off-axis focal plane 4602*b* is positioned in front of the central focal point 4601*a* and the depth of focus 4610 may be positioned both in front and behind the central focal point 4601*a*. Thus as described herein, the curvature of the annular zone 4602 relative to the central zone 4601 may influence the position of the off-axis focal plane relative to the central focal point and the depth of focus. The exemplary ophthalmic lens in FIG. 46 includes similar characteristics to those of FIG. 44A and 44B. For example, the ophthalmic lens includes a central optical zone 4601 with an on axis focal point 4601*a* not formed on the retinal plane; an annular zone configured as optically normal to the surface (the annular zone power profile provides m=p<about ±20%) resulting in a) lateral separation of one or more off axis focal points from the one or more on-axis focal points and, b) light rays 4602*a* from the centermost portion of the annular zone 4602 being about coincident with the central zone focal point 4601*a* as they intersect the optical axis. Likewise, the light rays from the innermost 4602*d* and outermost 4602*c* portions of the annular zone 4602 form the endpoints of the depth of focus at 4612 and 4611 when they intersect the optical axis equidistant from the center zone focal point 4601*a*. In this configuration the depth of focus may be located wholly within the eye (i.e., anterior to the retinal plane). In some embodiments, the configuration of the ophthalmic lens of FIG. 46 where the back surface of the annular zone 4602 has a flatter curvature 4603 than the central optical zone 4601 curvature may be desirable because the sag difference may be reduced between optical zones and the surface is not recessed into the lens. Such a configuration may be less visible and therefore may be more cosmetically appealing and may increase compliance to lens wear. Additionally, in some embodiments, the flatter back surface curvature of the annular zone 4602 may be more suitable to manufacturing processes such as freeform lens manufacturing, thus reducing cost and increasing flexibility in lens production.

Figure 47:
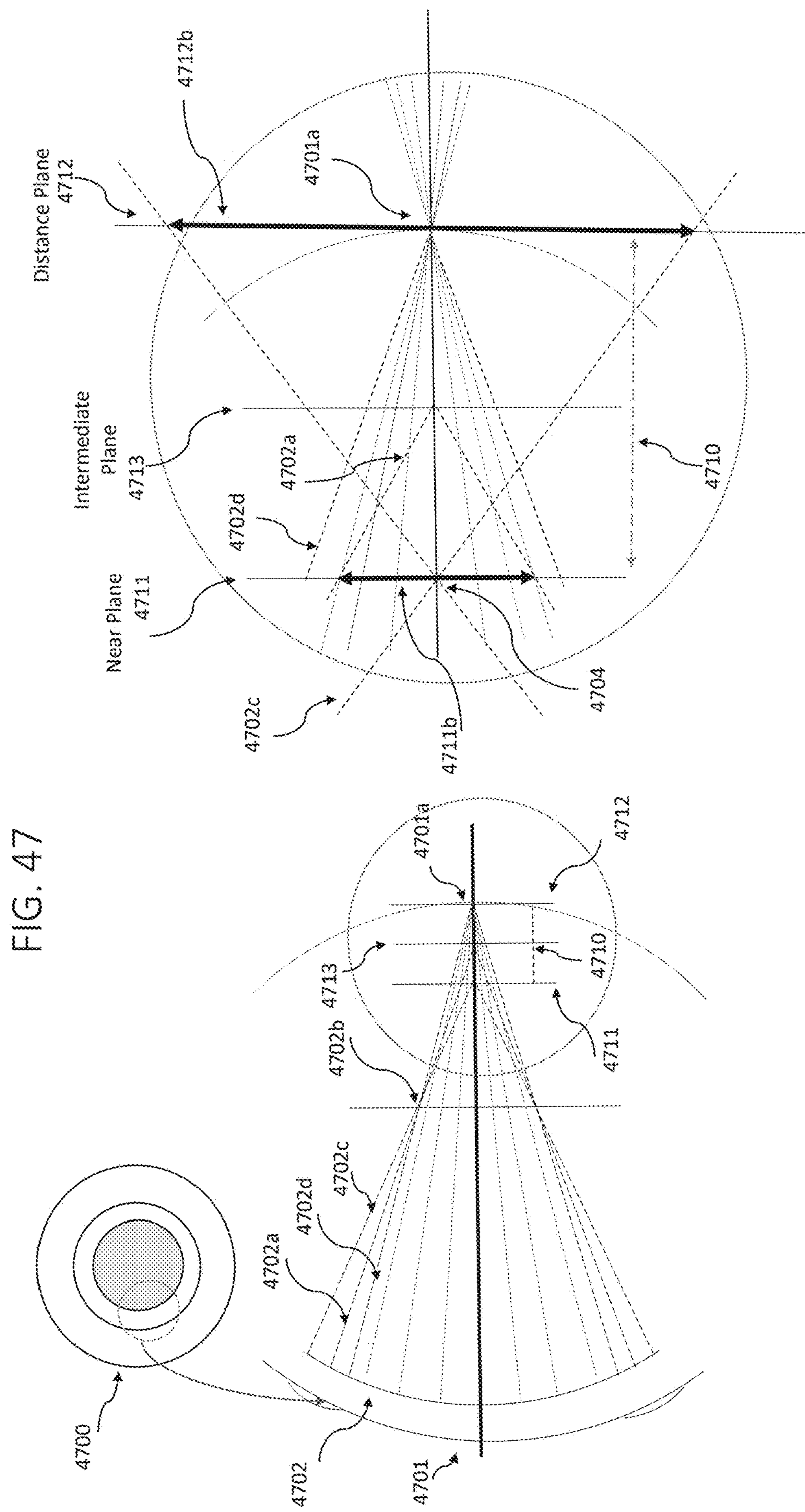
FIG. 47 is a schematic diagram showing an ophthalmic lens incorporating a central optical zone surrounded by an annular zone to create an off-axis focal plane and a depth of focus in accordance with certain embodiments.

In accordance with an embodiment, FIG. 47 is a schematic diagram showing an ophthalmic lens incorporating a central optical zone 4701 surrounded by an annular zone 4702 to create an off-axis focal plane and a depth of focus. As illustrated, light passing through the central optical zone 4701 forms a focal point 4701*a* at the retinal image plane and, the annular zone 4702 may include a tilted curvature so that the depth of focus 4710 is located wholly within the eye. Accordingly, this embodiment may provide different results to the embodiment of FIG. 44. For example, the central optical zone 4701 incorporates a power that corrects for the distance refractive error and therefore the central focal point 4701*a* is located substantially at the retinal image plane 4712. The off-axis focal plane 4702*b* is positioned in front of the central focal point 4701*a*, however the depth of focus 4710 may also be positioned more anteriorly to the central focal point 4701*a* when the annular zone 4702 is not configured optically normal to the surface (the annular zone power profile m=p>±20%). Thus the lateral separation of the off axis focal point 4702*b* from the on-axis focal point 4701*a* may result in light rays from the innermost 4702*d* portion of the annular zone 4702 being about coincident with the central zone focal point 4701*a* as they intersect the optical axis at the retinal image plane. Now the light rays at the retinal plane 4701*a* and and the light rays from the outermost 4702*c* portions of the annular zone form the endpoints of the depth of focus at 4712 and 4711. The light rays from the centermost portion 4702*a* of the annular zone now intersect the optical axis equidistant from the endpoints of the depth of focus. In this configuration, the depth of focus for the illustrated embodiment may be located wholly within the eye (i.e., anterior to the retinal plane) however, unlike FIG. 44, the central zone focal point 4701*a* in FIG. 47 is now at the retinal plane and is not coincident with the centermost rays of the annular zone 4702 as they intersect the optical axis. The change in power profile in the annular zone has altered the m:p ratio such that p>m and the depth of focus may be shifted more anteriorly in front of the retina to avoid any focal points behind the retina. However, in some embodiments, this may result in increased interference of the high intensity light rays at the near image plane 4711 which may degrade the near image plane image quality and may also adversely affect the image quality at the distance image plane 4712 (e.g., as compared to the example described in FIG. 44).

Figure 48:
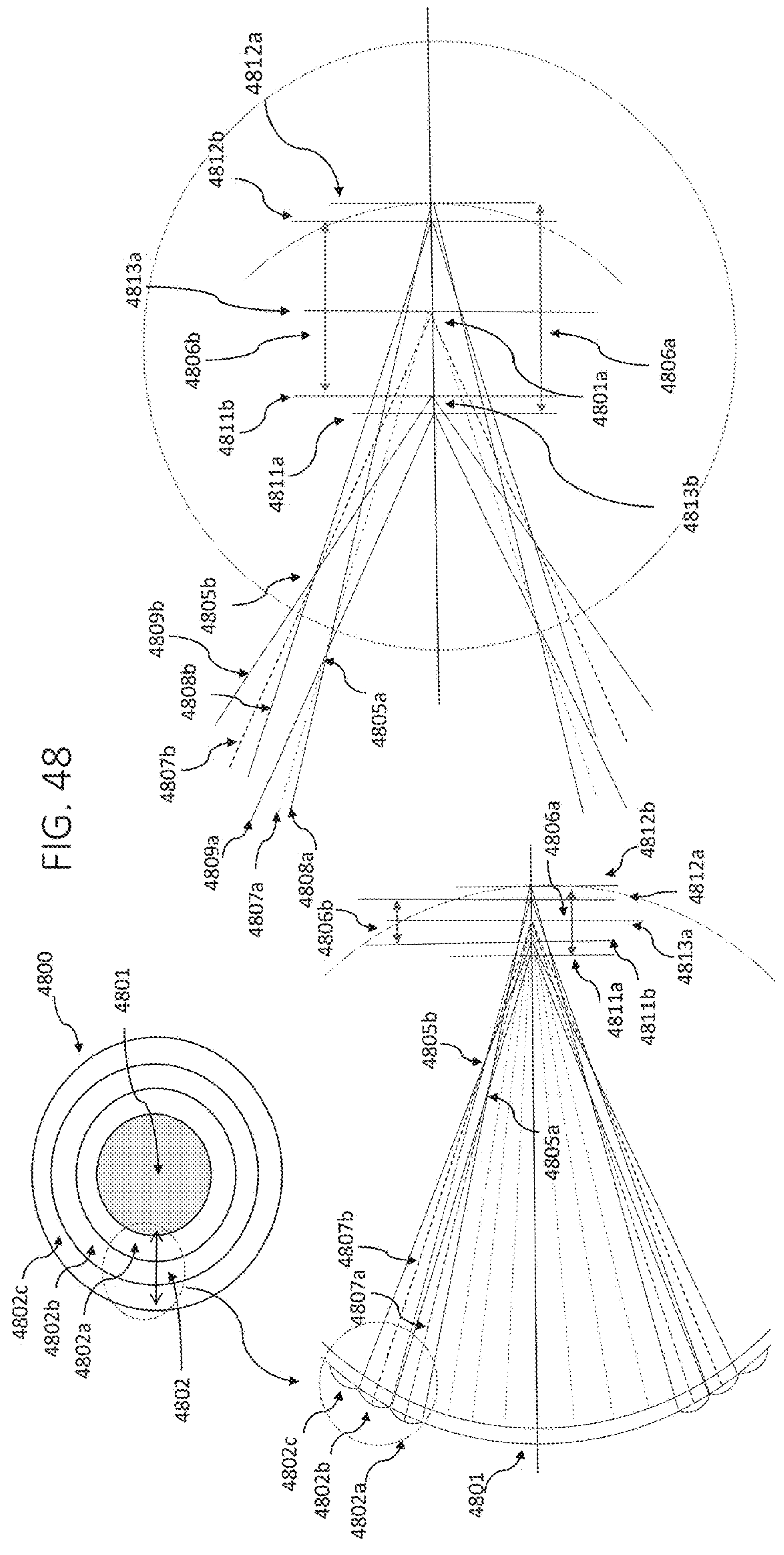
FIG. 48 is a schematic diagram showing an ophthalmic lens incorporating a central optical zone surrounded by an annular zone to create an off-axis focal plane and a depth of focus in accordance with certain embodiments.

In accordance with an embodiment, FIG. 48 is a schematic diagram showing an ophthalmic lens 4800 with a central optical zone 4801 and an annular zone 4802 to create one or more off-axis focal planes and a depth of focus. The annular zone 4802 comprises three conjoined curvatures 4802*a*, 4802*b* and 4802*c* (as opposed to a single curvature) that are substantially similar in curvature. With a conjoined curve, the inner most and the outer most portion of the curve transition to the base curve (curvature of the first optical zone). For simplicity, description is provided for light rays through the first two conjoined curvatures 4802*a* and 4802*b*. Light rays passing through the central zone 4801 form an on axis focal point 4801*a* at 4813*a* and located in front of the retinal image plane 4812*a*. Light rays passing through the conjoined curvatures 4802*a* and 4802*b* of the annular zone 4802 may create off-axis focal planes 4805*a* and 4805*b* and a depth of focus 4806*a* and 4806*b* respectively. The conjoined curvatures of the annular zone 4802 are on the front surface and may have a steeper curvature than the curvature of the central optical zone 4801 (results in relatively positive powered zone 4802 than the central optical zone power). In some embodiments, each conjoined curvature may perform similarly compared to the single curvature in the annular optical zone of FIG. 44. The off-axis focal planes 4805*a* and 4805*b* may be positioned in front of the central focal point 4801*a* and the depth of focus 4806*a* and 4806*b* for each conjoined curvature may be positioned on either side of the central focal point 4801*a* (i.e. both in front and behind). In some embodiments, the conjoined curvatures may be on the front surface or on the back surface or both surfaces. Additionally, as described herein, the curvature of the annular zone 4802 relative to the central optical zone 4801 may influence the position of the off-axis focal plane relative to the central focal point and the depth of focus. As configured, light rays passing through the central optical zone 4801 form an on axis focal point 4801*a* in front of the retinal plane; the annular zone 4802 is configured with conjoined curvatures 4802*a* and 4802*b* optically normal to the surface (the power profile in each conjoined curve provides m=p, about <±20%) and light passing through the annular zone 4802 result in off axis focal points 4805*a* and 4805*b*; the lateral separations of the off axis focal points 4805*a* and 4805*b* from the on-axis focal point 4801*a* may result in light rays from the centermost portion 4807*a* and 4807*b* of each conjoined curve in the annular zone being about coincident with the central zone focal point 4801*a* as they intersect the optical axis. Likewise, light rays passing through the innermost 4808*a* and 4808*b* and outermost 4809*a* and 4809*b* portions of the annular zone form the endpoints of the depth of focus at 4812*a* and 4811*a* when they intersect the optical axis equidistant from the center zone focal point 4801*a*. In this configuration, the depth of focus 4806*a* and 4806*b* for the illustrated embodiment may be located wholly within the eye (i.e., anterior to the retinal plane). A magnified view of the light rays intersecting three image planes forming the depth of focus is shown in FIG. 48. The central zone focal point 4801*a* is located at the intermediate image plane 4813*a* and is about coincident with light rays 4809*a* and 4809*b* formed by the centermost portions of the conjoined curvatures 4802*a* and 4802*b*. The near image plane 4811*a* and distant image plane 4812*a* from the first conjoined curvature 4802*a* and thus the depth of focus 4806*a* may be slightly longer than the depth of focus 4806*b* formed by the second conjoined curvature 4802*b* between image planes 4813*b* and 4812*b*. However, the light interference at image planes 4811 (*a* and *b*), 4812 (*a* and *b*) and 4813*a* from light rays originating from the central zone 4801 and the first conjoined curvature (about 5 mm aperture) may be similar to the light interference at the same three image planes from light rays originating from the central zone and the both conjoined curvatures combined (about 7 mm aperture). In some embodiments, the slight difference in depth of focus formed by the conjoined curvature 4802*a* and 4802*b* may be due to the more peripheral location of the second conjoined curvature relative to the center of the lens. In some embodiments, the off-axis optical power of the conjoined curvature may decrease as each curvature is located farther from the center zone. The illustration demonstrates that when the annular zone is increased in widthe, the conjoined curvatures may continue to provide good image quality and depth of focus. A desirable feature of conjoining multiple annular curvatures is that a larger area of the annular optical zone surrounding the central optical zone may be devoted to extending the depth of focus. The ophthalmic lens of FIG. 44 may in some embodiments provide an optimal image quality for a pupil size of 5 mm when the central optical zone 4401 has a diameter of 3 mm and the annular zone 4404 has a width of 1.0 mm. However, at larger pupil sizes, i.e. about 6 mm or more, light rays may pass through the third optical zone (comprising similar optical power as the central optical zone) of the ophthalmic lens of FIG. 44 to contribute additional high intensity focal points and may increase the interference with the image quality at important image planes. In addition, in some embodiments, the lens described in FIGS. 44A and 44B may also have a second annular zone surrounding the first annular ring forming a coaxial focal point coincident with the focal point formed by the center zone. For larger pupil sizes, the coaxial light rays forming the on axis focal point from the second annular ring may fall within the pupil and increase the light intensity area formed at an image plane e.g. the retinal image plane. Thus, in some embodiments, it may be advantageous to provide a wider annular zone than provided in FIG. 44. However, increasing the width of the annular zone using a single curvature e.g. by 0.50 mm or more to 1.50 mm or wider may result in increased light interference at various image planes and degrade image quality as an optically normal to the surface condition (where the annular zone power profile provides m=p<about ±20%) may not be maintained over wider annular optical zones. Thus to maintain good image quality over larger annular optical zones, multiple conjoined annular zones having individual widths that substantially maintain the optical normal to the surface condition (i.e. m=p, <about ±20%) result in improved image quality and depth of focus. Therefore, an exemplary embodiment of FIG. 48 may provide an improved depth of focus and an improved and consistent image quality especially in eyes with larger pupils or where the variation in pupil size is substantial (as with varying illumination).

In some embodiments, the multiple conjoined curvatures of the ophthalmic lens of FIG. 48 may increase the depth of focus beyond an annular optical zone comprising a single curvature. For example, the depth of focus produced by conjoined curvatures 4802*a*, 4802*b* and 4802*c* may be further extended by using a higher dioptric power in each curvature e.g. +4.00 D. Thus in some embodiments, the conjoined zone design of FIG. 48 may be applicable to myopia treatment, by extending the area and light intensity over image planes located in front of the retinal image plane. Likewise, in some embodiments, an annular zone comprising multiple conjoined curvatures may be applicable for presbyopic correction. For a presbyope, the required depth of focus that enables vision from far to near may be dependent on the degree of their presbyopia. An early presbyope may require lesser depth of focus as their residual ocular accommodation may support focusing at intermediate distances of up to 50 or 60 centimeters whereas an advanced presbyope, with minimal residual ocular accommodation may require a longer depth of focus. Therefore in some embodiments, an annular optical zone comprising only two conjoined curvatures may be sufficient for early or middle presbyopes whereas three or more conjoined curvatures may be required for higher add presbyopes. Additionally, a longer depth of focus from far vision up to 30-40 centimeters may be needed for advanced presbyopes. In addition to multiple conjoined curvatures, an increase in dioptric power in each curvature may add depth beyond the single annular optical zone. Thus the amount of power in each conjoined curvature and the increased area devoted to depth of focus may be manipulated to lengthen depth of focus accordingly while still providing an optimal image quality at intermediate and close distances.

In some embodiments the annular zone may comprise 2, 3, 4, 5, 6, 7, 8, 9, and/or 10 conjoined curvatures. In some embodiments, conjoined curvatures may be created using multiple single curvatures placed adjacent to each other. In some embodiments, this design may create multiple myopic treatment planes (e.g., multiple off-axis focal planes). In some embodiments, one or more of the myopic treatment planes may not be positioned off-axis. In some embodiments, the multiple myopic treatment planes may be utilized to add more depth of focus for use with presbyopic vision and/or extra myopic treatment In accordance with an embodiment, FIG. 49 (A and B) is a schematic diagram of an ophthalmic lens 4900 with a central optical zone 4901 and an annular zone 4902 to create one or more off-axis focal planes and a depth of focus. The annular zone 4902 comprises multiple infused curvatures 4902*a*, 4902*b*, 4902*c* and 4902*d* (as opposed to a single curvature) with each having the same curvature except 4902*d* which is wider and has a steepr curvature. An infused curvature refers to either a partial or an incomplete ring that has an innermost portion and/or an outermost portion that may not meet the base surface (central optical zone) curvature and differs from e.g., a conjoined curvature where the ring is complete and the inner and outermost portions of the ring generally meet the base curvature (and may be symmetric). In some embodiments, an annular zone comprising multiple infused curves may have a first infusion where the innermost portion of the first (innermost) infusion curve meets the base surface curvature and the outermost portion of the last (outermost) infusion curve of the annular zone meets the base surface (or the surface of the next optical zone) but the infusion curves in between may not have a portion that meets the base surface curvature. In some embodiments, the first curve infusion may not be geometrically or optically normal to the surface because the innermost portion may be on the base surface, however, the outermost portion may not be geometrically or optically normal to the surface as it transitions to the next infused curve.

For simplicity and ease of illustration, light rays from the first, second and last curvature infusion 4902*a*, 4902*b* and 4902*d* will be described. The central zone 4901 forms an on-axis focal point 4901*a* in front of the retinal image plane 4912*b*. The curvature infusions 4902*a*, 4902*b* and 4902*d* may create off-axis focal planes 4905*a*, 4905*b* and 4905*d* and a depth of focus 4906*a*, 4906*b* and 4906*d* in accordance with certain embodiments. In this example, the curvature infusions in the annular zone 4902 are on the front surface and may have a steeper curvature than the central optical zone 4901 curvature ((e.g., a more positive powered than the central optical zone power). The curvature infusions shape and sagittal depth may be seen magnified in 49-1 and are similar except for the 4902*c* as noted above. The degree of infusion between each curvature is determined by the amount of overlap between the curvatures e.g. distance 4914, 4915 and 4916. The extent of infusion in the annular zone 4902 between the first and second infusions 4902*a* and 4902*b* (4914) and between the third and last infusions 4916 and between the second and third infusions (4915) are similar. In some embodiments, the extent of overlap controls the diameter of each infusion, symmetry and the contributions of light rays providing depth of focus and interference to image planes formed by the ophthalmic lens 4900.

Figure 49A:
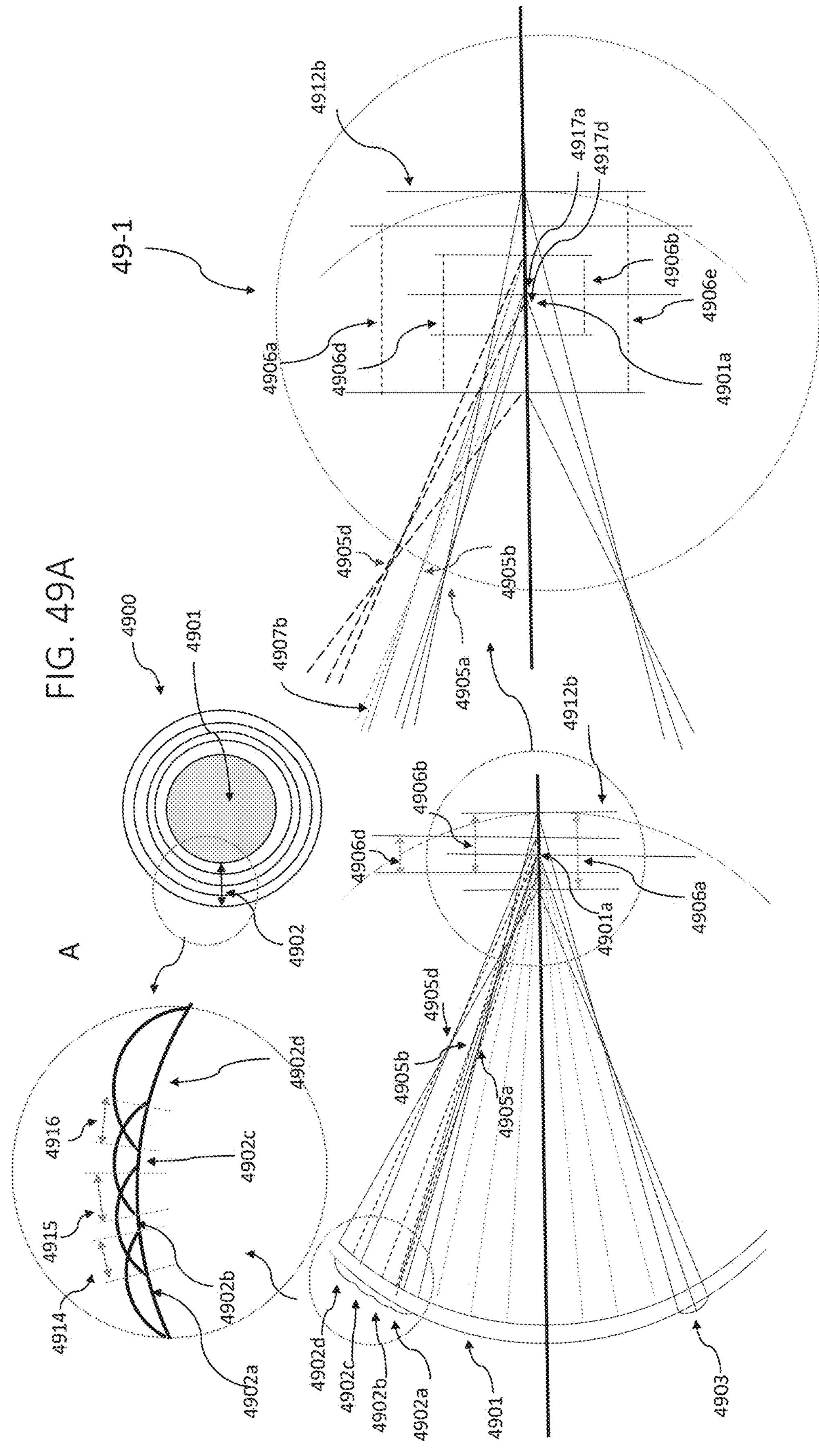

In some embodiments, e.g. FIG. 49A, the off-axis focal planes formed by the curvature infusions 4902*a*, 4902*b* and 4902*d* may be positioned in front of the central focal point 4901*a* and the depth of focus 4906*a*, 4906*b* and 4906*d* for each curvature infusion may be positioned both in front and behind the central focal point 4901*a*. In some embodiments the annular zone 4902 may be located on the back surface of the ophthalmic lens and may have multiple curvature infusions and still create similar or substantially similar results. Additionally, as described herein, the curvature of the annular zone relative to the center zone may influence the position of the off-axis focal plane relative to the central focal point and the depth of focus. In some embodiments the spherical geometry discussed herein may be utilized to obtain the features described herein and in some embodiments other techniques may be utilized.

As configured, the exemplary ophthalmic lens in FIG. 49A includes a central optical zone 4901 with an on axis focal point 4901*a* not formed on the retinal plane (e.g., in front of the retinal plane); an annular zone configured with infused curvatures 4902*a*, 4902*b* and 4902*d* where only 4902*b* (and 4902*c*) is optically normal to the surface (where the power profile in each curvature provides m=p, <about ±20%). Thus, in some embodiments e.g., FIG. 49A, the first infusion curvature 4902*a* may have a power profile where m:p>20% i.e. not optically normal to the surface, and likewise the last infusion 4902*d* may have a similar and opposite power profile where m:p>20% and not optically normal to the surface as depicted in FIG. 49B.

As in FIG. 49A, the lateral separations of the off axis focal points 4905*a*, 4905*b* and 4905*d* from the on-axis focal point 4901*a* may result in only the light rays from the centermost portion 4907*b* of the second curvature infusion (4902*b*) being about coincident with the central zone focal point 4901*a* as they intersect the optical axis and the depth of focus formed is 4906*b*. As the infused curves 4902*a* and 4902*d* are not configured optically normal to the surface, light rays passing through the centermost portions of the infused curves do not intersect the optical axis at 4901*a* but rather at 4917*a* and 4917*d*. The depth of focus formed by the infusion curvatures 4902*a* and 4902*d* are 4906*a* and 4906*d*. In this configuration, the depth of focus for each infusion curvature of the ophthalmic lens 4900 may be located wholly within the eye (i.e., anterior to the retinal plane). A magnified view of the light rays intersecting the image planes forming the depth of focus is shown in FIG. 49-1A. Each infused curvature may create a different depth of focus. For example, the depth of focus 4906*b* of the second infusion curve configured normal to the surface is shorter than the depth of focus 4906*a* formed by the first infusion curvature and the depth of focus 4906*d* formed by the second infusion curvature. Furthermore, neither of these depths of focus 4906*a* and 4906*d* lie equidistant around the on axis focal point of the center zone 4901*a*. Depth of focus 4906*a* is longer and shifted more anteriorly while 4906*d* is shifted more posteriorly but shorter than 4906*a* because of the infusion curvature located further from the lens center. Compared to the depth of focus 4906*e* formed by the annular zone comprising a single curvature all of depth of focus formed by the infusion curvatures were less extended.

The width of the infused curves may be narrower than either the multiple conjoined curves or an annular zone including a single curvature and therefore may provide a shorter depth of focus per each infused curve. However, in an ophthalmic lens formed with multiple narrower infusion curves that are configured appropriately, the total depth of focus may be maintained or may exceed the depth of focus obtained with either a single annular zone or several multiple, conjoined zones. Thus an ophthalmic lens incorporating multiple infused curves in an annular zone may be as advantageous as the example of FIG. 48 and in some embodiments may provide further improvements. In some embodiments, a lateral separation of the off-axis focal points from the on-axis focal point obtained with an ophthalmic lens with multiple infused curves may be the same or may be different. In some embodiments, the infusion curvatures may be created with substantially the same or substantially different curvatures or may include 'lines' adjacently placed or interspersed between curvatures. In some embodiments, all the infusion curvatures may be formed with the optical power profile as shown in FIG. 49B where the infusion curvatures, except for the first and the last, may fulfill the optical normal to the surface condition where m=p<about ±20%. In some embodiments, the infusion curvatures may be tailored to provide a power profile with a range of m and p ratio conditions. Thus, infusion curvatures, because of their narrow dimension, may provide the lens designer more flexibility in delivering a desired image quality and depth of focus. For example, utilizing multiple infused curves an annular zone may not be geometrically normal to the surface but may provide a power profile where m=p<about 20% fulfilling the condition of optically normal to the surface and thus may be configured to provide an optimal depth of focus and image quality at the respective image planes with the least amount of interference between light rays. The ophthalmic lens may provide more beneficial vision, with for example, an extended depth of focus sufficient for an advanced presbyope or a more consistent image quality for a presbyope with a larger pupil and in those who may experience wider fluctuations in their pupil size across different lighting conditions. In some embodiments, utilizing multiple infusion curvatures to form an annular zone may enable a continuous surface to be formed with the center zone and simultaneously may provide a continuous power profile substantially free of discontinuities.

In some embodiments the annular zone may comprise 2, 3, 4, 5, 6, 7, 8, 9, and/or 10 curve infusions. In some embodiments, the multiple curve infusions may decrease the depth of focus provided by the annular zone but may provide a more pupil independent design. The multiple curve infusions may also allow the overall width of the annular zone to be increased without affecting the depth of field. In some embodiments, the multiple curve infusions may also create an optically significant non-normal to surface design. In some embodiments, the multiple curve infusions may have similar or identical optical properties. As illustrated in FIG. 49B, the multiple curve infusions may also have different optical properties. For example, based on a normalized base lens aberration profile, the curve infusions may have different m and/or p power values. As illustrated, in FIG. 49B the power profile of the first (closest to center) infused curve may have an m negative power (m-a) that is significantly more than the p-a positive power. Likewise, the power profile of the last (furthest from the center) infused curve D may have an m negative power (m-d) that is significantly less than the p-d positive power while the power profile of the middle two (second and third) infused curves B and C may have m negative powers (m-b and m-c) that are about equal to the p-b and p-c positive power values, respectively. Thus, the power profiles of infused curves B and C are optically normal to the surface. In addition, the positive and negative power profile of the first infused curve A may be longer than the power profile of the second, third etc. infused curves e.g. curves B, c and D. This may be created by the asymmetry of a curve infusion. A curve infusion is asymmetric when the innermost portion of a curve infusion is at a different sagittal height than the outermost portion. As described earlier, the first and last curve infusion of FIG. 49A are asymmetric and provide powers of m=p>±20%.

Figure 50:
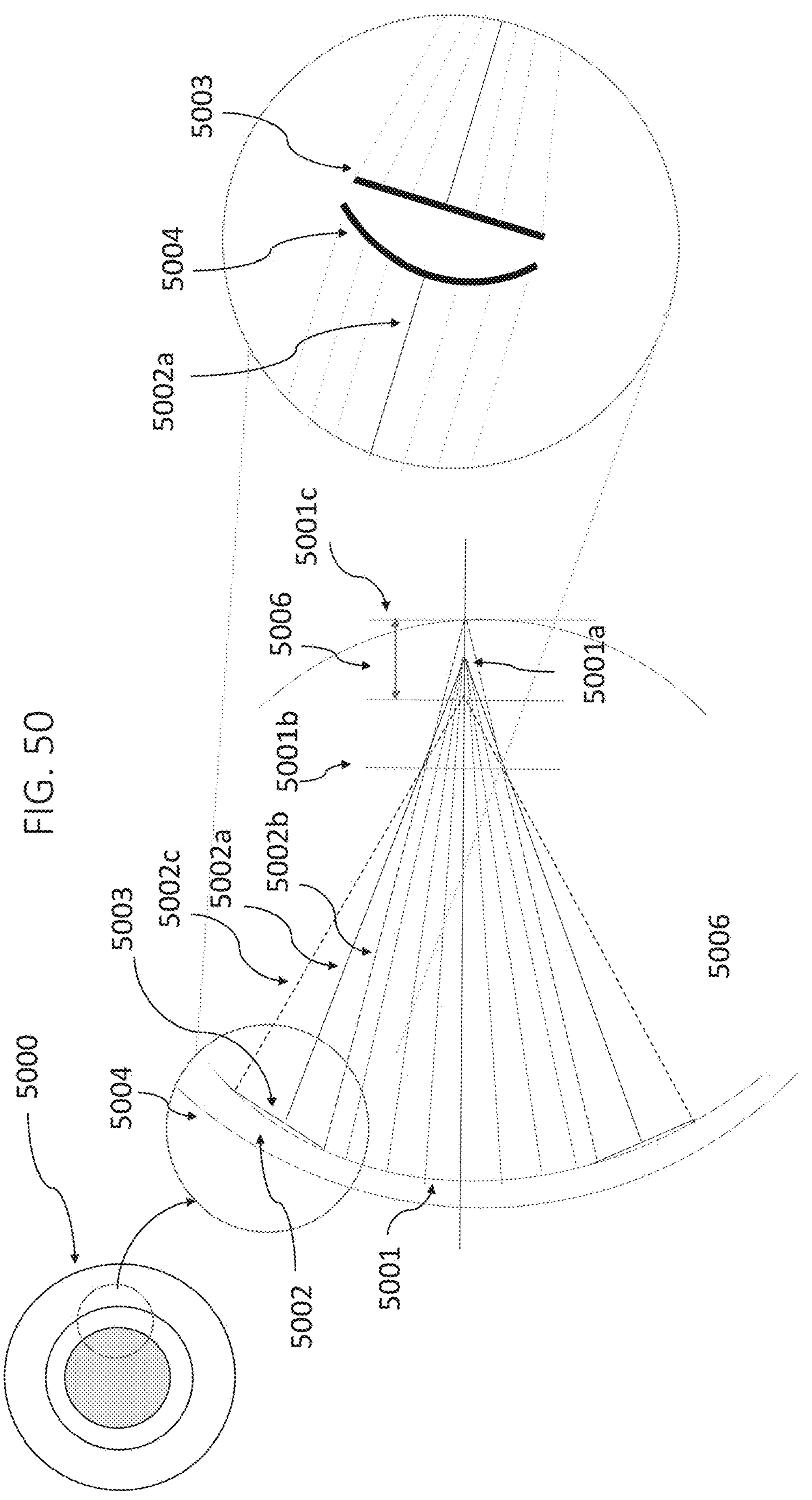
FIG. 50 is a schematic diagram showing an ophthalmic lens incorporating a central optical zone surrounded by an annular zone to create an off-axis focal plane and a depth of focus in accordance with certain embodiments.

In accordance with an embodiment, FIG. 50 is a schematic diagram showing an ophthalmic lens 5000 with a central optical zone 5001 and an annular second optical zone 5002 to create an off-axis focal plane and a depth of focus. In some embodiments, the annular second optical zone 5002 may be created by utilizing a surface with nil or substantially nil curvature (referred to as line curvature herein) and forms a more positive powered annular zone 5002 than the central optical zone power 5001. In some embodiments, the line may combine with the curvature of the front surface resulting in the ophthalmic lens functioning as a plano-convex lens and creating a desired off-axis image plane 5001*b* located in front of or behind the central optical zone focal point 5001*a* (but in front of the retinal image plane 5001*c*). In some embodiments, this design may create a relatively similar amount of depth of focus but using a much smaller annular width (e.g., by a factor of about 5, 10, or 15 for a contact lens design). In some embodiments, this design may also be used in combination with the infused and/or conjoined curvatures described herein. While the line may be applicable to all ophthalmic lenses, when utilized in a contact lens, the line curvature may be very narrow e.g. 50 um wide and may produce very high off axis powers e.g. >50 D or about 100 D and so the light rays emerging from such an off axis focal point of that power may be highly dispersive and may reduce contrast despite have an extended depth of focus. Applied to a spectacle lens, a line of around 1 mm may provide an off axis power of around 5.0 D, while also maintaining a depth of focus.

In some embodiments, the ophthalmic lens 5000 may provide similar results to the lens of FIG. 44 (A and B) by using a line (a non-spheroidal torus) on the back surface of the lens. In other words, several forms of non-spheroidal torus rotated around a surface of the ophthalmic lens may increase the positive power in the annular optical zone relative to the central optical zone power that is required to create an off-axis focal plane and a depth of focus in accordance with certain embodiments. In some embodiments, a non-spheroidal torus e.g. a line or a concroid or conjoined or infused curves or lines or lines and curves interspersed in an annular zone may be utilized to obtain the features described herein and in some embodiments other techniques may be utilized. Accordingly, the off-axis focal plane 5001*b* is positioned in front of the central focal point 5001*a* and the depth of focus 5006 may be positioned both in front and behind the central focal point 5001*a*. Additionally, as described herein, the curvature of the annular zone relative to the center zone may influence the position of the off-axis focal plane relative to the central focal point and the depth of focus.

The exemplary ophthalmic lens in FIG. 50 includes similar characteristics to those of FIG. 44 (A and B). For example, the ophthalmic lens includes a central optical zone 5001 with an on axis focal point 5001*a* not formed on the retinal plane (e.g., in front of the retinal plane); an annular zone 5002 configured by a line as optically normal to the back surface (where the annular zone power profile provides m=p, <about ±20%) so that the lateral separation of the off axis focal point from the on-axis focal point may result in light rays 5002*a* from the centermost portion of the annular zone being about coincident with the central zone focal point 5001*a* as they intersect the optical axis. Likewise, the light rays from the innermost 5002*b* and outermost 5002*c* portions of the annular zone form the endpoints of the depth of focus 5006 when they intersect the optical axis equidistant from the center zone focal point 5001*a*. In this configuration the depth of focus for the illustrated embodiment may be located wholly within the eye (i.e., anterior to the retinal plane).

Figure 51A:
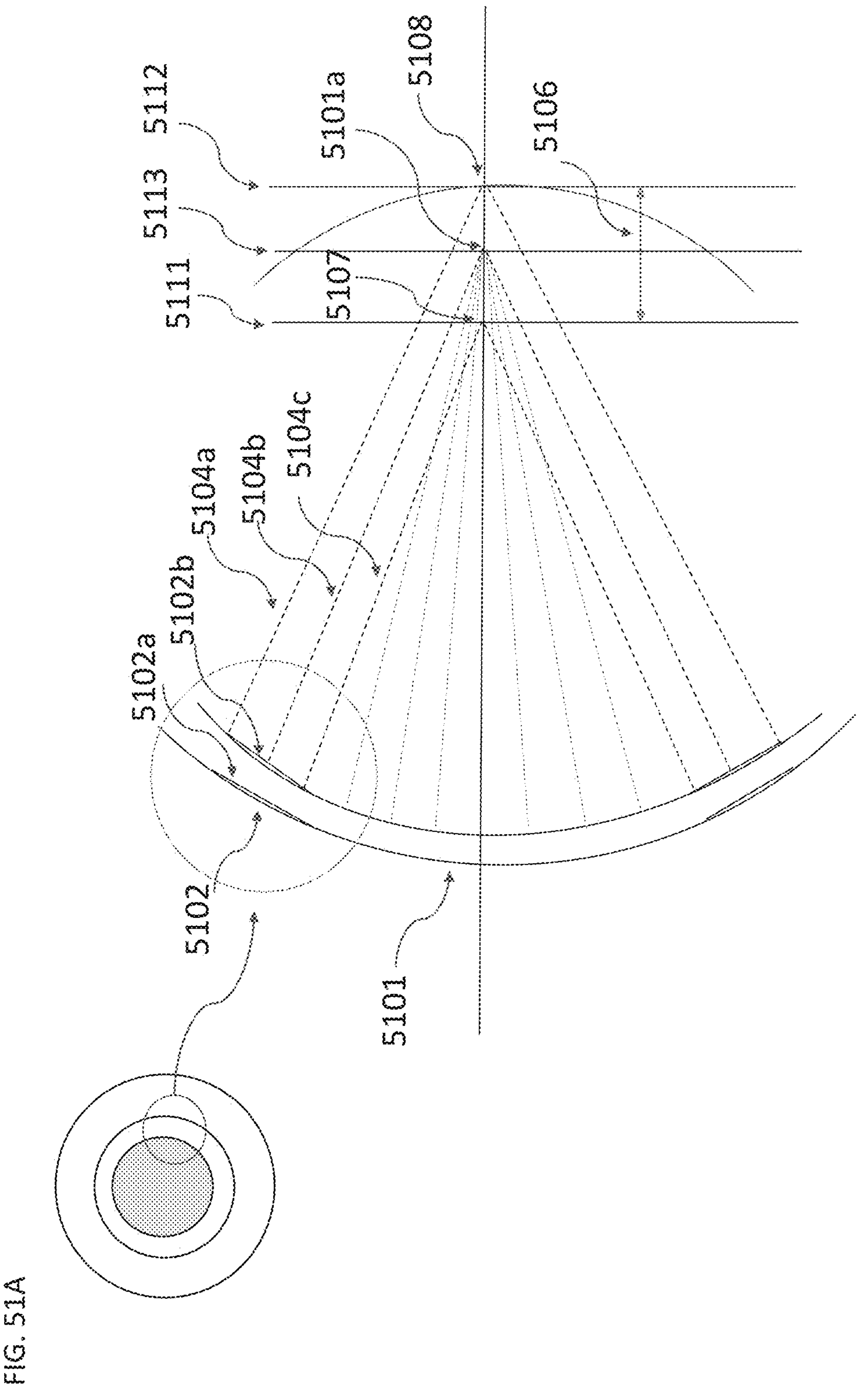
FIGS. 51A and 51B are schematic diagrams showing an ophthalmic lens incorporating a central optical zone surrounded by an annular zone to create an off-axis focal plane and a depth of focus in accordance with certain embodiments.

In accordance with an embodiment, FIG. 51A is a schematic diagrams showing an ophthalmic lens incorporating a central optical zone surrounded by an annular zone to create an off-axis focal plane and a depth of focus in accordance with certain embodiments. As illustrated in this example, both surfaces of the annular optical zone of the lens may be formed utilizing a surface with nil or substantially nil curvature (referred to as line curvature herein). In some embodiments, this configuration may create a depth of focus with the smallest light intensity areas from the low intensity annular zone rays and therefore results in a better image quality. In some embodiments, this design may also reduce or remove the presence of the off-axis focal planes along the optical axis.

FIG. 51A is a schematic diagram showing an ophthalmic lens comprising a central optical zone 5101 resulting in an on axis focal point 5101*a* in front of the retinal plane; an annular zone 5102 surrounding the central optical zone, the curvature of the annular optical zone 5102 formed by a line 5102*a* (for example, a flat line or a flatter line than the center zone) on the front surface and 5102*b* (for example a flat line or a steeper line than the center zone) on the back surface wherein light rays passing through the annular zone 5102 may have no off axis focal power and therefore results in light rays 5104*a*, 5104*b* and 5104*c* passing through the annular zone 5102 travel in a parallel, straight path to the image planes 5111, 5113 and 5112. The off axis light rays intersect the optical axis and interact with the on-axis rays from the central optical zone and result in a depth of focus 5106. A lens of this embodiment may not form off axis focal points nor have light rays converging or diverging beyond the off axis focal points that may increase light interference at image planes along the depth of focus 5106.

The annular zone 5102 is configured with lines that may not form any off axis power and so the annular zone is optically normal to the surface (where the annular zone on axis power profile provides m=p<about ±20%) and light rays 5104*b* from the centermost portion of the annular zone being about coincident with the central zone focal point 5101*a* as they intersect the optical axis. Likewise, the light rays from the innermost 5104*c* and outermost 5104*a* portions of the annular zone form the endpoints of the depth of focus at 5107 and 5108 when they intersect the optical axis equidistant from the center zone focal point 5101*a*. In this configuration the depth of focus 5106 for the illustrated embodiment may be located wholly within the eye (i.e., anterior to the retinal plane). The absence of an off axis power means no off axis focal points (or defocus ring) are formed anterior to or behind the retinal image plane. This configuration may be desirable in some embodiments because the image quality may be improved at the image planes along the depth of focus 5106 because the interference of light rays along the depth of focus may be less than many embodiments, for example, the ophthalmic lens of FIGS. 44A and 44B.

Figure 51B:
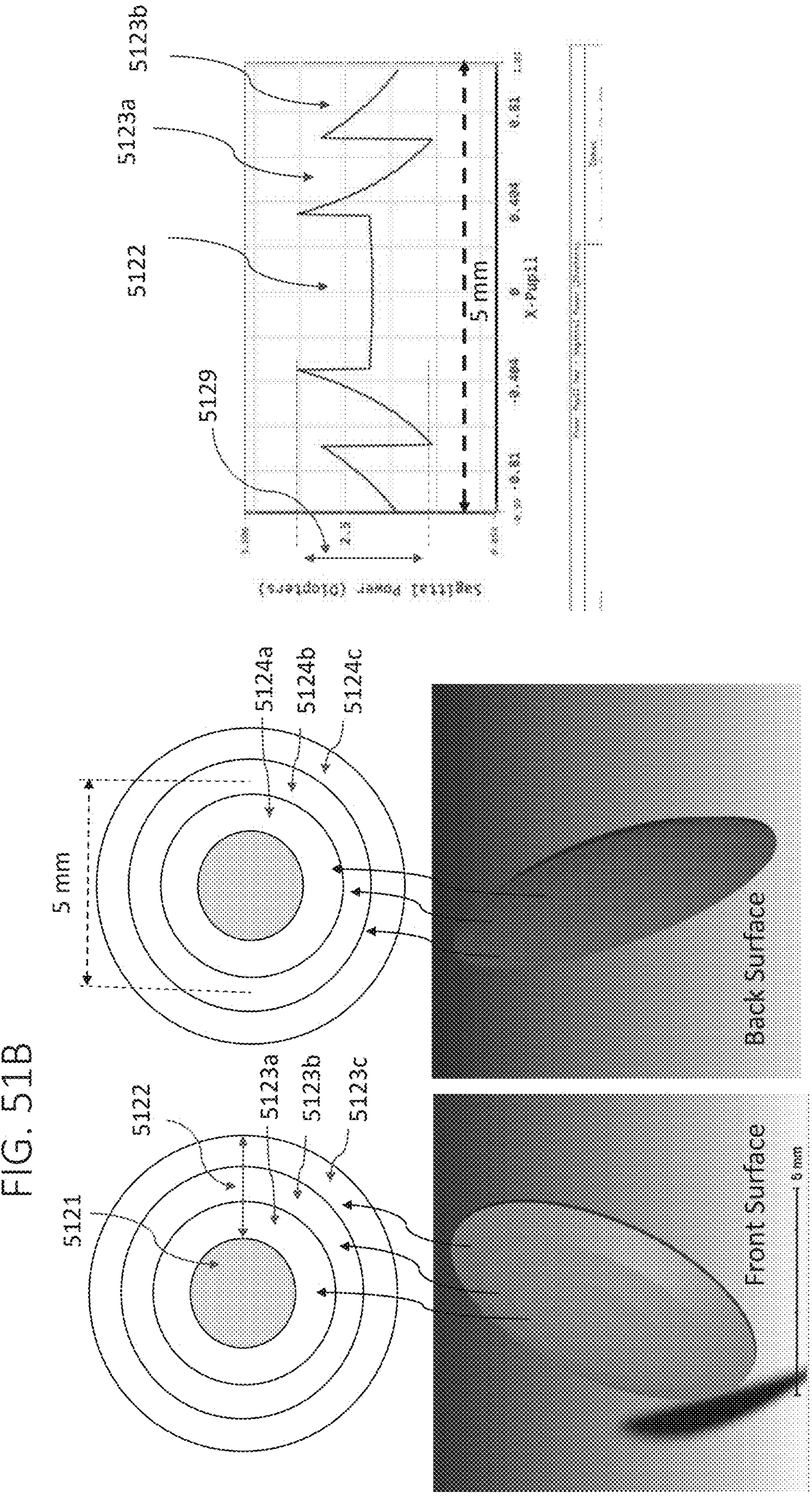

FIG. 51B, illustrates an exemplary power profile for a lens comprising a central zone and three regions within the annular zone formed by lines on the front and back surfaces. The ophthalmic lens simulated in FIG. 51B incorporates a central optical zone 5121 of 2.0 mm diameter with an on axis focal point not formed on the retinal plane (e.g., in front of the retinal plane); surrounded by an annular zone 5122 formed by 3 conjoined lines 5123*a*, 5123*b* and 5123*c* on the front surface and 5124*a*, 5124*b* and 5124*c* configured on the back surface to form a 3 mm wide annular optical zone comprising 3×1 mm wide concentric annular optical regions of zero off axis power. As described in FIG. 51A, the light rays passing through the annular zone with no off axis focal power simply pass through to intersect the optical axis and interact with the on-axis rays from the central optical zone 5121 and result in a depth of focus 5206 with reduced light interference at image planes along the depth of focus. Shown in FIG. 51B is a simulation of the sagittal power profile over a 6 mm aperture of the lens described in FIG. 51B. A 6 mm aperture may capture light rays from the central and 2 of the 3 annular line regions. The power profile shows the on axis power of the center zone 5122 and the on axis power profile of the two annular concentric regions (5123*a* innermost and 5123*b* middle) formed by lines on the front and back surface. As illustrated, the exemplary design provides about 1.5 D of depth of focus 5129. In both annular regions the p=m, <about ±20% and is consistent with an optically normal to the surface configuration in each region.

A desirable feature of forming the annular zone with lines on both surfaces of the lens is that it creates an annular zone with no off axis focal power and so wearability may be very easy. The widths of the zones may be similar to annular zones produced with single curves or multiple conjoined or infused curves and may be even wider. The absence of an off axis power means no off axis focal points (or defocus ring) are formed anterior to or behind the retinal image plane The interference of light rays at image planes are accordingly reduced as the light rays emanating from off axis ring defocus do not exist.

Figure 52:
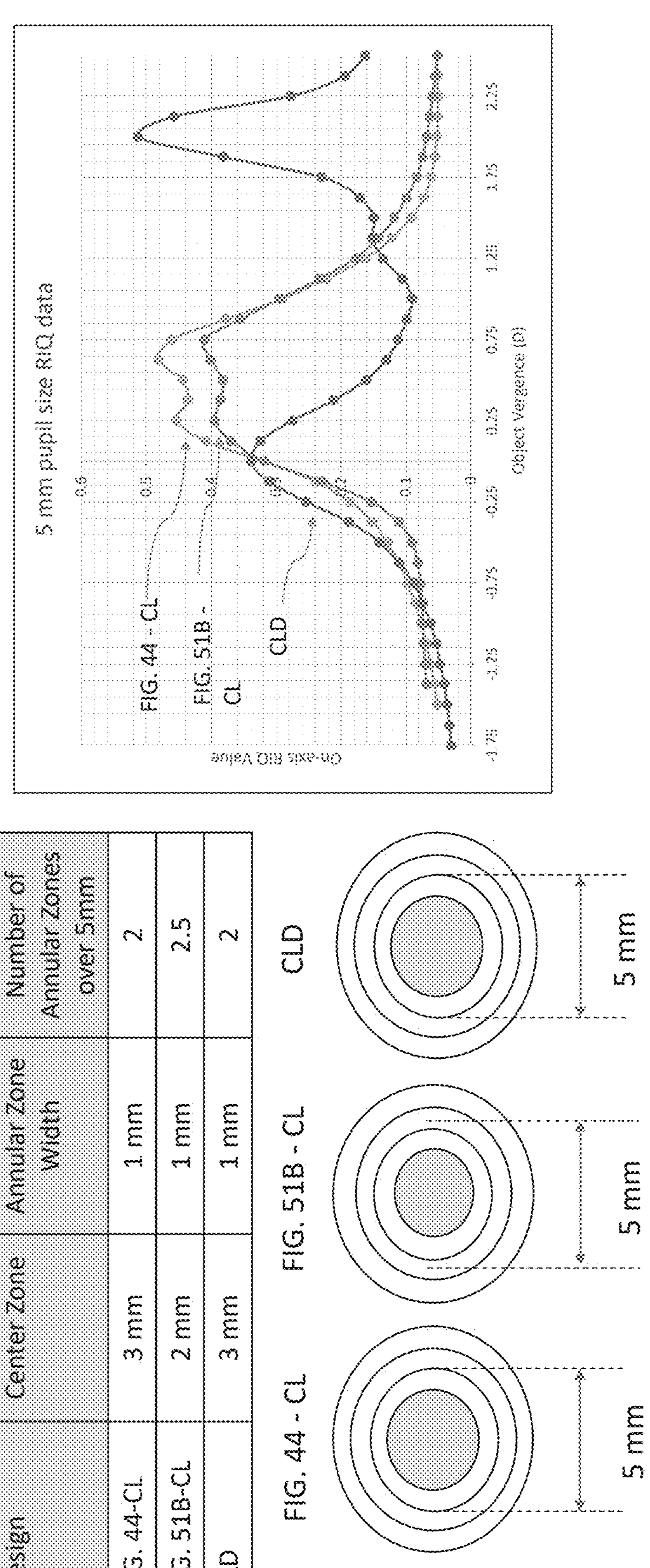
FIG. 52 is an illustration showing a comparison of retinal image quality (RIQ) between an existing lens design and the lens designs illustrated in FIGS. 44A, 44B, 51B, and a lens with a co-axial annular ring design.

FIG. 52 is a comparison of calculated through focus retinal image quality (RIQ) between: a) a commercially available lens comprising a distance center zone surrounded by alternating annular zones of coaxial lens powers of more positive and distance powers and referred to herein as 'coaxial lens design (CLD)' and b) the ophthalmic lens designs illustrated in FIGS. 44 and 51. The key parameters of the 3 lens designs are detailed in FIG. 52. The contact lens of FIG. 44 (FIG. 44CL) has a 3 mm central optical zone with an optical power that is hyperopic (positive) relative to the distance refractive error of the eye, and a 1 mm wide annular zone of +3.5 D add power. The contact lens of FIG. 51 (FIG. 51BCL) has a 2 mm diameter central optical zone with an optical power that is hyperopic (positive) relative to the distance refractive error of the eye and surrounded by 2×1 mm conjoined annular zones of 'plano' off-axis power configured with a 'line' for both front and back surfaces. The CLD has a 3.0 mm central optical zone powered for distance refractive error of the eye and surrounded by 3 annular optical zones, 1 mm in diameter, +2.00 D relative to the central optical zone power and alternating with the central zone power. All the optical zones of CLD are coaxial with the optical axis. The RIQ was calculated over a 5 mm pupil size for through focus' ranging from −1.75 D (behind the retina) to +2.25 D (anterior to the retina) (FIG. 52). As illustrated, the RIQ of CLD is bimodal around the two coaxial zone powers i.e. the distance power centered at the retinal plane (RIQ=0.34) and the +2.00 D addition power anterior to the retinal image plane (RIQ=0.38). The RIQ is significantly low in between the two peaks. In comparison, the lenses of FIG. 44 and FIG. 51B have a peak RIQ of 0.46 and 0.44, the RIQ is superior to RIQ of CLD over a broad range of vergences and is indicative of a true extended depth of focus with good RIQ.

In some embodiments, the ophthalmic lens may have a central zone refractive power that equals the distance refractive error of the eye plus about 1.00D for both myopia and presbyopia. In other embodiments, the central zone refractive power equals the distance refractive error of the eye plus about 0.75 D, 0.50 D, or 0.25 D, may be about 1.00 D-0.50 D, 0.75 D to 0.25, 0.50 D to 0.25 D. In some embodiments, more than one refractive zone of the ophthalmic lens contributes to restoring visual acuity if the eye. In some embodiments, more than one refractive zone of the ophthalmic lens may include central zone plus one of alternating angular rings (zones), conjoined annular rings, infused rings, annular zones with flat lines and so on.

In some embodiments, the tilt of the annular zone relative to the central optical zone may be configured to provide desired functionality with respect to an off-axis focal plane, extended depth of focus and good image quality. In some embodiments, the annular zone may have zero tilt when the curvature of the annular zone/ring is normal to the surface.

In some embodiments, the depth of focus provided by the ophthalmic lens may range from about 0.25 D to 5.0 D. For example, the depth of focus may be about 0.25 D, 0.5 D, 0.75 D, 1 D, 1.25 D, 1.5 D, 1.75 D, 2 D, 2.25 D, 2.5 D, 2.75 D, 3 D, 3.25 D, 3.5 D, 3.75 D, 4 D, 4.25 D, 4.5 D, 4.75 D, and/or 5 D. In some embodiments, the depth of focus may be about 1 D or more, or 1.5 D or more and/or 2 D or more. As discussed above, the depth of focus may be balanced or unbalanced relative to the on-axis focal point. In some embodiments, the depth of focus may be considered to be balanced when present on either side of the on-axis focal point (i.e., the on-axis focal point lies at about mid-point of the range of depth of focus, where the depth of focus, is the distance between the more positive or plane that is closest to the anterior eye and the less positive focal point that is farthest from the anterior eye. In some embodiments, the magnitude and location of the depth of focus may be controlled by ring and/or annular zone width, annular zone/ring power and central optic zone size for a given annular zone. Some embodiments may have a constant depth of focus across the range of central zone powers of the lens set whereas others may range in depth of focus depending on the power of the central optical zone. In some embodiments, there may be provided a set of lenses with a range of depth of focus for the management of the patient (e.g., myopia control with a short, an average and a long depth of focus for slowing/controlling/reducing axial progression of an eye). Some embodiments may have a lens set with a range of depth of focus providing one or more depth of focus for the management of the patient (e.g., presbyopia may have a short, an average and a long depth of focus for the correction of the additions). In some embodiments (e.g., presbyopia correction) the depth of focus prescribed may not be similar for the two eyes of an individual. For example, in some embodiments, the depth of focus may be 1.0 D in one eye and 2.0 D in the contralateral eye or may be equal but offset from each other. For example, the depth of focus may be 2 D in both eyes but the depth of focus in the non-dominant eye may be positioned relatively more anterior to the retina than in the dominant eye thereby providing an additional range of depth of focus and thus range of clear vision from intermediate to near distances for management in presbyopes. In some embodiments, the offset may be at least about 0.25 D or more or 0.5 D or more or about 1.5 D or more or about 2.50 D or less.

In some embodiments, the off-axis focal points may result in a ring focus whereas in some other embodiments may result in an incomplete ring. For example, an incomplete focal ring may have only a finite number of focal points (has a focus every 0.5 degree i.e., 720 focal points or every 1.0 degree i.e., 360 focal points or every 2 degrees i.e., 180 focal points), may have resulted as a result of the structure of the annular optical zone (the treatment zone is not a complete annulus, (e.g., an arc of 10 degrees or 15 degrees includes all of the focal points and/or an arc of 10 degrees or 15 degrees has no focal points)); and/or the relevant zone(s) on the ophthalmic lens is configured as a spiral, a polygon or any predefined direction forming a continuous off-axis focal shape that is a spiral, a line in form from the top view of the lens.

As described herein, the desirable surface profile of the annular zone may be provided either on the front surface (for example, a positive, elevated surface profile) and/or a back surface (for example, a negative, depressed surface elevation) or both. In some embodiments, the surface profile of the annular zone may or may not be a spheroidal torus. In some embodiments, the surface profile of the annular zone may be infused. In some embodiments, the annular zone may have a coaxial spherical curvature as part of the annular zone incorporating infused rings. In some embodiments, the surface profile of the annular zone may be conicroid. In some embodiments, the torus may be on the back surface and equal and opposite of the front surface (e.g., may be within the lens and the tilt, if applied on the back surface moves the focal point in the opposite direction of the case where the exact tilt was applied on the same curve on the front surface).

In some embodiments, the ophthalmic lenses described herein may provide improved vision as determined by any combination of overall vision scores, retinal image quality (RIQ) values, and/or through focus image quality (TFIQ) vision scores.

In some embodiments, the ophthalmic lens may comprise conjoined annuli surrounding a central zone. In some embodiments, the ophthalmic lens may comprise infused annuli surrounding a central zone. In some embodiments, the ophthalmic lens may comprise central zones with a radius in the range of 1 mm to 8 mm (e.g., 1 mm, 2 mm, 3 mm, 4 mm, 5 mm, 6 mm, 7 mm, and/or 8 mm). In some embodiments, the central zone is about 3 mm or less or more than about 0.5 mm.

In some embodiments, the ophthalmic lens may comprise a central optical zone and an annular optical zone comprising multiple annuli, wherein the width of each of the annuli of the annular optical zone may range from 0.05 mm to 2 mm (e.g., 0.05 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, 1 mm, 1.1 mm, 1.2 mm, 1.3 mm, 1.4 mm, 1.5 mm, 1.6 mm, 1.7 mm, 1.8 mm, 1.9 mm, and/or 2 mm). In some embodiments the annuli width may be less than about 0.05 mm, 0.1 mm, 0.15 mm, 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, 0.8 mm, 0.85 mm, 0.9 mm, 0.95 mm, 1 mm, 1.1 mm, 1.2 mm, 1.3 mm, 1.4 mm, 1.5 mm, 1.6 mm, 1.7 mm, 1.8 mm, 1.9 mm, and/or 2 mm. In some embodiments, the width may vary within the annuli or the width may vary across each individual annulus. In some embodiments, the widths of each of the annuli are less than 2 mm and/or less than 1.5 mm. In some embodiments, the annular zones may have tilts of about zero. In some embodiments, the retinal image quality (RIQ) may be above 0.4 for an annulus of relative power of +2.0 D.

The lens design sets of Lens1 and Lens 2 in Table 1 are designed with an annular zone that has a normal to the surface configuration. Both lenses 1 and 2 have a central optical zone and an annular optical zone, with the annular optical zone relatively positive in power than the central zone (referred to as an ADD). The central optical zone of Lens 1 incorporates power to correct the distance refractive error of the eye whereas the central zone of lens 2 is not powered to correct the distance refractive error of the eye. Lens 1 is configured so that the annular zone power provides a constant relatively positive power irrespective of the central zone power e.g., the ADD power is constant and does not change with the central zone power change. In comparison, the annular zone of lens 2 may be configured to provide different amounts of relative positive or ADD power across the power range for the central optical zone. Lens 2 may be configured with a different add for each central zone power while maintaining two important criteria: the annular optical zone is designed with a normal to the surface geometry to achieve a desirable amount of lateral separation and additionally refractive correction of the eye is not based on the central optical zone powered to correct for the distance refractive error of the eye.

TABLE 1

Example designs with peripheral zone power dependent (Example 1) and independent (Example 2) on central optic zone power.

| Patient | Lens 1 ADD constant with each Central power | | | Lens 2 ADD not constant with each central power | | |
|---|---|---|---|---|---|---|
| distance Refractive error | Center Zone power | Annular Zone power | Annular zone ADD or Treatment power (relative to center zone) | Center Zone power | Annular zone power | Annular zone ADD or Treatment power (relative to center zone) |
| +3.00 | +3.00 | +7.50 | +4.50 | +4.00 | +8.50 | +4.50 |
| +2.00 | +2.00 | +6.50 | +4.50 | +3.00 | +7.25 | +4.25 |
| +1.00 | +1.00 | +5.50 | +4.50 | +2.00 | +6.00 | +4.00 |
| 0.00 | 0.00 | +4.50 | +4.50 | +1.00 | +4.75 | +3.75 |
| −1.00 | −1.00 | +3.50 | +4.50 | 0.00 | +3.50 | +3.50 |
| −2.00 | −2.00 | +2.50 | +4.50 | −1.00 | +2.25 | +3.25 |
| −3.00 | −3.00 | +1.50 | +4.50 | −2.00 | +1.00 | +3.00 |
| −4.00 | −4.00 | +0.50 | +4.50 | −3.00 | −0.25 | +2.75 |
| −5.00 | −5.00 | −0.50 | +4.50 | −4.00 | −1.50 | +2.50 |

As described herein, the image quality at an image plane may be directly related to the characteristics of the light spot formed by light rays from an optical zone located on an ophthalmic lens at one or more image planes. Thus the optical quality of an ophthalmic lens may result from the interaction between image qualities of light spots formed across an infinite number of image planes formed between the lens and the final image plane. A cross section of a light spot has a dimension referred to as the spot size measured in microns. The light spot will also have a light intensity distribution across the diameter in the form of a range of more intense and less intense peaks. The strehl ratio is a measure of the distribution of light intensity across a light spot and is determined by the ratio of the peak light intensity of the spot image over a specified diameter divided by the peak light intensity of an image formed by a diffraction limited lens. A perfect image quality will have a ratio of 1 and a poor image quality will be close to 0. A spot of light at an image plane may consist of all the light rays passing through the image plane from the on axis and off axis optical elements located within the aperture of the lens forming the image at the image plane. Therefore the light spot may include light rays focused at the image plane and any light rays converging toward a focal point behind the image plane as well as any light rays diverging away from a focal point formed anteriorly to the image plane of interest. Thus the size and light intensity distribution of the light spot at the image plane, and thus the image quality, reflect the interference between any lower intensity light rays emanating from off axis optical zones and any higher intensity light rays formed by on axis optical zones at the image plane. The relative importance of the light spot characteristics may vary depending upon the optical design and application. In terms of an improved ophthalmic lens for myopia control and presbyopia and other applications benefiting from an extended depth of focus, the light intensity distribution may be an important property.

Therefore, the light intensity distribution of the light spot formed at an image plane is critical to image quality and should be specified.

To optimize the ophthalmic lens image quality in some embodiments, optical simulations have shown the light distribution of the spot formed at several image planes, and their location, may be specified. A first image plane may be located at the retinal image plane and a second image plane may be located more anterior to the retinal image plane and collectively may form the bounds of the depth of focus of at least 0.50 D or more while a third image plane may be located at the midpoint of the distance between the other two image planes.

Unexpectedly, findings show optimal image quality occurred when the high intensity rays from the center zone were focused at the third image plane and not at the retinal image plane. As such, in some embodiments, it was desirable that the high intensity light rays form the center zone form defocused spot sizes at the first and second image planes without an intense peak and resulting in a lower strehl ratio at both planes compared to the third image plane. Because the third image plane is at the midpoint of the distance between the first and second image planes, the light distribution of the high intensity spot sizes formed on the first image plane (from light rays converging to the third image plane) and the second image plane (from light rays diverging from the third image plane) are about equal and have about similar strehl ratios.

Clinical observations on eyes wearing prototype contact lenses with varying central optical zone size and power, annular optical zone widths and power and m:p ratios have determined that for a 5 mm lens aperture, the optimal light distribution intensity in a light spot formed at the first and second image planes as measured by the Strehl Ratio is less than 0.15 (e.g., <0.10 or 0.07 or less). Likewise, the optimal strehl ratio at the third image plane was higher than at the first and second image planes and e.g., <0.15, <0.10, and/or 0.07 or less. The m=p ratio of the power profile formed in the annular ring has been shown to be an influential control parameter for optical quality, namely m is about equal to p, based on optical simulations as discussed in several examples in FIGS. 44-51. With the third image plane located at the midpoint distance between the first and second image planes the m to p is also equal and clinical observations determined the optimal image quality occurs when the m:p ratio is between about <20%.

In some embodiments, the ophthalmic lenses described herein may be implemented in many ways for a range of purposes including: contact lens and/or spectacle lenses to correct and/or slow myopia; contact lenses for presbyopia contact lens (high, medium, low); lenses or anti-fatigue; as a single vision lens; contact lens for astigmatism; toric multifocal contact lens; an intraocular lens an implantable contact lens; corneal inlay, and for corneal shaping as in refractive surgery.

The lens designs disclosed herein may be produced using suitable ophthalmic lens production methods. For example, a contact lens may be fully molded, spun cast or semi-molded where one surface is molded and the second surface is created by an additional process such as lathing and the lens surfaces may be fully lathed. The ophthalmic lens may be an intraocular lens with bifocal, trifocal or multifocal power areas for distance vision correction and intermediate and near vision correction. A spectacle lens may be produced fully from a mold or grinding or digital freeform process. A semi-finished blank or stock of blanks with different base curves and parameters may contain a formed front surface or back surface and in one or more additional processing steps may be manufactured into the final prescription of the patient with one or more of the advantages of the improved ophthalmic lens described. For example, a semi-finished ophthalmic lens blank may have a dimension of at least 40 mm. In some embodiments a semi-finished ophthalmic lens blank may have a dimension of at least 55 mm, 60 mm, 70 mm, 75 mm or more diameter and may have a larger thickness than the final spectacle lens and may have a back surface not substantially the final shape or curvature of the finished ophthalmic lens that may be used by the patient and may also be used as a precursor of the final ophthalmic lens. The semi-finished lens blank may require further process steps so that a final ophthalmic lens with final lens surfaces and thicknesses to correct the wearers final prescription may then be shaped to fit the spectacle lens frame. The semi-finished lens blank or the final ophthalmic lens may also contain desired lens markings for enabling further production steps or lens fitting or frame fitting steps. The lens markings may be laser engraved and may be added at a suitable point of the manufacturing process. The front surface of the ophthalmic lens in this example may be the same as the front surface of the semi-finished blank so that the final lens for the patient may also be the final front surface shape of the final prescription and so the semi-finished lens blank may or may not include or already included the application of any lens coatings for antireflection, anti-scratching, light altering or light filtering treatments, or color changing or tinting of the lens. In this example, the semi-finished lens blank may require processing of the blank back surface in order to complete the final ophthalmic lens, the final back surface shape that co-operatively functions with the lens refractive index, front surface lens surface curvatures, lens treatments and lens thicknesses to deliver the final prescription and shape of the ophthalmic lens in a number of distance or near refractive errors including but may not be limited to sphere, cylinder, cylinder axes, centrations, prisms, progressive addition or multifocal power permutations that may be required for the patient. The improved ophthalmic spectacle lens design may provide improved optical performance including improved image quality, reduced oblique astigmatism or other distortion or aberration including cylinder power and wider fields of view irrespective of the monocular pupillary distances, fitting heights, progression lengths, tetrahedral angles, pantoscopic tilting or vertex distances.

One or more of the ophthalmic lens embodiments disclosed herein may also be incorporated into a suitable system or process, additional step or treatment, or procedure to enhance the efficiency of the lens production. One or more of the ophthalmic lens embodiments disclosed herein may also be incorporated into lens supply chain from material production to lens design to lens shaping and lens coatings and special features applied or included or lens fitting in to the spectacle frame. One or more of the ophthalmic lens embodiments disclosed herein may be suitable for used in ophthalmic spectacle lens where multiple focal points exist or other optical designs that may be inherently distorted and requiring improved image quality and/or vision. For example, unusual lens shapes, frame shapes, or highly curved lens surfaces such that may be required for wrap frames. The laterally separated optical axes may be applicable for aberration control including: surface distortions, oblique astigmatism and/or aberrations, where the improved design may benefit from including superior, inferior, temporal or nasal separation of the optical axes or combinations of these in cartesian coordinate or polar coordinate manner and may be designed in a substantially seamless and/or substantially junction less surface curvatures that manipulate the lens power for the desired optical performance. The final shape of exemplary embodiments of the ophthalmic lens disclosed herein may be produced by a suitable process and may including a grinding process, a digital diamond turned process, or a digital freeform process. For example, from a standard single vision lens, a lens blank, or a semi-finished blank having a final front surface shape and then the final lens design features may be designed to incorporate the prescription of the patient to correct one or more of the following: refractive error, presbyopia, myopia control and other optical feature to support the patients requirements prescribed by the practitioner or ordered by a user or both. The exemplary design embodiments may be used in conjunction with digital surfacing algorithms from a manufacturer, for example, digital surface and freeform processes such as Digital Ray Path Tracing (IOT, Madrid Spain) either in conjunction on the same surface or may be only a single surface.

In some embodiments, the first optical zone may have a substantially circular shape. In some embodiments, the first optical zone may be centrally located on the ophthalmic lens. In some embodiments, the first optical zone may have a substantially circular shape centrally located on the ophthalmic lens and the second optical zone may have a substantially annular shape surrounding the first optical zone. In some embodiments, the first optical zone and the second optical zone may be substantially concentric. In some embodiments, the first optical zone and the second optical zone may be substantially concentric but may not share a common axis. In some embodiments, the first optical zone and/or the second optical zone may be rotationally symmetric or asymmetric about the first axis.

In some embodiments, the ophthalmic lens may be configured to be used to slow, reduce or arrest the progression of myopia of an eye. In some embodiments, the ophthalmic lens may be configured to be used for the correction of myopia. In some embodiments, the ophthalmic lens may be configured to be used to correct presbyopia.

In some embodiments, the ophthalmic lens may be a simultaneous vision lens. In some embodiments, the ophthalmic lens may be a simultaneous vision bifocal lens. In some embodiments, the ophthalmic lens may be a distance center bifocal lens. In some embodiments, the ophthalmic lens may be a distance center bifocal contact lens. In some embodiments, the ophthalmic lens may be a simultaneous vision multifocal lens. In some embodiments, the ophthalmic lens may be a segmented vision lens.

In some embodiments, the ophthalmic lens may be configured to correct any combination of a plurality of distance, intermediate, and near vision.

In some embodiments, the ophthalmic lens may be one or more of the following: a spectacle lens, a contact lens, a corneal onlay, a corneal inlay, an intraocular lens, a sheet or film that may be applied to or attached to a spectacle lens.

Further advantages of the claimed subject matter will become apparent from the following examples describing certain embodiments of the claimed subject matter. In certain embodiments, one or more than one (including for instance all) of the following further embodiments may comprise each of the other embodiments or parts thereof.

A Examples

A1. An ophthalmic lens comprising: a first optical zone defined, at least in part, by a sphere having a first radius and having a first axis, the first optical zone being configured such that, in use with an eye, light passing through the first optical zone is refracted to a first focal point on the first axis; and a second optical zone defined, at least in part, by a sphere having a second radius, different than the first radius and configured such that, in use with the eye, light passing through the second optical zone is refracted to a second focal point (e.g., on a second axis); wherein the second focal point is displaced from the first axis by an amount substantially equal to a center zone diameter of the ophthalmic lens.

B Examples

B1. An ophthalmic lens comprising: a plurality of optical zones (e.g., 2, 3, 4, or 5 optical zones) configured such that, in use with an eye, light passing through the plurality of optical zones is refracted to a corresponding plurality of one or more focal points on a corresponding plurality of axes; wherein at least two of the plurality of optical zones do not share a common axis.

C Examples

C1. An ophthalmic lens comprising: at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points; wherein the one or more focal points from the at least one second optical zone are not on the first axis.

C2. The ophthalmic lens of any of the A, B, or C examples, wherein the at least one first optical zone and the at least one second optical zone define an optic zone of the ophthalmic lens.

C3. The ophthalmic lens of any of the A, B, or C examples, wherein the at least one first optical zone and the at least one second optical zone occupy a substantial portion of an optic zone of the ophthalmic lens (e.g., at least 90%, 95%, 98% or 99% of the surface area of an optic zone of the ophthalmic lens).

C4. The ophthalmic lens of any of the A, B, or C examples, wherein the ophthalmic lens is configured such that, in use with the eye, out-of-focus light associated with the at least one second optical zone does not substantially interfere with focal points associated with the at least one first optical zone.

C5. The ophthalmic lens of any of the A, B, or C examples, wherein the ophthalmic lens is configured such that, in use with the eye, defocused light associated with the at least one first optical zone does not substantially interfere with focal points associated with the at least one second optical zone.

C6. The ophthalmic lens of any of the A, B, or C examples, wherein the ophthalmic lens is configured such that, in use with the eye, interference at an in-focus focal point by the out-of-focus light is reduced, substantially reduced, or eliminated.

C7. The ophthalmic lens of any of the A, B, or C examples, wherein the at least one first optical zone comprises a first optical power and the at least one second optical zone comprises a second optical power different from the first optical power.

C8. The ophthalmic lens of any of the A, B, or C examples, wherein the at least one first optical zone comprises a first optical power and the at least one second optical zone comprises a second optical power relatively more positive than the first optical power.

C9. The ophthalmic lens of any of the A, B, or C examples, wherein the at least one first optical zone comprises a first optical power and the at least one second optical zone comprises a second optical power relatively less positive than the first optical power.

C10. The ophthalmic lens of any of the A, B, or C examples, wherein the at least one first optical zone is configured to correct one of more of the following: distance, intermediate and near vision; and/or the at least one second optical zone is configured to correct a different one of distance, intermediate, or near vision.

C11. The ophthalmic lens of any of the A, B, or C examples, wherein the at least one first optical zone is configured to correct distance vision and the at least one second optical zone is configured to correct near vision.

C12. The ophthalmic lens of any of the A, B, or C examples, wherein the at least one first optical zone is configured to correct near vision and the at least one second optical zone is configured to correct distance vision.

C13. The ophthalmic lens of any of the A, B, or C examples, wherein the first axis passes through the first optical zone.

C14. The ophthalmic lens of any of the A, B, or C examples, wherein the at least one first optical zone occupies a superior portion of the optic zone and the at least one second optical zone occupies an inferior portion of the optic zone.

C15. The ophthalmic lens of any of the A, B, or C examples, wherein the first axis is an axis of symmetry about which the optic zone of the ophthalmic lens is rotationally symmetrical.

C16. The ophthalmic lens of any of the A, B, or C examples, wherein the first axis is an optical axis of the at least one first optical zone.

C17. The ophthalmic lens of any of the A, B, or C examples, wherein the first focal point is on the first axis at a first distance from the ophthalmic lens and the second focal point is at a second distance from the ophthalmic lens, the second distance being different than the first distance and displaced from the first axis.

C18. The ophthalmic lens of any of the A, B, or C examples, wherein the second optical zone has a second axis associated with the second optical zone, the second axis being displaced from the first axis.

C19. The ophthalmic lens of any of the A, B, or C examples, wherein the lateral separation of the first axis and the second axis on the surface of the ophthalmic lens is about 0.5 mm (e.g., about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm or about 1 mm) or in some embodiments, the lateral separation of the first axis and the second axis on the surface of the ophthalmic lens may be about 0.25 mm, about 0.5 mm, or about 0.75 mm.

C20. The ophthalmic lens of any of the A, B, or C examples, wherein the lateral separation of the first axis and the second axis on the surface of the ophthalmic lens is less than about 0.5 mm (e.g., less than about 50 um, about 60 um, about 70 um, about 80 um, about 90 um, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, or about 0.6 mm) or in some embodiments, the lateral separation of the first axis and the second axis on the surface of the ophthalmic lens may be less than about 0.1 mm about 0.25 mm, or about 0.5 mm.

C21. The ophthalmic lens of any of the A, B, or C examples, wherein the lateral separation of the first axis and the second axis on the surface of the ophthalmic lens is less than about 0.5 mm (e.g., less than about 50 um, about 60 um, about 70 um, about 80 um, about 90 um, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, or about 0.6 mm) or in some embodiments, the lateral separation of the first axis and the second axis on the surface of the ophthalmic lens may be less than about 0.1 mm about 0.25 mm, or about 0.5 mm.

C22. The ophthalmic lens of any of the A, B, or C examples, wherein the lateral separation of the first axis and the second axis on the surface of the ophthalmic lens is more than about 50 um (e.g., more than about 50 um, about 60 um, about 70 um, about 80 um, about 90 um, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, or about 0.6 mm) or in some embodiments, the lateral separation of the first axis and the second axis on the surface of the ophthalmic lens may be more than about 0.1 mm about 0.25 mm, or about 0.5 mm.

C23. The ophthalmic lens of any of the A, B, or C examples, wherein the second focal point is on a second axis associated with the at least one second optical zone, the second axis being displaced from the first axis.

C24. The ophthalmic lens of any of the A, B, or C examples, wherein the at least one second optical zone is configured such that, in use with the eye, light passing through the at least one second optical zone is refracted to a plurality of second focal points, the plurality of second focal points being on a corresponding one or more of a plurality of second axes associated with the at least one second optical zone, the plurality of second axes being displaced from the first axis.

C25. The ophthalmic lens of any of the A, B, or C examples, wherein the at least one first optical zone has a substantially circular shape.

C26. The ophthalmic lens of any of the A, B, or C examples, wherein the at least one first optical zone is centrally located on the ophthalmic lens.

C27. The ophthalmic lens of any of the A, B, or C examples, wherein the at least one first optical zone has a substantially circular shape centrally located on the ophthalmic lens and the at least one second optical zone has a substantially annular shape surrounding the at least one first optical zone.

C28. The ophthalmic lens of any of the A, B, or C examples, wherein at least a portion of the at least one first optical zone has a substantially circular shape centrally located on the ophthalmic lens and at least a portion of the at least one second optical zone has a substantially annular shape surrounding the at least one first optical zone.

C29. The ophthalmic lens of any of the A, B, or C examples, wherein the at least one first optical zone comprises a first portion that has a substantially circular shape centrally located on the ophthalmic lens and a second portion that has a substantially annular shape surrounding the first portion.

C30. The ophthalmic lens of any of the A, B, or C examples, wherein the at least one second optical zone comprises a first portion that has a substantially annular shape surrounding the first optical zone and a second portion that has a substantially annular shape surrounding the first portion.

C31. The ophthalmic lens of any of the A, B, or C examples, wherein the at least one first optical zone and the at least one second optical zone are concentric (e.g., substantially concentric, and/or partially concentric).

C32. The ophthalmic lens of any of the A, B, or C examples, wherein the at least one first optical zone and the at least one second optical zone are substantially concentric but do not share a common axis.

C33. The ophthalmic lens of any of the A, B, or C examples, wherein the at least one first optical zone and/or the at least one second optical zone are rotationally symmetric about the first axis.

C34. The ophthalmic lens of any of the preceding claims, wherein the at least one first optical zone directly contacts the at least one second optical zone.

C35. The ophthalmic lens of any of the A, B, or C examples, wherein a blending zone is located between the at least one first optical zone and the at least one second optical zone.

C36. The ophthalmic lens of any of the A, B, or C examples, wherein the at least one first optical zone occupies more than 50% (e.g., about 55%, 60%, 65%, 70%, or 75%) of the surface area of the optic zone of the ophthalmic lens.

C37. The ophthalmic lens of any of the A, B, or C examples, wherein the at least one first optical zone occupies less than 50% (e.g., about 45%, 40%, 35%, 30%, or 25%) of the surface area of the optic zone of the ophthalmic lens.

C38. The ophthalmic lens of any of the A, B, or C examples, wherein the at least one first optical zone occupies about 60% (e.g., about 55%, 56%, 57%, 58%, 59%, 60%, 61%, 62%, 63%, 64%, or 65%) of the surface area of the optic zone of the ophthalmic lens.

C39. The ophthalmic lens of any of the A, B, or C examples, wherein the at least one first optical zone occupies about 40% (e.g., about 35%, 36%, 37%, 38%, 39%, 40%, 41%, 42%, 43%, 44%, or 45%) of the surface area of the optic zone of the ophthalmic lens.

C40. The ophthalmic lens of any of the A, B, or C examples, wherein the at least one first optical zone occupies less than about 75% (e.g., about 55%, 60%, 65%, 70%, or 75%) of the surface area of the optic zone of the ophthalmic lens.

C41. The ophthalmic lens of any of the A, B, or C examples, wherein the at least one first optical zone occupies more than about 25% (e.g., about 25%, 30%, 35%, 40%, or 45%) of the surface area of the optic zone of the ophthalmic lens.

C42. The ophthalmic lens of any of the A, B, or C examples, wherein the at least one first optical zone is defined, at least in part, by a sphere having a first radius and/or the at least one second optical zone is defined, at least in part, by a sphere having a second radius, different than the first radius.

C43. The ophthalmic lens of any of the A, B, or C examples, wherein the at least one first optical zone is defined, at least in part, by a sphere having a first radius and/or the at least one second optical zone is defined, at least in part, by a sphere having a second radius, smaller than the first radius.

C44. The ophthalmic lens of any of the A, B, or C examples, wherein the at least one first optical zone is defined, at least in part, by a sphere having a first radius and/or the at least one second optical zone is defined, at least in part, by a sphere having a second radius, larger than the first radius.

C45. The ophthalmic lens of any of the A, B, or C examples, wherein the at least one first optical zone is substantially circular in shape and has a diameter of about 3 mm (e.g., in some embodiments, the diameter may be about 2 mm, 2.5 mm, 3 mm, 3.5 mm, 4 mm, 2-4 mm, 2-3 mm, 3-4 mm, less than 4 mmm, less than 3.5 mm, and/or less the 3 mm).

C46. The ophthalmic lens of any of the A, B, or C examples, wherein the at least one second optical zone is substantially annular in shape and has an inner diameter of about 3 mm (e.g., in some embodiments, the inner diameter may be about 2 mm, 2.5 mm, 3 mm, 3.5 mm, 4 mm, 2-4 mm, 2-3 mm, 3-4 mm, less than 4 mmm, less than 3.5 mm, and/or less than 3 mm) and an outer diameter of about 7 mm (e.g., in some embodiments, the outer diameter may be about 5 mm, 5.5 mm, 6 mm, 6.5 mm, 7 mm, 7.5 mm, 8 mm, 5-8 mm, 6-7 mm, 6-8 mm, less than 8 mmm, less than 7.5 mm, and/or less than 7 mm).

C47. The ophthalmic lens of any of the A, B, or C examples, wherein the at least one first optical zone is substantially circular in shape and the at least one second optical zone is substantially annular in shape and an inner diameter of the at least one second optical zone is substantially equal to the diameter of the at least one first optical zone.

C48. The ophthalmic lens of any of the A, B, or C examples, wherein the position of the second focal point is determined, at least in part, by reducing and/or eliminating the tilt of the front surface of the second optical zone relative to the radius of curvature of the first optical zone.

C49. The ophthalmic lens of any of the A, B, or C examples, wherein the at least one second optical zone is configured such that, in use with the eye, the light passing through the at least one second optical zone is refracted to multiple (e.g., 1, 2, 3, 4, 5, 6, 7, 8, 9, 10, 11, 12, 13, 14, 15, or 16) focal points, not on the first axis.

C50. The ophthalmic lens of any of the A, B, or C examples, wherein the ophthalmic lens is configured to be used to slow, reduce or arrest the progression of myopia of an eye.

C51. The ophthalmic lens of any of the A, B, or C examples, wherein the ophthalmic lens is configured to be used for the correction of myopia.

C52. The ophthalmic lens of any of the A, B, or C examples, wherein the ophthalmic lens is configured to be used to correct presbyopia.

C53. The ophthalmic lens of any of the A, B, or C examples, wherein the ophthalmic lens is a simultaneous vision lens.

C54. The ophthalmic lens of any of the A, B, or C examples, wherein the ophthalmic lens is a segmented vision lens and/or a progressive additional multifocal (PAL) lens.

C55. The ophthalmic lens of any of the A, B, or C examples, wherein the ophthalmic lens is one or more of the following: a spectacle lens, a contact lens, a corneal onlay, a corneal inlay, and an intraocular lens.

D Examples

D1. An ophthalmic lens comprising: at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points positioned off-axis relative to the first focal point and on at least one focal plane different than a focal plane corresponding to the first focal point; wherein the at least one second optical zone is configured such that the light extending beyond the one or more focal points provides extended depth of focus.

D2. An ophthalmic lens comprising: at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points positioned off-axis relative to the first focal point and on at least one focal plane different than a focal plane corresponding to the first focal point; wherein the at least one first optical zone is configured such that first focal point is positioned in front of a retinal plane; and wherein the at least one second optical zone is configured such that the light extending beyond the one or more focal points in conjunction with the light refracted to the first focal point provides extended depth of focus.

D3. An ophthalmic lens comprising: at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points positioned off-axis relative to the first focal point and on at least one focal plane different than a focal plane corresponding to the first focal point; wherein the at least one first optical zone is configured such that first focal point is positioned in front of a retinal plane; and wherein the at least one second optical zone is configured such that the light extending beyond the one or more focal points in conjunction with the light refracted to the first focal point provides extended depth of focus extending from the retinal image plane to an anterior plane positioned in front of the first focal point at a location that results in the first focal point being substantially equidistant from the anterior plane and the retinal plane.

D4. An ophthalmic lens comprising: at least one first optical zone with a first axis, the at least one first optical zone being configured such that, in use with an eye, at least a portion of light passing through the at least one first optical zone is refracted to a first focal point on the first axis; and at least one second optical zone configured such that, in use with the eye, at least a portion of light passing through the at least one second optical zone is refracted to one or more focal points positioned off-axis relative to the first focal point and on at least one focal plane different than a focal plane corresponding to the first focal point; wherein the at least one first optical zone is configured such that first focal point is positioned in front of a retinal plane; and wherein the at least one second optical zone is configured such that the light extending beyond the one or more focal points in conjunction with the light refracted to the first focal point provides extended depth of focus located entirely within an eye.

D5. The ophthalmic lens of any of the D examples, wherein the at least one first optical zone has a substantially circular shape and centrally located on the ophthalmic lens and the at least one second optical zone has a substantially annular shape surrounding the at least one first optical zone.

D6. The ophthalmic lens of any of the D examples, wherein the at least one first optical zone and the at least one second optical zone are concentric.

D7. The ophthalmic lens of any of the D examples, wherein the one or more focal points positioned off-axis relative to the first focal point comprise a finite number of focal points (e.g., 2, 3, 4, 5, 6, 7, 8, 9, 10, 11, 12, 13, 14, 15, 16, 180, 360, or 720 focal points).

D8. The ophthalmic lens of any of the D examples, wherein the one or more focal points positioned off-axis relative to the first focal point comprise an infinite number of focal points.

D9. The ophthalmic lens of any of the D examples, wherein the one or more focal points positioned off-axis relative to the first focal point are positioned on at least 2 focal planes (e.g., at least 2, 3, 4, or 5 focal planes).

D10. The ophthalmic lens of any of the D examples, wherein the quantity and position of the one or more focal points is determined based at least in part on any combination of one or more of a width of the at least one second optical zone, a curvature of the at least one second optical zone, a location of the at least one second optical zone, a base power of the at least one second optical zone, and/or a lateral separation value of the at least one second optical zone.

D11. The ophthalmic lens of any of the D examples, wherein the depth of focus provided by the ophthalmic lens is determined based at least in part on any combination of one or more of a width of the at least one second optical zone, a curvature of the at least one second optical zone, a location of the at least one second optical zone, a base power of the at least one second optical zone, a lateral separation value of the at least one second optical zone, and/or the m and p components.

D12. The ophthalmic lens of any of the D examples, wherein the at least one second optical zone has a substantially annular shape with a width between about 0.2 to 3 mm (e.g., about 0.2 mm, 0.3 mm, 0.4 mm, 0.5 mm, 0.6 mm, 0.7 mm, 0.75 mm, 0.8 mm, 0.9 mm, 1 mm, 1.25 mm, 1.5 mm, 1.75 mm, 2 mm, 2.25 mm, 2.5 mm, 2.75 mm, 3 mm, 0.2-0.5 mm, 0.5-0.75 mm, 0.75-1 mm, 1-1.5 mm, 1.25-1.75 mm, 1.5-2 mm, 1.75-2.25 mm, 2-2.5 mm, 2.25-2.75 mm, and/or 2.5-3 mm).

D13. The ophthalmic lens of any of the D examples, wherein the at least one second optical zone has a substantially annular shape with a curvature of between about −10 to +10 D (e.g., about −10 D, −9 D, −8 D, −7 D, −6 D, −5 D, −4 D, −3 D, −2 D, −1 D, +1 D, +2 D, +3 D, +4 D, +5 D, +6 D, +7 D, +8 D, +9 D, and/or +10 D).

D14. The ophthalmic lens of any of the D examples, wherein the at least one second optical zone has a substantially annular shape with a base power of between about −20 to +20 D (−20 D, −19 D, −18 D, −17 D, −16 D, −15 D, −14 D, −13 D, −12 D, −11 D, −10 D, −9 D, −8 D, −7 D, −6 D, −5 D, −4 D, −3 D, −2 D, −1 D, +1 D, +2 D, +3 D, +4 D, +5 D, +6 D, +7 D, +8 D, +9 D, +10 D, +11 D, +12 D, +13 D, +14 D, +15 D, +16 D, +17 D, +18 D, +19 D, and/or +20 D).

D15. The ophthalmic lens of any of the D examples, wherein the at least one second optical zone has a substantially annular shape with a lateral separation value of between 0.2 to 1 mm on the surface of the lens (e.g., the lateral separation on the surface of the lens may be about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm or about 1 mm).

D16. The ophthalmic lens of any of the D examples, wherein the at least one second optical zone has a substantially annular shape with a lateral separation value of between 0.2 to 1 mm on the surface of the lens (e.g., the lateral separation on the surface of the lens may be less than about 50 um, 60 um, 70 um, 80 um, 90 um, 0.1 mm, 0.15 mm, 0.2 mm, 0.25 mm, 0.3 mm, 0.35 mm, 0.4 mm, 0.45 mm, 0.5 mm, 0.55 mm, and/or 0.6 mm).

D17. The ophthalmic lens of any of the D examples, wherein the at least one second optical zone has a substantially annular shape with a lateral separation value of between 0.2 to 1 mm on the surface of the lens (e.g., the lateral separation on the surface of the lens may be more than about 50 um, 60 um, 70 um, 80 um, 90 um, 0.1 mm, 0.15 mm, 0.2 mm, 0.25 mm, 0.3 mm, 0.35 mm, 0.4 mm, 0.45 mm, 0.5 mm, 0.55 mm, and/or 0.6 mm).

D18. The ophthalmic lens of any of the D examples, wherein the at least one focal plane is in front of, behind or in substantially the same plane as the first focal point.

D19. The ophthalmic lens of any of the D examples, wherein the rays that extend beyond the at least one focal planes also form a depth of focus behind and in front of the first focal point.

D20. The ophthalmic lens of any of the D examples, wherein the ratio of the amount of depth of focus in front of the first focal point to the amount of the depth of focus behind the first focal point may be about 100:0 (entirely in front of the first focal point), 90:10, 80:20, 75:25, 70:30, 60:40, 50:50 (equally in front of and behind the first focal point), 40:60, 30:70, 25:75, 20:80, 10:90, and/or 0:100 (entirely behind the first focal point).

D21. The ophthalmic lens of any of the D examples, wherein the at least one second zone cross-section, in two dimensions, has a focal length that is independent of the remaining portions of the ophthalmic lens.

D22. The ophthalmic lens of any of the D examples, wherein the at least one second zone is created by adjusting the curvature of the base lens on at least one of a front surface of the ophthalmic lens and/or a back surface of the ophthalmic lens.

D23. The ophthalmic lens of any of the D examples, wherein the at least one second zone is created by adjusting the curvature of the base lens on the front surface of the ophthalmic lens to create one of a plus optical zone or a minus optical zone.

D24. The ophthalmic lens of any of the D examples, wherein the at least one second zone is created by adjusting the curvature of the base lens on the back surface of the ophthalmic lens to create one of a plus optical zone or a minus optical zone.

D25. The ophthalmic lens of any of the D examples, wherein the at least one second optical zone has a substantially annular shape that includes a tilted curvature to influence (e.g., shift) the depth of focus.

D26. The ophthalmic lens of any of the D examples, wherein the at least one second optical zone has a substantially annular shape comprising multiple curve infusions (e.g., 2, 3, 4, 5, 6, 7, 8, 9, and/or 10 curve infusions) that have the same optical properties or different optical properties.

D27. The ophthalmic lens of any of the D examples, wherein the at least one second optical zone has a substantially annular shape comprising multiple conjoined curvatures (e.g., 2, 3, 4, 5, 6, 7, 8, 9, and/or 10 conjoined curvatures).

D28. The ophthalmic lens of any of the D examples, wherein the at least one second optical zone has a substantially annular shape created by replacing at least one (or both) surface curvatures of the lens with a line (e.g., a surface with no, or substantially no, curvature).

D29. The ophthalmic lens of any of the D examples, wherein the depth of focus provided by the ophthalmic lens and/or the annular zone may range from about 0.25 D to 5 D (e.g., about 0.25 D, 0.5 D, 0.75 D, 1 D, 1.25 D, 1.5 D, 1.75 D, 2 D, 2.25 D, 2.5 D, 2.75 D, 3 D, 3.25 D, 3.5 D, 3.75 D, 4 D, 4.25 D, 4.5 D, 4.75 D, and/or 5 D).

D30. The ophthalmic lens of any of the D examples, wherein the at least one first optical zone and the at least one second optical zone define an optic zone of the ophthalmic lens.

D31. The ophthalmic lens of any of the D examples, wherein the at least one first optical zone and the at least one second optical zone occupy substantially all of an optic zone of the ophthalmic lens.

D32. The ophthalmic lens of any of the D examples, wherein the ophthalmic lens is configured such that, in use with the eye, out-of-focus light associated with the at least one second optical zone does not interfere with focal points associated with the at least one first optical zone (e.g., does not substantially interfere with focal points associated with the at least one first optical zone).

D33. The ophthalmic lens of any of the D examples, wherein the ophthalmic lens is configured such that, in use with the eye, out-of-focus light associated with the at least one first optical zone does not interfere with focal points associated with the at least one second optical zone (e.g., does not substantially interfere with focal points associated with the at least one second optical zone).

D34. The ophthalmic lens of any of the D examples, wherein the ophthalmic lens is configured such that, in use with the eye, interference at an in-focus focal point by the out-of-focus light is controlled, reduced, substantially reduced, and/or eliminated.

D35. The ophthalmic lens of any of the D examples, wherein the at least one first optical zone comprises a first optical power and the at least one second optical zone comprises one or more second optical powers different (e.g., relatively positive or negative) from the first optical power.

D36. The ophthalmic lens of any of the D examples, wherein the at least one first optical zone is configured to correct one of distance, intermediate or near vision; and/or the at least one second optical zone is configured to correct a different one of distance, intermediate, or near vision.

D37. The ophthalmic lens of any of the D examples, wherein one of the at least one first optical zone and the at least one second optical zone is configured to correct distance vision and the other optical zone is configured to correct near vision.

D38. The ophthalmic lens of any of the D examples, wherein the first axis passes through the first optical zone.

D39. The ophthalmic lens of any of the D examples, wherein the first axis is an axis of symmetry about which the optic zone of the ophthalmic lens is rotationally symmetrical.

D40. The ophthalmic lens of any of the D examples, wherein the first axis is an optical axis of the first optical zone.

D41. The ophthalmic lens of any of the D examples, wherein the lateral separation of the first axis and the second axis on the surface of the ophthalmic lens is about 0.5 (e.g., about 0.2 mm, about 0.25 mm, about 0.3 mm, about 0.35 mm, about 0.4 mm, about 0.45 mm, about 0.5 mm, about 0.55 mm, about 0.6 mm, about 0.65 mm, about 0.7 mm, about 0.75 mm, about 0.8 mm, about 0.85 mm, about 0.9 mm or about 1 mm).

D42. The ophthalmic lens of any of the D examples, wherein the lateral separation of the first axis and the second axis on the surface of the ophthalmic lens is less than about 0.5 mm (e.g., less than about 50 um, about 60 um, about 70 um, about 80 um, about 90 um, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, or about 0.6 mm).

D43. The ophthalmic lens any of the D examples, wherein the lateral separation of the first axis and the second axis on the surface of the ophthalmic lens is less than about 0.5 mm (e.g., about 50 um, about 60 um, about 70 um, about 80 um, about 90 um, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, or about 0.6 mm).

D44. The ophthalmic lens of any of the D examples, wherein the lateral separation of the first axis and the second axis on the surface of the ophthalmic lens is more than about 50 um (e.g., more than about 50 um, about 60 um, about 70 um, about 80 um, about 90 um, about 0.1 mm, about 0.15 mm, about 0.2 mm, about 0.25 mm, about 0.3 mm, about 0.35 mm, about 0.4 mm, about 0.45 mm, about 0.5 mm, about 0.55 mm, or about 0.6 mm).

D45. The ophthalmic lens of any of the D examples, wherein the at least one first optical zone and/or the at least one second optical zone are rotationally symmetric about the first axis.

D46. The ophthalmic lens of any of the D examples, wherein the at least one first optical zone directly contacts the at least one second optical zone.

D47. The ophthalmic lens of any of the D examples, wherein the at least one first optical zone occupies more than 50% (e.g., about 55%, about 60%, about 65%, about 70%, or about 75%) of the surface area of the optic zone of the ophthalmic lens.

D48. The ophthalmic lens of any of the D examples, wherein the at least one first optical zone is defined, at least in part, by a sphere having a first radius and/or the at least one second optical zone is defined, at least in part, by a sphere having a second radius, different (e.g., smaller or larger) than the first radius.

D49. The ophthalmic lens of any of the D examples, wherein the at least one first optical zone is substantially circular in shape and has a diameter of about 3 mm (e.g., in some embodiments, the diameter may be about 2 mm, about 2.5 mm, about 3 mm, about 3.5 mm, about 4 mm, about 2-4 mm, about 2-3 mm, about 3-4 mm, less than about 4 mm, less than about 3.5 mm, and/or less than about 3 mm).

D50. The ophthalmic lens of any of the D examples, wherein the at least one second optical zone is substantially annular in shape and has an inner diameter of about 3 mm (e.g., in some embodiments, the inner diameter may be about 2 mm, about 2.5 mm, about 3 mm, about 3.5 mm, about 4 mm, about 2-4 mm, about 2-3 mm, about 3-4 mm, less than about 4 mm, less than about 3.5 mm, and/or less than about 3 mm) and an outer diameter of about 7 mm (e.g., in some embodiments, the outer diameter may be about 5 mm, about 5.5 mm, about 6 mm, about 6.5 mm, about 7 mm, about 7.5 mm, about 8 mm, about 5-8 mm, about 6-7 mm, about 6-8 mm, less than about 8 mm, less than about 7.5 mm, and/or less than about 7 mm).

D51. The ophthalmic lens of any of the D examples, wherein the at least one first optical zone is substantially circular in shape and the at least one second optical zone is substantially annular in shape and an inner diameter of the at least one second optical zone is substantially equal to the diameter of the at least one first optical zone.

D52. The ophthalmic lens of any of the D examples, wherein the ophthalmic lens is configured to be used to slow, reduce or arrest the progression of myopia of an eye.

D53. The ophthalmic lens of any of the D examples, wherein the ophthalmic lens is configured to be used for the correction of myopia.

D54. The ophthalmic lens of any of the D examples, wherein the ophthalmic lens is configured to be used to correct presbyopia.

D55. The ophthalmic lens of any of the D examples, wherein the ophthalmic lens is a simultaneous vision lens.

D56. The ophthalmic lens of any of the D examples, wherein the ophthalmic lens is a segmented vision lens and/or a progressive additional multifocal (PAL) lens.

It will be understood that the embodiments disclosed and defined in this specification extends to all alternative combinations of two or more of the individual features mentioned or evident from the text or drawings. All of these different combinations constitute various alternative aspects of the present disclosure.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

The invention claimed is:

1. An ophthalmic lens comprising:

at least one first optical zone with a first axis, the at least one first optical zone being configured such that, in use with an eye, at least a portion of light passing through the at least one first optical zone is refracted to a first focal point on the first axis; and a second optical zone having a substantially annular shape comprising a plurality of curvatures including at least a first curvature conjoined to a second curvature, wherein the plurality of curvatures are configured such that, in use with the eye, at least a portion of light passing through each of the curvatures is refracted to one or more focal points positioned off-axis relative to the first focal point and on at least one focal plane different than a focal plane corresponding to the first focal point;

wherein at least the first curvature and the second curvature are located within a diameter of 7 mm of the ophthalmic lens.

2. The ophthalmic lens of claim 1, wherein the at least one first optical zone has a substantially circular shape and centrally located on the ophthalmic lens and the second optical zone surrounds the at least one first optical zone.

3. The ophthalmic lens of claim 1, wherein the first optical zone and the at least one second optical zone are concentric.

4. The ophthalmic lens of claim 1, wherein the one or more focal points positioned off-axis relative to the first focal point comprise a finite number of focal points.

5. The ophthalmic lens of claim 1, wherein the one or more focal points positioned off-axis relative to the first focal point comprise an infinite number of focal points.

6. The ophthalmic lens of claim 1, wherein the one or more focal points positioned off-axis relative to the first focal point are positioned on at least 2 focal planes.

7. The ophthalmic lens of claim 1, wherein the quantity and position of the one or more focal points is determined based at least in part on any combination of one or more of a width of each of the plurality of curvatures, a curvature of each of the plurality of curvatures, a location of each of the plurality of curvatures and/or a lateral separation value of the one or more off-axis focal points formed by each of the plurality of curvatures from the first focal point on the first axis.

8. The ophthalmic lens of claim 1, wherein the depth of focus provided by the ophthalmic lens is determined based at least in part on any combination of one or more of a width of each of the plurality of curvatures, a curvature of each of the plurality of curvatures, a location of each of the plurality of curvatures, a lateral separation value of the one or more off-axis focal points formed by each of the plurality of curvatures from the first focal point on the first axis, and/or at least one m and at least one p components.

9. The ophthalmic lens of claim 1, wherein each of the plurality of curvatures has a substantially annular shape with a width between about 0.05 to 3 mm.

10. The ophthalmic lens of claim 1, wherein the second optical zone has a power of between about −20 to +20 D.

11. The ophthalmic lens of claim 1, wherein the second optical zone has a second axis displaced from the first axis and a lateral separation value of the lens is between 0.2 to 1 mm.

12. The ophthalmic lens of claim 1, wherein the at least one focal plane is in front of, behind or in substantially the same plane as the first focal point.

13. The ophthalmic lens of claim 1, wherein the ratio of the amount of depth of focus in front of the first focal point to the amount of the depth of focus behind the first focal point may be about 100:0, 90:10, 80:20, 75:25, 70:30, 60:40, 50:50, 40:60, 30:70, 25:75, 20:80, 10:90, and/or 0:100.

14. The ophthalmic lens of claim 1, wherein each of the plurality of curvatures has a cross-section, in two dimensions, has a focal length that is independent of a first focal length of the at least one first optical zone of the ophthalmic lens.

15. The ophthalmic lens of claim 1, wherein each of the plurality of curvatures is created by adjusting the curvature of the base lens on at least one of a front surface of the ophthalmic lens and/or a back surface of the ophthalmic lens.

16. The ophthalmic lens of claim 1, wherein each of the plurality of curvatures is created by adjusting the curvature of a base lens on a front surface of the ophthalmic lens to create one of a plus optical zone or a minus optical zone.

17. The ophthalmic lens of claim 1, wherein each of the plurality of curvatures is created by adjusting the curvature of a base lens on a back surface of the ophthalmic lens to create one of a plus optical zone or a minus optical zone.

18. The ophthalmic lens of claim 1, wherein each of the plurality of curvatures has a substantially annular shape that includes a tilted curvature to influence the depth of focus.

19. The ophthalmic lens of claim 1, wherein each of the plurality curvatures has a substantially annular shape comprising multiple curve infusions that have the same optical properties or different optical properties.

20. The ophthalmic lens of claim 1, wherein each of the plurality of curvatures includes a line curvature on a front surface and/or back surface of the ophthalmic lens.

21. The ophthalmic lens of claim 1, wherein the depth of focus provided by the ophthalmic lens and/or the second optical zone may range from about 0.25 D to 5 D.

22. The ophthalmic lens of claim 1, wherein the at least one first optical zone and the second optical zone define an optic zone of the ophthalmic lens.

23. The ophthalmic lens of claim 1, wherein the at least one first optical zone and the second optical zone occupy a portion of an optic zone of the ophthalmic lens.

* * * * *